United States Patent
Liu et al.

(10) Patent No.: US 10,464,999 B2
(45) Date of Patent: *Nov. 5, 2019

(54) ANTI-TRANSTHYRETIN ANTIBODIES

(71) Applicants: PROTHENA BIOSCIENCES LIMITED, Dublin (IE); UNIVERSITY HEALTH NETWORK, Toronto (CA)

(72) Inventors: Yue Liu, Foster City, CA (US); Tarlochan S. Nijjar, Orinda, CA (US); Avijit Chakrabartty, Vaughan (CA); Jeffrey N. Higaki, San Mateo, CA (US)

(73) Assignees: PROTHENA BIOSCIENCES LIMITED, Dublin (IE); UNIVERSITY HEALTH NETWORK, Toronto, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,423

(22) Filed: Jul. 2, 2016

(65) Prior Publication Data

US 2017/0058023 A1    Mar. 2, 2017

Related U.S. Application Data

(63) Continuation-in-part of application No. 15/009,662, filed on Jan. 28, 2016, now abandoned.

(Continued)

(51) Int. Cl.
*G01N 33/38* (2006.01)
*A61K 39/00* (2006.01)
(Continued)

(52) U.S. Cl.
CPC .......... *C07K 16/18* (2013.01); *A61K 51/1018* (2013.01); *A61K 2039/505* (2013.01);
(Continued)

(58) Field of Classification Search
None
See application file for complete search history.

(56) References Cited

U.S. PATENT DOCUMENTS 5,530,101 A    6/1996    Queen et al.
9,534,048 B2   1/2017    Chakrabartty et al.
(Continued)

FOREIGN PATENT DOCUMENTS

WO    WO 2010/030203 A1    3/2010
WO    WO 2014/124334 A2    8/2014
(Continued)

OTHER PUBLICATIONS

Fundamental Immunology, Third edition, 1993, William E. Paul (Editor).*

(Continued)

*Primary Examiner* — Aurora M Fontainhas
(74) *Attorney, Agent, or Firm* — Alston & Bird LLP

(57) ABSTRACT

The invention provides antibodies that specifically bind transthyretin (TTR). The antibodies can be used for treating or effecting prophylaxis of diseases or disorders associated with TTR accumulation or accumulation of TTR deposits (e.g., TTR amyloidosis). The antibodies can also be used for diagnosing TTR amyloidosis and inhibiting or reducing aggregation of TTR, among other applications.

78 Claims, 35 Drawing Sheets
(4 of 35 Drawing Sheet(s) Filed in Color)
Specification includes a Sequence Listing.

Related U.S. Application Data

(60) Provisional application No. 62/266,556, filed on Dec. 11, 2015, provisional application No. 62/109,002, filed on Jan. 28, 2015.

(51) Int. Cl.
- C07K 16/46 (2006.01)
- C07K 16/18 (2006.01)
- A61K 51/10 (2006.01)

(52) U.S. Cl.
CPC ...... C07K 2317/24 (2013.01); C07K 2317/34 (2013.01); C07K 2317/41 (2013.01); C07K 2317/56 (2013.01); C07K 2317/565 (2013.01); C07K 2317/567 (2013.01); C07K 2317/734 (2013.01); C07K 2317/76 (2013.01); C07K 2317/92 (2013.01)

(56) References Cited

U.S. PATENT DOCUMENTS

| | | |
|---|---|---|
| 9,731,292 B2 | 8/2017 | Ermantraut et al. |
| 9,879,080 B2 | 1/2018 | Nijjar et al. |
| 2014/0056904 A1 | 2/2014 | Chakrabartty et al. |
| 2016/0039916 A1 | 2/2016 | Jiang et al. |
| 2016/0251418 A1 | 9/2016 | Liu et al. |
| 2016/0257736 A1 | 9/2016 | Nijjar et al. |
| 2016/0257737 A1 | 9/2016 | Liu et al. |
| 2016/0340419 A1 | 11/2016 | Torikai et al. |
| 2016/0340420 A1 | 11/2016 | Zhang et al. |
| 2016/0347832 A1 | 12/2016 | Hosoi et al. |
| 2016/0355576 A1 | 12/2016 | Grimm et al. |
| 2017/0015737 A1 | 1/2017 | Nijjar et al. |
| 2017/0121398 A1 | 5/2017 | Nijjar et al. |
| 2018/0201670 A1 | 7/2018 | Nijjar et al. |

FOREIGN PATENT DOCUMENTS

| | | |
|---|---|---|
| WO | WO 2015/010118 A2 | 1/2015 |
| WO | WO 2015/092077 A1 | 6/2015 |
| WO | WO 2016/033326 A2 | 3/2016 |
| WO | WO 2016/120809 A1 | 8/2016 |
| WO | WO 2016/120810 A1 | 8/2016 |
| WO | WO 2016/120811 A1 | 8/2016 |
| WO | WO 2018/007922 A2 | 1/2018 |
| WO | WO 2018/007923 A2 | 1/2018 |
| WO | WO 2018/007924 A2 | 1/2018 |

OTHER PUBLICATIONS

Rudikoff et al., Single amino acid substitution altering antigen-binding specificity.Proc Natl Acad Sci U S A. Mar. 1982; 79(6): 1979-1983.*

Sharma et al., Identification of Autoantibodies against Transthyretin for the Screening and Diagnosis of Rheumatoid Arthritis. PLoS One 9(4): e93905. doi:10.1371/journal.pone.0093905.*

Bergström, et al., "Surface exposed epitopes and structural heterogeneity of in vivo formed transthyretin amyloid fibrils," Biophysical Research Communications, 348:532-539 (2006).

Goldsteins, et al., "Exposure of cryptic epitopes on transthyretin only in amyloid and in amyloidogenic mutants," Proc. Natl. Acad. Sci. USA, vol. 96, pp. 3108-3113 (Mar. 1999).

Gustavsson, et al., "Antigenic Mapping of Transthyretin Purified from Plasma and Amyloid Fibrils and within in Situ Tissue Localizations," American Journal of Pathology, vol. 144, No. 6, pp. 1301-1311 (Jun. 1994).

Redondo, et al., "Search for Intermediate Structures in Transthyretin Fibrillogenesis: Soluble Tetrameric Tyr78Phe TTR Expresses a Specific Epitope Present Only in Amyloid Fibrils," J. Mol. Biol., 304, 461-470 (2000).

Terzaki, et al., "Immunization in familial amyloidotic polyneuropathy: counteracting deposition by immunization with a Y78F TTR mutant," Laboratory Investigation, 86, 23-31 (2006).

Phay, et al., "Transthyretin Aggregate-Specific Antibodies Recognize Cryptic epitopes on Patient-Derived Amyloid Fibrils," Rejuvenation Research, vol. 17, No. 2, pp. 97-105 (2014).

PCT/IB2016/050415 International Search Report and Written Opinion dated Mar. 24, 2016.

Leger, et al., "Humanization of Antibodies," Molecular Medicine and Medicinal Chemistry, pp. 1-23, (Jan. 1, 2011).

Almagro, et al., "Humanization of antibodies," Frontiers in Bioscience, 12:1619-1633, (Jan. 1, 2008).

PCT/IB2016/050414 International Search Report and Written Opinion dated Apr. 25, 2016.

PCT/IB2016/050416 International Search Report and Written Opinion dated May 18, 2016.

Hernandez, et al., "Identification of new pathogenic candidates for diabetic mascular edema using fluorescence-based difference gel electrophoresis analysis", Diabetes Metab Res Rev, 29:499-506 (2013). [Retrieved from the Internet Mar. 8, 2017: https://www.researchgate.net/publication/236140050_Identification_of_new_pathogenic_candidates_for_diabetic_macular_edema_using_fluorescence-based_difference_gel_electrophoresis_analysis].

Dias-Santos, et al., "Macular and Iptic disc dedma and retinal vascular leakage in familal amyloid polyneuropathy with a transthyretin Val30Met mutation: a case report", J Med Case Rep, 8:327 (Oct. 4, 2014).

U.S. Appl. No. 15/009,662 Restriction Requirement dated Sep. 20, 2016.

U.S. Appl. No. 15/009,666 Restriction Requirement dated Sep. 20, 2016.

Adekar, et al., "Inherent Anti-amyloidogenic Activity of Human Immunoglobulin γ Heavy Chains," J Biol Chem, 285(2):1066-74, (2010).

Cardoso, et al., "Transthyretin Fibrillogenesis Entails the Assembly of Monomers: A Molecular Model for in Vitro Assembled Transthyretin Amyloid-like Fibrils," J Mol Biol, 317:683-95, (2002).

Chen, et al., "Endoplasmic Reticulum Proteostasis Influences the Oligomeric State of an Amyloidogenic Protein Secreted from Mammalian Cells," Cell Chem Biol, 23:1282-1293, (2016).

Galant, et al., "Substoichiometric inhibition of transthyretin misfolding by immune-targeting sparsely populated misfolding intermediates: a potential diagnostic and therapeutic for TTR amyloidoses," Sci Rep, 6:1-11, srep 25080, Apr. 28, 2016. [Retrieved from the Internet Feb. 27, 2017: <www.nature.com/scientificreports>].

Higaki, et al., "Novel conformation-specific monoclonal antibodies against amyloidogenic forms of transthyretin," Amyloid, 23(2):86-97, (2016).

Jiang, et al., "An Engineered Transthyretin Monomer that Is Nonamyloidogenic, Unless It Is Partially Denatured," Biochemistry, 40(38):11442-11452, (2011).

Johnson, et al., "The Transthyretin Amyloidoses: From Delineating the Molecular Mechanism of Aggregation Linked to Pathology to a Regulatory-Agency-Approved Drug," J Mol Biol, 421:185-203, (2012).

Lai, et al., "The Acid-Mediated Denaturation Pathway of Transthyretin Yields a Conformational Intermediate That Can Self-Assemble into Amyloid," Biochemistry, 35(20):6470-6482, (1996).

Lashuel, et al., "Characterization of the Transthyretin Acid Denaturation Pathways by Analytical Ultracentrifugation: Implications for Wild-Type, V30M, and L55P Amyloid Fibril Formation," Biochemistry, 37(51):17851-17864, (1998).

Levites, et al., "A Human Monoclonal IgG That Binds Aβ Assemblies and Diverse Amyloids Exhibits Anti-Amyloid Activities In Vitro and In Vivo," J Neurosci, 35(16):6265-6276, (2015).

McCutchen, et al., "Comparison of Lethal and Nonlethal Transthyretin Variants and Their Relationship to Amyloid Disease," Biochemistry, 34(41):13527-13536, (1995).

Miroy, et al., "Inhibiting transthyretin amyloid fibril formation via protein stabilization," Proc Natl Acad Sci USA, 93:15051-15056, (1996).

(56) References Cited

OTHER PUBLICATIONS

O'Nuallain, et al., "Localization of a Conformational Epitope Common to Non-Native and Fibrillar Immunoglobulin Light Chains," *Biochemistry*, 46(5):1240-1247, (2007).
O'Nuallain, et al., "Conformational Abs recognizing a generic amyloid fibril epitope," *Proc Natl Acad Sci USA*, 99(3):1485-1490, (2002).
O'Nuallain, et al., "Anti-amyloidogenic Activity of IgGs Contained in Normal Plasma," *J Clin Immunol*, 30 Suppl 1:S37-S42, (2010).
Phay, et al., "IgG Conformer's Binding to Amyloidogenic Aggregates," *PLoS One*, 10(9):1-25, (2015).
Planque, et al., "Physiological IgM Class Catalytic Antibodies Selective for Transthyretin Amyloid," *J Biol Chem*, 289(19):13243-13258, (2014).
Planque, et al., "Specific Amyloid β Clearance by a Catalytic Antibody Construct," *J Biol Chem*, 290(16):10229-10241, (2015).
Quintas, et al., "Tetramer Dissociation and Monomer Partial Unfolding Precedes Protofibril Formation in Amyloidogenic Transthyretin Variants," *J Biol Chem*, 276(29):27207-27213, (2001).
Su, et al., "Antibody therapy for familial amyloidotic polyneuropathy," *Amyloid*, 19(51):45-46, (2012).
Hosoi, et al., "Novel Antibody for the Treatment of Transthyretin Amyloidosis," *J Biol Chem*, 291(48):25096-25105, (2016).
U.S. Appl. No. 15/009,667 Restriction Requirement dated Dec. 30, 2016.
U.S. Appl. No. 15/009,662 Non-Final Office Action dated Mar. 7, 2017.
Paul, "Fundamental Immunology" textbook under the heading "Fv Structure and Diversity in Dimensions," pp. 292-295, (1993).
Rudikoff, et al., "Single amino acid substitution altering antigen-binding specificity," *Proc. Natl Acad Sci USA*, 79(6):1979-1983, (1982).
U.S. Appl. No. 15/009,662 Examiner Initiated Interview Summary dated Mar. 7, 2017.
U.S. Appl. No. 15/009,666 Non-Final Office Action dated Mar. 6, 2017.
U.S. Appl. No. 15/009,666 Examiner Initiated Interview Summary dated Mar. 6, 2017.
U.S. Appl. No. 15/009,667 Non-Final Office Action dated Mar. 29, 2017.
U.S. Appl. No. 15/201,416 Restriction Requirement dated May 31, 2017.
U.S. Appl. No. 15/201,429 Restriction Requirement dated Jul. 3, 2017.
PCT/IB2016/050416 International Preliminary Report on Patentability dated Aug. 10, 2017.
PCT/IB2016/050415 International Preliminary Report on Patentability dated Aug. 10, 2017.
PCT/IB2016/050414 International Preliminary Report on Patentability dated Aug. 1, 2017.
PCT/IB2017/053991 Invitation to Pay Additional Fees dated Nov. 2, 2017.
U.S. Appl. No. 15/201,429 Non-Final Office Action dated Nov. 14, 2017.
PCT/162017/053984 Invitation to Pay Additional Fees dated Oct. 30, 2017.
PCT/IB2017/053991 International Search Report and Written Opinion dated Jan. 17, 2018.
PCT/IB2017/053984 International Search Report and Written Opinion dated Jan. 2, 2018.
PCT/IB2017/053987 International Search Report and Written Opinion dated Jan. 31, 2018.
U.S. Appl. No. 15/201,429 Final Office Action dated Jul. 9, 2018.
U.S. Appl. No. 15/201,429 Advisory Action dated Sep. 17, 2018.
PCT/IB2017/053987 International Preliminary Report on Patentability dated Jan. 8, 2019.
PCT/IB2017/053991 International Preliminary Report on Patentability dated Jan. 8, 2019.
PCT/IB2017/053984 International Preliminary Report on Patentability dated Jan. 8, 2019.
PCT/US2018/054723 International Search Report and Written Opinion dated Jan. 3, 2018.
Ionis Pharmaceuticals Announces Phase 3 NEURO-TTR Study of Inotersen (IONIS-TTRRx) Meets Both Primary Endpoints, Press Release, Carlsbad California, May 15, 2017.
PCT/US2018/062902 International Search Report and Written Opinion dated Apr. 7, 2019.
PCT/US2018/054720 International Search Report and Written Opinion dated Feb. 12, 2019.
Schonhoft, et al., "Peptide probes detect misfolded transthyretin oligomers in plasma of hereditary amyloidosis patients," Sci. Tranl. Med., 9, eaam 7621, (2017).
U.S. Appl. No. 15/201,429 Non-Final Office Action dated Mar. 5, 2019.
U.S. Appl. No. 15/861,600 Notice of Allowance and Examiner Initiated Interview Summary dated Mar. 18, 2019.
Damas, et al., "Review: TTR Amyloidosis—Structural Features Leading to Protein Aggregation and Their Implications on Therapeutic Strategies," Journal of Structural Biology, 120, 290-299, (2000).
U.S. Appl. No. 16/129,618 Non-Final Office Action and Interview Summary dated Aug. 22, 2019.
Carvalho, et al., "Liver Transplantation in Transthyretin Amyloidosis: Issues and Challenges," Liver Transplantation, 21:282-292, (2015).
Murray, et al., "Physiological consequences of changes in the primary structure," Human Biochemistry, vol. 1, p. 34, right column, (1993).

\* cited by examiner

|  |  |  |
|---|---|---|
| m9D5VH | EVKLVESGGGLVQPGGSLKLSCAASGFTFSSYTMSWVRQTPE | 42 |
| Mouse Model 1SEQ_H | EVKLVESGGGLVQPGGSLKLSCAASGFTFSSYTMSWARQTPE | 42 |
| Mouse Model 1MQK_H | EVKLQESGGGLVQPGGSLKLSCAASGFTFSIYTMSWVRQTPE | 42 |
| Human Acceptor BAC02114 | EVQLVESGGGLVQPGGSLRLSCAASGFTFSSYEMNWVRQAPG | 42 |
| Human Acceptor AAX82494 | QVQLQESGGGLVKPGGSLKLSCAASGFTFSSYGMSWVRQTPD | 42 |
| Hu9D5VHv1 | EVQLVESGGGLVQPGGSLRLSCAASGFTFSSYTMSWVRQAPG | 42 |
| Hu9D5VHv2 | EVQLVESGGGLVQPGGSLKLSCAASGFTFSSYTMSWVRQAPG | 42 |
| Hu9D5VHv2b | EVQLVESGGGLVQPGGSLKLSCAASGFTFSSYTMSWVRQTPE | 42 |
| Hu9D5VHv3 | EVQLVESGGGLVQPGGSLRLSCAASGFTFSSYTMSWVRQTPG | 42 |
| Hu9D5VHv3b | EVQLVESGGGLVQPGGSLKLSCAASGFTFSSYTMSWVRQAPG | 42 |
| Hu9D5VHv4 | EVQLVESGGGLVQPGGSLRLSCAASGFTFSSYTMSWVRQAPG | 42 |
| Hu9D5VHv4b | EVQLVESGGGLVQPGGSLKLSCAASGFTFSSYTMSWVRQAPG | 42 |
| Hu9D5VHv5 | EVQLVESGGGLVQPGGSLRLSCAASGFTFSSYTMSWVRQTPE | 42 |
| m9D5VH | KRLELVAEISNSGDTTYYPDTVKGRFTFSRDNAKNTLYLQMS | 84 |
| Mouse Model 1SEQ_H | KKLEWVAYISKGGGSTYYPDTVKGRFTISRDNAKNTLYLQMS | 84 |
| Mouse Model 1MQK_H | KRLEWVASINNGGGRTYYPDTVKGRFTISRDNAKNTLYLQMS | 84 |
| Human Acceptor BAC02114 | KGLEWVSYITSSGSTIYYADSVKGRFTISRDNAKNSLYLQMN | 84 |
| Human Acceptor AAX82494 | KRLEWVATISSGGSYTYYPDTVKGRFTISRDNAKNSLYLQMN | 84 |
| Hu9D5VHv1 | KGLEWVSEISNSGDTTYYPDTVKGRFTFSRDNAKNSLYLQSN | 84 |
| Hu9D5VHv2 | KGLEWVSEISNSGDTTYYPDTVKGRFTISRDNAKNSLYLQSN | 84 |
| Hu9D5VHv2b | KRLELVAEISNSGDTTYYPDTVKGRFTISRDNAKNTLYLQMS | 84 |
| Hu9D5VHv3 | KRLELVAEISNSGDTTYYPDTVKGRFTISRDNAKNSLYLQSN | 84 |
| Hu9D5VHv3b | KRLELVAEISNSGDTTYYPDTVKGRFTISRDNAKNTLYLQMS | 84 |
| Hu9D5VHv4 | KGLEWVSEISNSGDTTYYPDTVKGRFTISRDNAKNSLYLQSN | 84 |
| Hu9D5VHv4b | KRLELVAEISNSGDTTYYPDTVKGRFTISRDNAKNTLYLQMS | 84 |
| Hu9D5VHv5 | KRLELVAEISNSGDTTYYPDTVKGRFTISRDNAKNTLYLQMN | 84 |

FIG. 1A.1

| | 90 | 100 | 110 | 120 | | |
|---|---|---|---|---|---|---|
| m9D5VH | SLKSEDTAMYYCAR | HYYYGGGYGGWFFDV | WGTGTTVTVSS | | 124 | (SEQ ID NO.1) |
| Mouse Model 1SEQ_H | SLKSEDTALYYCAR-GAMFGNDFKYPMDR | | WGQGTSVTVSS | | 123 | (SEQ ID NO.2) |
| Mouse Model 1MQK_H | SLKSEDTAMYYCVR | HEYY-----YAMDY | WGQGTTVTVSS | | 118 | (SEQ ID NO.62) |
| Human Acceptor BAC02114 | SLRAEDTAVYYCAR | GGQGSRYYYYYGMDV | WGQGTTVTVSS | | 124 | (SEQ ID NO.3) |
| Human Acceptor AAX82494 | SLKSEDTAMYYCAR | LYYGYRYYF-----DY | WGQGTMVTVSS | | 120 | (SEQ ID NO.4) |
| Hu9D5VHv1 | SLKSEDTAVYYCAR | HYYYGGGYGGWFFDV | WGQGTTVTVSS | | 124 | (SEQ ID NO.5) |
| Hu9D5VHv2 | LLRAEDTAVYYCAR | HYYYGGGYGGWFFDV | WGQGTTVTVSS | | 124 | (SEQ ID NO.6) |
| Hu9D5VHv2b | SLKSEDTAMYYCAR | HYYYGGGYGGWFFDV | WGQGTLVTVSS | | 124 | (SEQ ID NO.7) |
| Hu9D5VHv3 | LLRAEDTAVYYCAR | HYYYGGGYGGWFFDV | WGQGTLVTVSS | | 124 | (SEQ ID NO.8) |
| Hu9D5VHv3b | SLKSEDTAMYYCAR | HYYYGGGYGGWFFDV | WGQGTLVTVSS | | 124 | (SEQ ID NO.9) |
| Hu9D5VHv4 | LLRAEDTAVYYCAR | HYYYGGGYGGWFFDV | WGQGTTVTVSS | | 124 | (SEQ ID NO.10) |
| Hu9D5VHv4b | SLKSEDTAMYYCAR | HYYYGGGYGGWFFDV | WGQGTLVTVSS | | 124 | (SEQ ID NO.11) |
| Hu9D5VHv5 | LLRAEDTAVYYCAR | HYYYGGGYGGWFFDV | WGQGTTVTVSS | | 124 | (SEQ ID NO.12) |

FIG. 1A.2

```
                        10         20         30         40
                         |          |          |          |
m9D5VL                  DIVMTQAAPSVPVTPGESVSISCRSSKSLLHSNGNTYLYW  40
Mouse Model 1MJU_L      DIVMTQAAPSVPVTPGESVSISCRSSKSLLHSNGNTYLYW  40
Human Acceptor ABC66952 DIVMTQSPLSLPVTPGEPASISCRSSKSLLHSNGYNYLDW  40
Hu9D5VLv1               DIVMTQSPLSLPVTPGEPASISCRSSNQSLLYSNGNTYLYW  40
Hu6C1VLv2               DIVMTQSPLSLPVTPGEPASISCRSSKSLLHSNGNTYLYW  40
Hu9D5VLv3               DIVMTQSPLSLPVTPGEPVSISCRSSKSLLHSNGNTYLYW  40
Hu9D5VLv4               DIVMTQSAPSLPVTPGESVSISCRSSKSLLHSNGNTYLYW  40
Hu9D5VLv5               DIVMTQSAPSLPVTPGESVSISCRSSKSLLHSNGNTYLYW  40

50         60         70         80
                         |          |          |          |
m9D5VL                  FLQRPGQSPQLLIYRVSNLASGVPDRFSGSGSGTAFTLRI  80
Mouse Model 1MJU_L      FLQRPGQSPQLLIYRVSNLASGVPDRFSGSGSGTAFTLRI  80
Human Acceptor ABC66952 YLQKPGQSPQLLIYRMSNLASGVPDRFSGSGSGTDFTLKI  80
Hu9D5VLv1               FLQKPGQSPQLLIYSGSNRASGVPDRFSGSGSGTDFTLKI  80
Hu6C1VLv2               YLQKPGQSPQLLIYRVSNLASGVPDRFSGSGSGTDFTLKI  80
Hu9D5VLv3               YLQKPGQSPQLLIYRVSNLASGVPSRFSGSGSGTDFTLKI  80
Hu9D5VLv4               FLQRPGQSPQLLIYRVSNLASGVPSRFSGSGSGTAFTLRI  80
Hu9D5VLv5               FLQRPGQSPQLLIYRVSNLASGVPSRFSGSGSGTAFTLRI  80

90        100        110
                         |          |          |
m9D5VL                  SRVEAEDVGVYYQMQHLEYPLTFGAGTKLELK   112 (SEQ ID NO.16)
Mouse Model 1MJU_L      SRVEAEDVGVYYQMQHLEYPFTFGAGTKLELK   112 (SEQ ID NO.17)
Human Acceptor ABC66952 SRVEAEDVGVYYCMQALQSPYTFGQGTKLEIK   112 (SEQ ID NO.18)
Hu9D5VLv1               SRVEAEDVGVYYCMQHLEYPLTFGQGTKLEIK   112 (SEQ ID NO.19)
Hu6C1VLv2               SRVEAEDVGVYYCMQHLEYPLTFGQGTKLEIK   112 (SEQ ID NO.20)
Hu9D5VLv3               SRVEAEDVGVYYCMQHLEYPLTFGQGTKLEIK   112 (SEQ ID NO.21)
Hu9D5VLv4               SRVEAEDVGVYYCMQHLEYPLTFGQGTKLEIK   112 (SEQ ID NO.22)
Hu9D5VLv5               SRVEAEDVGVYYCMQHLEYPLTFGQGTKLEIK   112 (SEQ ID NO.23)
```

*FIG. 1B*

| | | | |
|---|---|---|---|
| m14G8VH | EVKLVESGGGLVQPGGSLKLSCAASGFTFSSYTMSWVRQTPE | 42 | |
| Mouse Model 1MQK_H | EVKLQESGGDLVQPGGSLKLSCAASGFTFSSYTMSWVRQTPE | 42 | |
| Human Acceptor AAD30410 | QVQLVQSGGGLVQPGGSLKLSCAASGFTFSSYAMSWVRQTPE | 42 | |
| Human Acceptor AAX82494 | QVQLQESGGGLVKPGGSLKLSCAASGFTFSSYGMSWVRQTPD | 42 | |
| Hu14G8VHv1 | EVKLVESGGGLVQPGGSLKLSCAASGFTFSSYTMSWVRQTPE | 42 | |
| Hu14G8VHv2 | EVQLVESGGGLVQPGGSLKLSCAASGFTFSSYTMSWVRQTPE | 42 | |
| Hu14G8VHv3 | EVQLVESGGGLVQPGGSLKLSCAASGFTFSSYTMSWVRQTPE | 42 | |

| | | | |
|---|---|---|---|
| m14G8VH | KRLELVAEINNSGDTTYYPDTVKGRFTISRDNAKNTLYLQMS | 84 | |
| Mouse Model 1MQK_H | KRLEWVASINNGGRTYYPDTVKGRFTISRDNAKNTLYLQMS | 84 | |
| Human Acceptor AAD30410 | KRLELVAISTDGSFIYYADTVKGRFTISGDNSKNTLYLQMS | 84 | |
| Human Acceptor AAX82494 | KRLEWVATISSGGSYTYYPDSVKGRFTISRDNAKNTLYLQMS | 84 | |
| Hu14G8VHv1 | KRLELVAEINNSGDTTYYPDTVKGRFTISRDNAKNTLYLQMS | 84 | |
| Hu14G8VHv2 | KRLELVAEINNSGDTTYYPDTVKGRFTISRDNAKNTLYLQMS | 84 | |
| Hu14G8VHv3 | KRLELVAEINNSGDTTYYPDTVKGRFTISRDNAKNTLYLQMN | 84 | |

| | | | |
|---|---|---|---|
| m14G8VH | SLKSEDTAMYYCARHYYYGGGYGGWFFDVWGTGTTVTVSS | 124 | (SEQ ID NO.61) |
| Mouse Model 1MQK_H | SLKSEDTAMYYCVRHEYY------YAMDYWGQGTTVTVSS | 118 | (SEQ ID NO.62) |
| Human Acceptor AAD30410 | SLRAEDTAVYYCAKDRGIDATAQVGRFDPWGQGTLVTVSS | 124 | (SEQ ID NO.63) |
| Human Acceptor AAX82494 | SLKSEDTAMYYCARLYYGYRYYF-----DYWGQGTMVTVSS | 120 | (SEQ ID NO.4) |
| Hu14G8VHv1 | SLKSEDTAMYYCARHYYYGGGYGGWFFDVWGTGTLVTVSS | 124 | (SEQ ID NO.64) |
| Hu14G8VHv2 | SLKSEDTAMYYCARHYYYGGGYGGWFFDVWGQGTLVTVSS | 124 | (SEQ ID NO.65) |
| Hu14G8VHv3 | SLRAEDTAVYYCARHYYYGGGYGGWFFDVWGQGTLVTVSS | 124 | (SEQ ID NO.66) |

FIG. 2A

|          | 10         | 20         | 30         | 40         |    |
|----------|------------|------------|------------|------------|----|
| m14G8VL              | DIVMTQAAPSVPVTPGESVSISCRSNKSLLHSNGNTYLYW | 40 |
| Mouse Model 1MJU_L   | DIVMTQAAPSVPVTPGESVSISCRSSKSLLHSNGNTYLYW | 40 |
| Human Acceptor ABA71374 | DIVMTQTPLSLPVTPGEPASISCRSSQSLRHYSGYTYIDW | 40 |
| Human Acceptor ABC66952 | DIVMTQSPLSLPVTPGEPASISCRSNQSLLYSNGYNYLDW | 40 |
| Hu14G8VLv1           | DIVMTQSAPSLPVTPGEPASVSISCRSNKSLLHSNGNTYLYW | 40 |
| Hu14G8VLv2           | DIVMTQSPLSLPVTPGEPASISCRSNKSLLHSNGNTYLYW | 40 |
| Hu14G8VLv3           | DIVMTQSPLSLPVTPGEPASISCRSSKSLLHSNGNTYLYW | 40 |

|          | 50         | 60         | 70         | 80         |    |
|----------|------------|------------|------------|------------|----|
| m14G8VL              | FLQRPGQSPQLLIYRVSNLASGVPDRFSGSGSGTAFTLRI | 80 |
| Mouse Model 1MJU_L   | FLQRPGQSPQLLIYRMSNLASGVPDRFSGSGSGTAFTLRI | 80 |
| Human Acceptor ABA71374 | YLQKPGQSPQVLIYLGSNRASGVPDRFSGSGSGTDFTLKI | 80 |
| Human Acceptor ABC66952 | YLQKPGQSPQLLIYSGSNRASGVPDRFSGSGSGTDFTLKI | 80 |
| Hu14G8VLv1           | FLQKPGQSPQLLIYRVSNLASGVPDRFSGSGSGTAFTLKI | 80 |
| Hu14G8VLv2           | FLQKPGQSPQLLIYRVSNLASGVPDRFSGSGSGTDFTLKI | 80 |
| Hu14G8VLv3           | FLQKPGQSPQLLIYRVSNLASGVPSRFSGSGSGTDFTLKI | 80 |

|          | 90         | 100        | 110        |    |               |
|----------|------------|------------|------------|----|---------------|
| m14G8VL              | SRVEAEDVGVYYCMQHLEYPLTFGAGTKLELKR | 113 | (SEQ ID NO.70) |
| Mouse Model 1MJU_L   | SRVEAEDVGVYYCLQHLEYPFTFGAGTKLELKR | 113 | (SEQ ID NO.71) |
| Human Acceptor ABA71374 | SRVEAEDVGVYYCMQALQTVCSFGQGTKLEIKR | 113 | (SEQ ID NO.72) |
| Human Acceptor ABC66952 | SRVEAEDVGVYYCMQALQSPYTFGQGTKLEIKR | 113 | (SEQ ID NO.73) |
| Hu14G8VLv1           | SRVEAEDVGVYYCMQHLEYPLTFGQGTKLEIKR | 113 | (SEQ ID NO.74) |
| Hu14G8VLv2           | SRVEAEDVGVYYCMQHLEYPLTFGQGTKLEIKR | 113 | (SEQ ID NO.75) |
| Hu14G8VLv3           | SRVEAEDVGVYYCMQHLEYPLTFGQGTKLEIKR | 113 | (SEQ ID NO.76) |

FIG. 2B

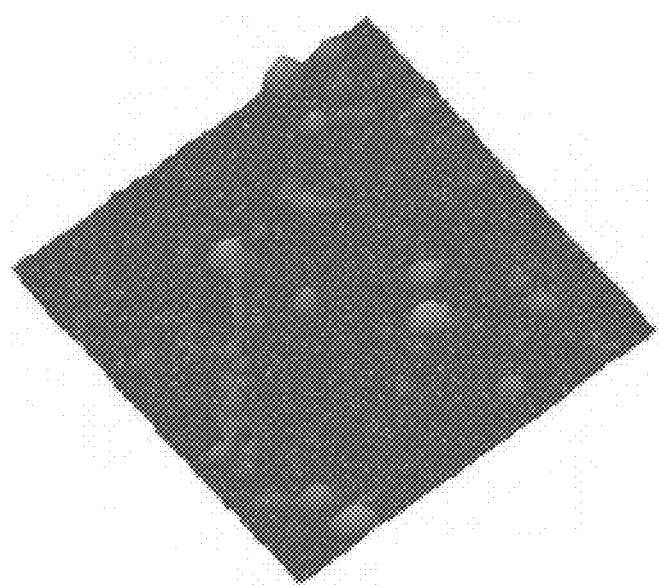
FIG. 8D.1
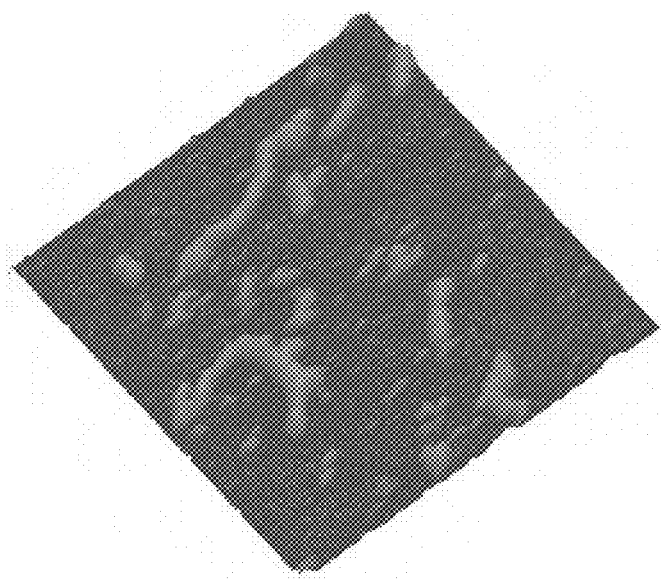
FIG. 8D.2

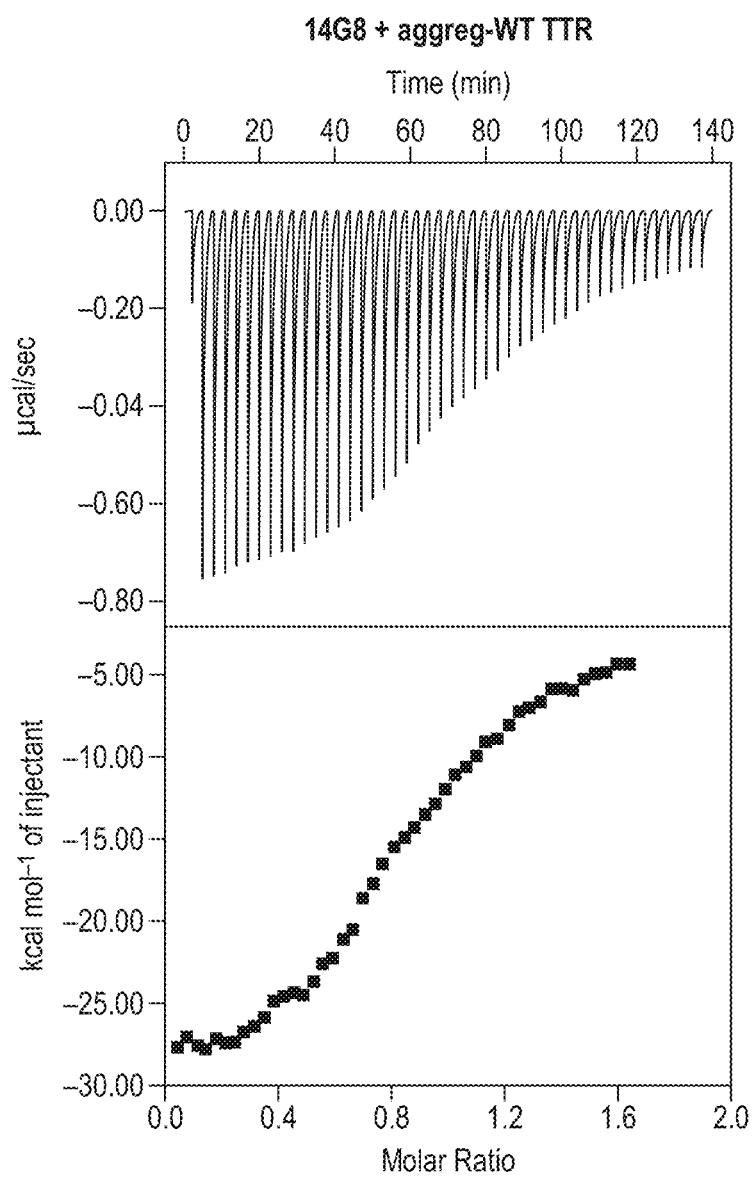
FIG. 9A.1

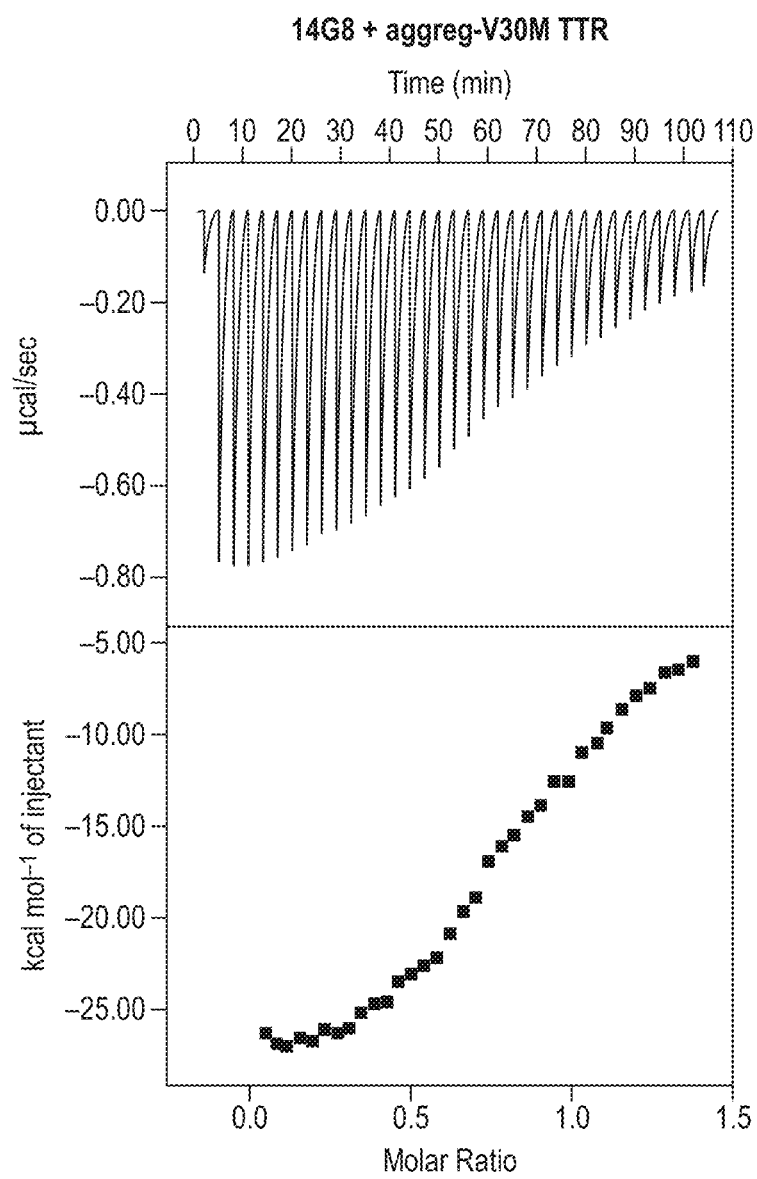
FIG. 9A.2

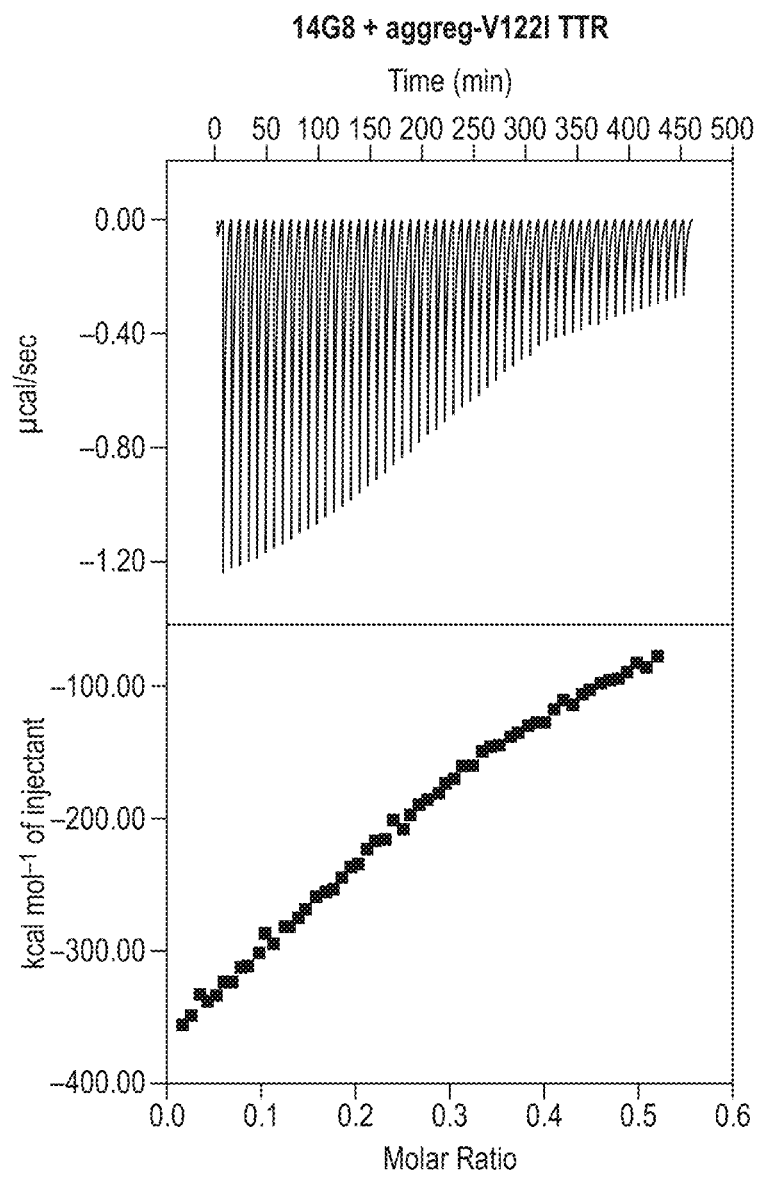
FIG. 9A.3

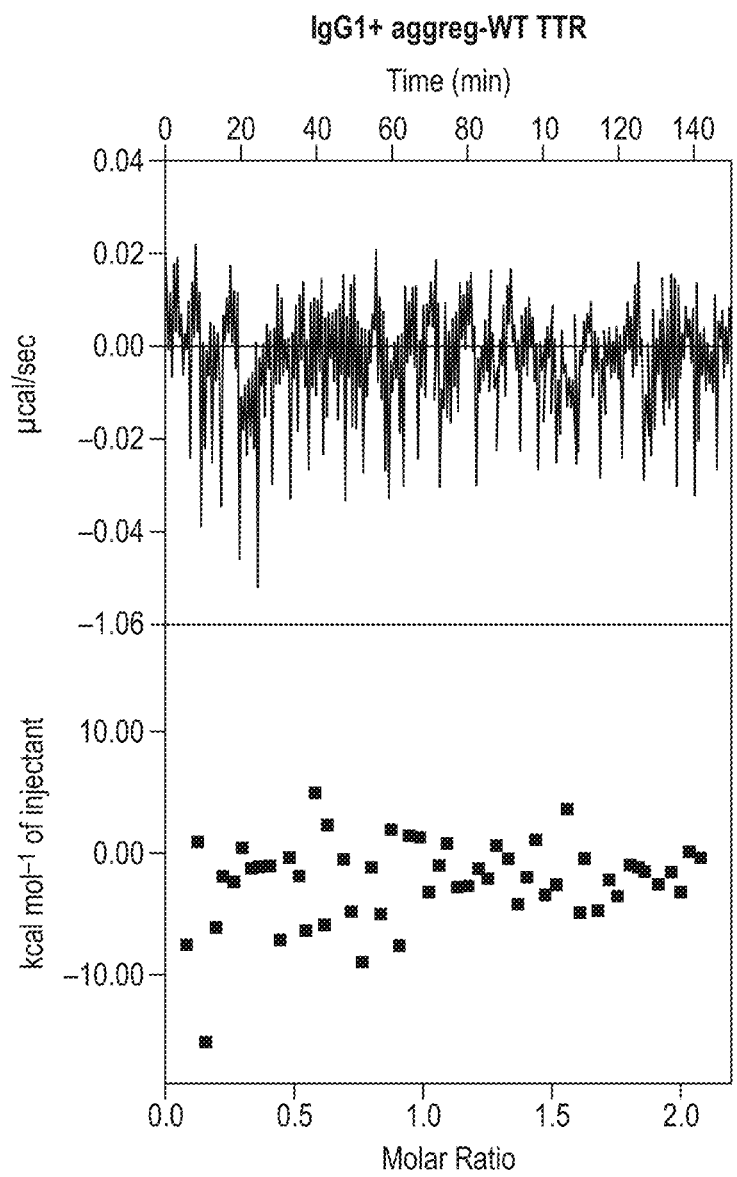
FIG. 9A.4

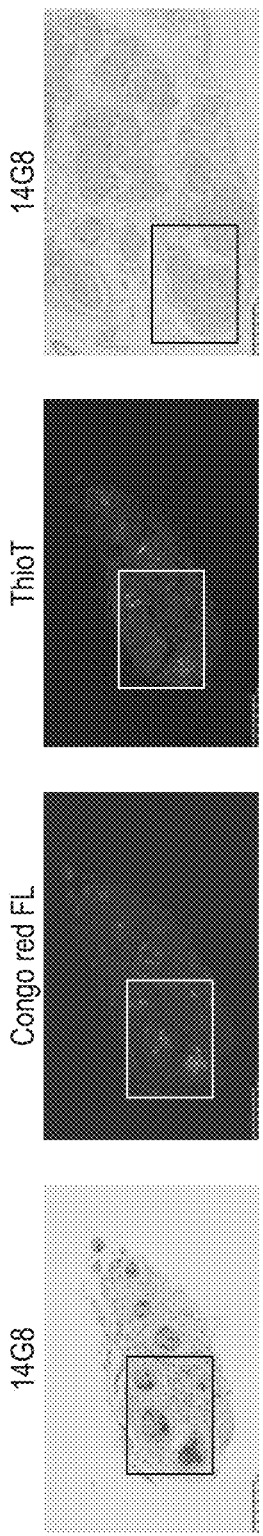
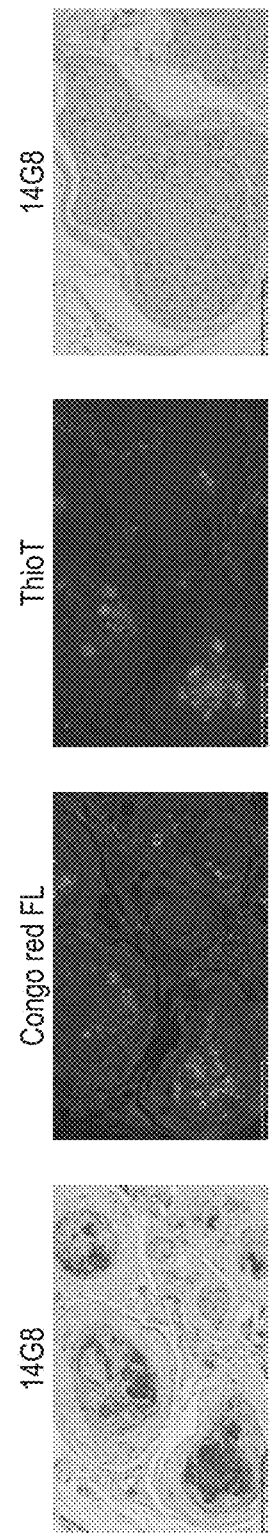
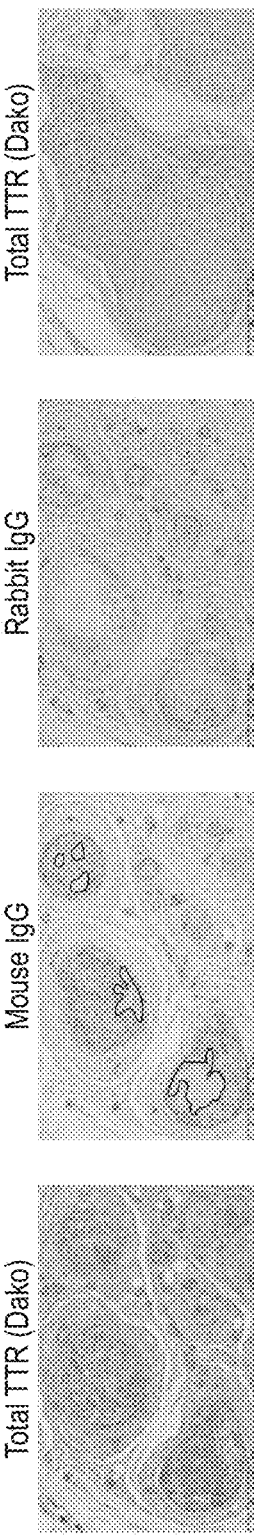
FIG. 10A.1 — 14G8
FIG. 10B.1 — Congo red FL
FIG. 10C.1 — ThioT
FIG. 10G.1 — 14G8
FIG. 10A.2 — 14G8
FIG. 10B.2 — Congo red FL
FIG. 10C.2 — ThioT
FIG. 10G.2 — 14G8
FIG. 10D — Total TTR (Dako)
FIG. 10E — Mouse IgG
FIG. 10F — Rabbit IgG
FIG. 10G.3 — Total TTR (Dako)

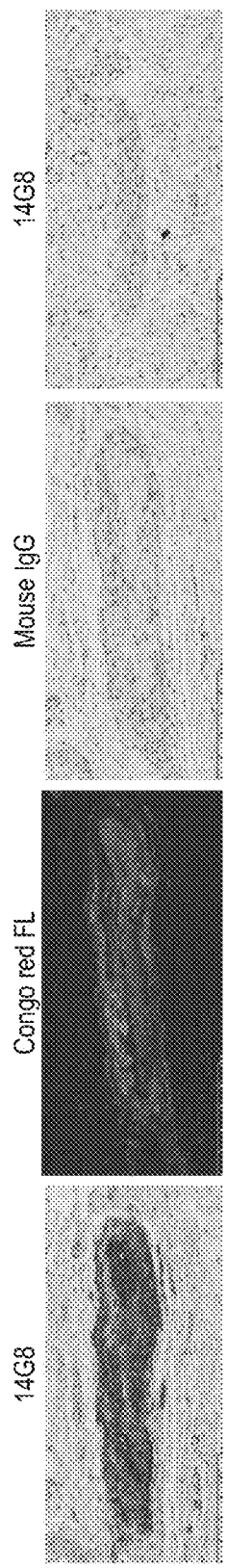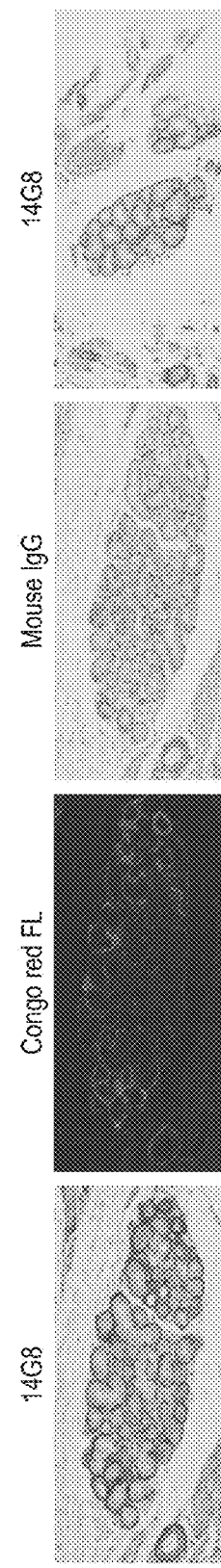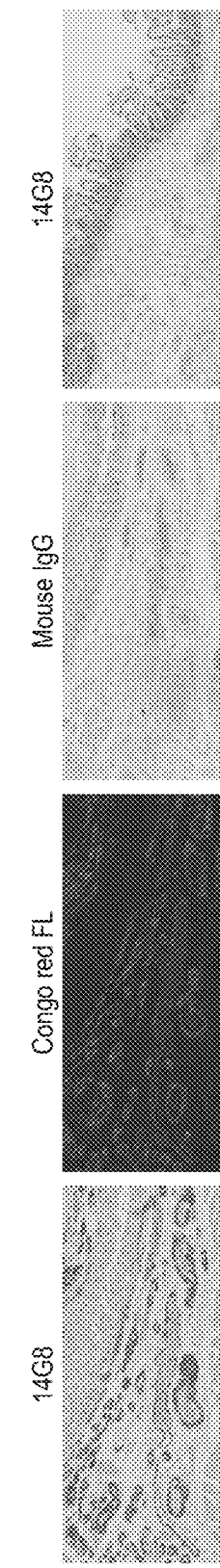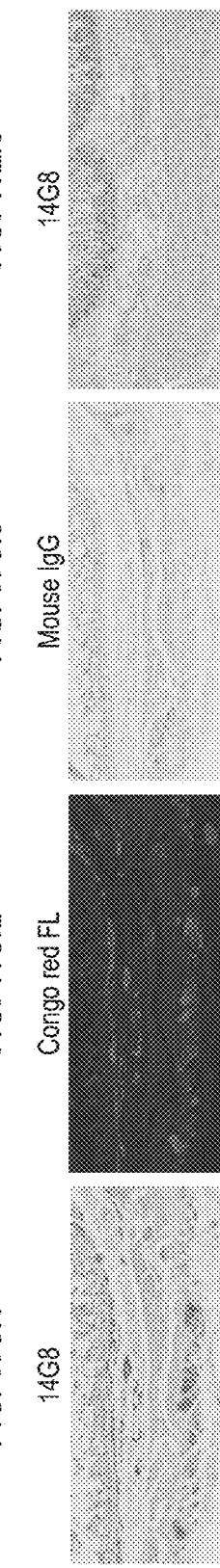

Figure 12A

Humanized 9D5 Vh Regions

| Chothia residue # | Kabat residue # | Linear residue # | FR or CDR | Murine 9D5 VH (SEQ ID NO: 1) | Hu VH Acceptor Fr Acc#BAC02114 (SEQ ID NO: 3) | Hu VH Acceptor Fr Acc#AAX82494 (SEQ ID NO: 4) | Hu9D5 VHv1 (SEQ ID NO: 5) | Hu9D5 VHv2 (SEQ ID NO: 6) | Hu9D5 VHv2b (SEQ ID NO: 7) | Hu9D5 VHv3 (SEQ ID NO: 8) | Hu9D5 VHv3b (SEQ ID NO: 9) | Hu9D5 VHv4 (SEQ ID NO: 10) | Hu9D5 VHv4b (SEQ ID NO: 11) | Hu9D5 VHv5 (SEQ ID NO: 12) |
|---|---|---|---|---|---|---|---|---|---|---|---|---|---|---|
| 1 | 1 | 1 | Fr1 | E | E | Q | E | E | E | E | E | E | E | E |
| 2 | 2 | 2 | Fr1 | V | V | V | V | V | V | V | V | V | V | V |
| 3 | 3 | 3 | Fr1 | K | Q | Q | Q | Q | Q | Q | Q | Q | Q | Q |
| 4 | 4 | 4 | Fr1 | L | L | L | L | L | L | L | L | L | L | L |
| 5 | 5 | 5 | Fr1 | V | V | Q | V | V | V | V | V | V | V | V |
| 6 | 6 | 6 | Fr1 | E | E | E | E | E | E | E | E | E | E | E |
| 7 | 7 | 7 | Fr1 | S | S | S | S | S | S | S | S | S | S | S |
| 8 | 8 | 8 | Fr1 | G | G | G | G | G | G | G | G | G | G | G |
| 9 | 9 | 9 | Fr1 | G | G | G | G | G | G | G | G | G | G | G |
| 10 | 10 | 10 | Fr1 | G | G | G | G | G | G | G | G | G | G | G |
| 11 | 11 | 11 | Fr1 | L | L | L | L | L | L | L | L | L | L | L |
| 12 | 12 | 12 | Fr1 | V | V | V | V | V | V | V | V | V | V | V |
| 13 | 13 | 13 | Fr1 | Q | Q | K | Q | Q | Q | Q | Q | Q | Q | Q |
| 14 | 14 | 14 | Fr1 | P | P | P | P | P | P | P | P | P | P | P |
| 15 | 15 | 15 | Fr1 | G | G | G | G | G | G | G | G | G | G | G |
| 16 | 16 | 16 | Fr1 | G | G | G | G | G | G | G | G | G | G | G |
| 17 | 17 | 17 | Fr1 | S | S | S | S | S | S | S | S | S | S | S |
| 18 | 18 | 18 | Fr1 | L | L | L | L | L | L | L | L | L | L | L |
| 19 | 19 | 19 | Fr1 | K | R | K | R | R | K | R | K | R | K | R |
| 20 | 20 | 20 | Fr1 | L | L | L | L | L | L | L | L | L | L | L |
| 21 | 21 | 21 | Fr1 | S | S | S | S | S | S | S | S | S | S | S |
| 22 | 22 | 22 | Fr1 | C | C | C | C | C | C | C | C | C | C | C |
| 23 | 23 | 23 | Fr1 | A | A | A | A | A | A | A | A | A | A | A |
| 24 | 24 | 24 | Fr1 | A | A | A | A | A | A | A | A | A | A | A |
| 25 | 25 | 25 | Fr1 | S | S | S | S | S | S | S | S | S | S | S |
| 26 | 26 | 26 | CDR-H1 | G | G | G | G | G | G | G | G | G | G | G |
| 27 | 27 | 27 | CDR-H1 | F | F | F | F | F | F | F | F | F | F | F |
| 28 | 28 | 28 | CDR-H1 | T | T | T | T | T | T | T | T | T | T | T |

Figure 12B

Humanized 9D5 Vh Regions

| Chothia residue # | Kabat residue # | Linear residue # | FR or CDR | Murine 9D5 VH (SEQ ID NO: 1) | Hu VH Acceptor Fr Acc#BAC02114 (SEQ ID NO: 3) | Hu VH Acceptor Fr Acc#AAX82494 (SEQ ID NO: 4) | Hu9D5 VHv1 (SEQ ID NO: 5) | Hu9D5 VHv2 (SEQ ID NO: 6) | Hu9D5 VHv2b (SEQ ID NO: 7) | Hu9D5 VHv3 (SEQ ID NO: 8) | Hu9D5 VHv3b (SEQ ID NO: 9) | Hu9D5 VHv4 (SEQ ID NO: 10) | Hu9D5 VHv4b (SEQ ID NO: 11) | Hu9D5 VHv5 (SEQ ID NO: 12) |
|---|---|---|---|---|---|---|---|---|---|---|---|---|---|---|
| 29 | 29 | 29 | CDR-H1 | F | F | F | F | F | F | F | F | F | F | F |
| 30 | 30 | 30 | CDR-H1 | S | S | S | S | S | S | S | S | S | S | S |
| 31 | 31 | 31 | CDR-H1 | S | S | S | S | S | S | S | S | S | S | S |
| 32 | 32 | 32 | CDR-H1 | Y | Y | Y | Y | Y | Y | Y | Y | Y | Y | Y |
| 33 | 33 | 33 | CDR-H1 | T | E | G | T | T | T | T | T | T | T | T |
| 34 | 34 | 34 | CDR-H1 | M | M | M | M | M | M | M | M | M | M | M |
| 35 | 35 | 35 | CDR-H1 | S | N | S | S | S | S | S | S | S | S | S |
| 36 | 36 | 36 | Fr2 | W | W | W | W | W | W | W | W | W | W | W |
| 37 | 37 | 37 | Fr2 | V | V | V | V | V | V | V | V | V | V | V |
| 38 | 38 | 38 | Fr2 | R | R | R | R | R | R | R | R | R | R | R |
| 39 | 39 | 39 | Fr2 | Q | Q | Q | Q | Q | Q | Q | Q | Q | Q | Q |
| 40 | 40 | 40 | Fr2 | T | A | T | A | A | T | A | T | A | A | T |
| 41 | 41 | 41 | Fr2 | P | P | P | P | P | P | P | P | P | P | P |
| 42 | 42 | 42 | Fr2 | E | G | D | G | G | E | G | G | G | G | E |
| 43 | 43 | 43 | Fr2 | K | K | K | K | K | K | K | K | K | K | K |
| 44 | 44 | 44 | Fr2 | R | G | R | G | G | R | G | R | G | R | R |
| 45 | 45 | 45 | Fr2 | L | L | L | L | L | L | L | L | L | L | L |
| 46 | 46 | 46 | Fr2 | E | E | E | E | E | E | E | E | E | E | E |
| 47 | 47 | 47 | Fr2 | L | W | W | L | L | W | L | W | L | L | L |
| 48 | 48 | 48 | Fr2 | V | V | V | V | V | V | V | V | V | V | V |
| 49 | 49 | 49 | Fr2 | A | S | A | A | A | S | A | S | A | A | A |
| 50 | 50 | 50 | CDR-H2 | E | Y | T | E | E | E | E | E | E | E | E |
| 51 | 51 | 51 | CDR-H2 | I | I | I | I | I | I | I | I | I | I | I |
| 52 | 52 | 52 | CDR-H2 | S | T | S | S | S | S | S | S | S | S | S |
| 52A | 52A | 53 | CDR-H2 | N | S | S | N | N | N | N | N | N | N | N |
| 53 | 53 | 54 | CDR-H2 | S | S | G | S | S | S | S | S | S | S | S |
| 54 | 54 | 55 | CDR-H2 | G | G | G | G | G | G | G | G | G | G | G |
| 55 | 55 | 56 | CDR-H2 | D | S | S | D | D | D | D | D | D | D | D |

Figure 12C

Humanized 9D5 Vh Regions

| Chothia residue # | Kabat residue # | Linear residue # | FR or CDR | Murine 9D5 VH (SEQ ID NO: 1) | Hu VH Acceptor Fr Acc#BAC02114 (SEQ ID NO: 3) | Hu VH Acceptor Fr Acc#AAX82494 (SEQ ID NO: 4) | Hu9D5 VHv1 (SEQ ID NO: 5) | Hu9D5 VHv2 (SEQ ID NO: 6) | Hu9D5 VHv2b (SEQ ID NO: 7) | Hu9D5 VHv3 (SEQ ID NO: 8) | Hu9D5 VHv3b (SEQ ID NO: 9) | Hu9D5 VHv4 (SEQ ID NO: 10) | Hu9D5 VHv4b (SEQ ID NO: 11) | Hu9D5 VHv5 (SEQ ID NO: 12) |
|---|---|---|---|---|---|---|---|---|---|---|---|---|---|---|
| 56 | 56 | 57 | CDR-H2 | T | T | Y | T | T | T | T | T | T | T | T |
| 57 | 57 | 58 | CDR-H2 | T | I | T | T | T | T | T | T | T | T | T |
| 58 | 58 | 59 | CDR-H2 | Y | Y | Y | Y | Y | Y | Y | Y | Y | Y | Y |
| 59 | 59 | 60 | CDR-H2 | Y | Y | Y | Y | Y | Y | Y | Y | Y | Y | Y |
| 60 | 60 | 61 | CDR-H2 | P | A | P | P | P | P | P | P | P | P | P |
| 61 | 61 | 62 | CDR-H2 | D | D | D | D | D | D | D | D | D | D | D |
| 62 | 62 | 63 | CDR-H2 | T | S | S | T | T | T | T | T | T | T | T |
| 63 | 63 | 64 | CDR-H2 | V | V | V | V | V | V | V | V | V | V | V |
| 64 | 64 | 65 | CDR-H2 | K | K | K | K | K | K | K | K | K | K | K |
| 65 | 65 | 66 | CDR-H2 | G | G | G | G | G | G | G | G | G | G | G |
| 66 | 66 | 67 | Fr3 | R | R | R | R | R | R | R | R | R | R | R |
| 67 | 67 | 68 | Fr3 | F | F | F | F | F | F | F | F | F | F | F |
| 68 | 68 | 69 | Fr3 | T | T | T | T | T | T | T | T | T | T | T |
| 69 | 69 | 70 | Fr3 | F | I | I | F | F | I | F | I | I | I | I |
| 70 | 70 | 71 | Fr3 | S | S | S | S | S | S | S | S | S | S | S |
| 71 | 71 | 72 | Fr3 | R | R | R | R | R | R | R | R | R | R | R |
| 72 | 72 | 73 | Fr3 | D | D | D | D | D | D | D | D | D | D | D |
| 73 | 73 | 74 | Fr3 | N | N | N | N | N | N | N | N | N | N | N |
| 74 | 74 | 75 | Fr3 | A | A | A | A | A | A | A | A | A | A | A |
| 75 | 75 | 76 | Fr3 | K | K | K | K | K | K | K | K | K | K | K |
| 76 | 76 | 77 | Fr3 | N | N | N | N | N | N | N | N | N | N | N |
| 77 | 77 | 78 | Fr3 | T | S | T | S | S | T | S | T | S | T | T |
| 78 | 78 | 79 | Fr3 | L | L | L | L | L | L | L | L | L | L | L |
| 79 | 79 | 80 | Fr3 | Y | Y | Y | Y | Y | Y | Y | Y | Y | Y | Y |
| 80 | 80 | 81 | Fr3 | L | L | L | L | L | L | L | L | L | L | L |
| 81 | 81 | 82 | Fr3 | Q | Q | Q | Q | Q | Q | Q | Q | Q | Q | Q |
| 82 | 82 | 83 | Fr3 | M | M | M | S | S | M | S | M | S | M | M |
| 82A | 82A | 84 | Fr3 | S | N | S | N | N | S | N | S | N | S | N |

Figure 12D

Humanized 9D5 Vh Regions

| Chothia residue # | Kabat residue # | Linear residue # | FR or CDR | Murine 9D5 VH (SEQ ID NO: 1) | Hu VH Acceptor Fr Acc#BAC02114 (SEQ ID NO: 3) | Hu VH Acceptor Fr Acc#AAX82494 (SEQ ID NO: 4) | Hu9D5 VHv1 (SEQ ID NO: 5) | Hu9D5 VHv2 (SEQ ID NO: 6) | Hu9D5 VHv2b (SEQ ID NO: 7) | Hu9D5 VHv3 (SEQ ID NO: 8) | Hu9D5 VHv3b (SEQ ID NO: 9) | Hu9D5 VHv4 (SEQ ID NO: 10) | Hu9D5 VHv4b (SEQ ID NO: 11) | Hu9D5 VHv5 (SEQ ID NO: 12) |
|---|---|---|---|---|---|---|---|---|---|---|---|---|---|---|
| 82B | 82B | 85 | Fr3 | S | S | S | S | L | S | L | S | L | S | L |
| 82C | 82C | 86 | Fr3 | L | L | L | L | L | L | L | L | L | L | L |
| 83 | 83 | 87 | Fr3 | K | R | K | K | R | K | R | K | R | K | R |
| 84 | 84 | 88 | Fr3 | S | A | S | A | A | S | A | S | A | S | A |
| 85 | 85 | 89 | Fr3 | E | E | E | E | E | E | E | E | E | E | E |
| 86 | 86 | 90 | Fr3 | D | D | D | D | D | D | D | D | D | D | D |
| 87 | 87 | 91 | Fr3 | T | T | T | T | T | T | T | T | T | T | T |
| 88 | 88 | 92 | Fr3 | A | A | A | A | A | A | A | A | A | A | A |
| 89 | 89 | 93 | Fr3 | M | V | M | V | V | M | V | M | V | M | V |
| 90 | 90 | 94 | Fr3 | Y | Y | Y | Y | Y | Y | Y | Y | Y | Y | Y |
| 91 | 91 | 95 | Fr3 | Y | Y | Y | Y | Y | Y | Y | Y | Y | Y | Y |
| 92 | 92 | 96 | Fr3 | C | C | C | C | C | C | C | C | C | C | C |
| 93 | 93 | 97 | Fr3 | A | A | A | A | A | A | A | A | A | A | A |
| 94 | 94 | 98 | Fr3 | R | R | R | R | R | R | R | R | R | R | R |
| 95 | 95 | 99 | CDR-H3 | H | G | L | H | H | H | H | H | H | H | H |
| 96 | 96 | 100 | CDR-H3 | Y | G | Y | Y | Y | Y | Y | Y | Y | Y | Y |
| 97 | 97 | 101 | CDR-H3 | Y | Q | Y | Y | Y | Y | Y | Y | Y | Y | Y |
| 98 | 98 | 102 | CDR-H3 | Y | G | G | Y | Y | Y | Y | Y | Y | Y | Y |
| 99 | 99 | 103 | CDR-H3 | G | S | Y | G | G | G | G | G | G | G | G |
| 100 | 100 | 104 | CDR-H3 | G | R | R | G | G | G | G | G | G | G | G |
| 100A | 100A | 105 | CDR-H3 | G | Y | Y | G | G | G | G | G | G | G | G |
| 100B | 100B | 106 | CDR-H3 | Y | Y | Y | Y | Y | Y | Y | Y | Y | Y | Y |
| 100C | 100C | 107 | CDR-H3 | G | Y | F | G | G | G | G | G | G | G | G |
| 100D | 100D | 108 | CDR-H3 | G | Y | - | G | G | G | G | G | G | G | G |
| 100E | 100E | 109 | CDR-H3 | W | Y | - | W | W | W | W | W | W | W | W |
| 100F | 100F | 110 | CDR-H3 | F | G | - | F | F | F | F | F | F | F | F |
| 100G | 100G | 111 | CDR-H3 | F | M | - | F | F | F | F | F | F | F | F |
| 101 | 101 | 112 | CDR-H3 | D | D | D | D | D | D | D | D | D | D | D |

Figure 12E

Humanized 9D5 Vh Regions

| Chothia residue # | Kabat residue # | Linear residue # | FR or CDR | Murine 9D5 VH (SEQ ID NO: 1) | Hu VH Acceptor Fr Acc#BAC02214 (SEQ ID NO: 3) | Hu VH Acceptor Fr Acc#AAX82494 (SEQ ID NO: 4) | Hu9D5 VHv1 (SEQ ID NO: 5) | Hu9D5 VHv2 (SEQ ID NO: 6) | Hu9D5 VHv2b (SEQ ID NO: 7) | Hu9D5 VHv3 (SEQ ID NO: 8) | Hu9D5 VHv3b (SEQ ID NO: 9) | Hu9D5 VHv4 (SEQ ID NO: 10) | Hu9D5 VHv4b (SEQ ID NO: 11) | Hu9D5 VHv5 (SEQ ID NO: 12) |
|---|---|---|---|---|---|---|---|---|---|---|---|---|---|---|
| 102 | 102 | 113 | CDR-H3 | V | V | Y | V | V | V | V | V | V | V | V |
| 103 | 103 | 114 | Fr4 | W | W | W | W | W | W | W | W | W | W | W |
| 104 | 104 | 115 | Fr4 | G | G | G | G | G | G | G | G | G | G | G |
| 105 | 105 | 116 | Fr4 | T | Q | Q | Q | Q | Q | Q | Q | Q | Q | Q |
| 106 | 106 | 117 | Fr4 | G | G | G | G | G | G | G | G | G | G | G |
| 107 | 107 | 118 | Fr4 | T | T | T | T | T | T | T | T | T | T | T |
| 108 | 108 | 119 | Fr4 | T | T | M | T | T | L | T | L | T | L | T |
| 109 | 109 | 120 | Fr4 | V | V | V | V | V | V | V | V | V | V | V |
| 110 | 110 | 121 | Fr4 | T | T | T | T | T | T | T | T | T | T | T |
| 111 | 111 | 122 | Fr4 | V | V | V | V | V | V | V | V | V | V | V |
| 112 | 112 | 123 | Fr4 | S | S | S | S | S | S | S | S | S | S | S |
| 113 | 113 | 124 | Fr4 | S | S | S | S | S | S | S | S | S | S | S |

Figure 13A

Humanized 9D5 Vk Regions

| Chothia residue # | Kabat residue # | Linear residue # | FR or CDR | Murine 9D5 VL (SEQ ID NO: 16) | Hu VL Acceptor Fr Acc#ABC66952 (SEQ ID NO: 18) | Hu9D5 VLv1 (SEQ ID NO: 19) | Hu9D5 VLv2 (SEQ ID NO: 20) | Hu9D5 VLv3 (SEQ ID NO: 21) | Hu9D5 VLv4 (SEQ ID NO: 22) | Hu9D5 VLv5 (SEQ ID NO: 23) |
|---|---|---|---|---|---|---|---|---|---|---|
| 1 | 1 | 1 | Fr1 | D | D | D | D | D | D | D |
| 2 | 2 | 2 | Fr1 | I | I | I | I | I | I | I |
| 3 | 3 | 3 | Fr1 | V | V | V | V | V | V | V |
| 4 | 4 | 4 | Fr1 | M | M | M | M | M | M | M |
| 5 | 5 | 5 | Fr1 | T | T | T | T | T | T | T |
| 6 | 6 | 6 | Fr1 | Q | Q | Q | Q | Q | Q | Q |
| 7 | 7 | 7 | Fr1 | A | S | S | S | S | S | S |
| 8 | 8 | 8 | Fr1 | A | P | P | P | P | A | A |
| 9 | 9 | 9 | Fr1 | P | L | L | L | L | P | P |
| 10 | 10 | 10 | Fr1 | S | S | S | S | S | S | S |
| 11 | 11 | 11 | Fr1 | V | L | L | L | L | L | L |
| 12 | 12 | 12 | Fr1 | P | P | P | P | P | P | P |
| 13 | 13 | 13 | Fr1 | V | V | V | V | V | V | V |
| 14 | 14 | 14 | Fr1 | T | T | T | T | T | T | T |
| 15 | 15 | 15 | Fr1 | P | P | P | P | P | P | P |
| 16 | 16 | 16 | Fr1 | G | G | G | G | G | G | G |
| 17 | 17 | 17 | Fr1 | E | E | E | E | E | E | E |
| 18 | 18 | 18 | Fr1 | S | P | P | P | P | P | S |
| 19 | 19 | 19 | Fr1 | V | A | A | A | A | V | V |
| 20 | 20 | 20 | Fr1 | S | S | S | S | S | S | S |
| 21 | 21 | 21 | Fr1 | I | I | I | I | I | I | I |
| 22 | 22 | 22 | Fr1 | S | S | S | S | S | S | S |
| 23 | 23 | 23 | Fr1 | C | C | C | C | C | C | C |
| 24 | 24 | 24 | CDR-L1 | R | R | R | R | R | R | R |
| 25 | 25 | 25 | CDR-L1 | S | S | S | S | S | S | S |
| 26 | 26 | 26 | CDR-L1 | S | N | S | S | S | S | S |
| 27 | 27 | 27 | CDR-L1 | K | Q | K | K | K | K | K |
| 27A | 27A | 28 | CDR-L1 | S | S | S | S | S | S | S |
| 27B | 27B | 29 | CDR-L1 | L | L | L | L | L | L | L |
| 27C | 27C | 30 | CDR-L1 | L | L | L | L | L | L | L |

Figure 13B

Humanized 9D5 Vk Regions

| Chothia residue # | Kabat residue # | Linear residue # | FR or CDR | Murine 9D5 VL (SEQ ID NO: 16) | Hu VL Acceptor Fr Acc#ABC66952 (SEQ ID NO: 18) | Hu9D5 VLv1 (SEQ ID NO: 19) | Hu9D5 VLv2 (SEQ ID NO: 20) | Hu9D5 VLv3 (SEQ ID NO: 21) | Hu9D5 VLv4 (SEQ ID NO: 22) | Hu9D5 VLv5 (SEQ ID NO: 23) |
|---|---|---|---|---|---|---|---|---|---|---|
| 27D | 27D | 31 | CDR-L1 | H | Y | H | H | H | H | H |
| 27E | 27E | 32 | CDR-L1 | S | S | S | S | S | S | S |
| 28 | 28 | 33 | CDR-L1 | N | N | N | N | N | N | N |
| 29 | 29 | 34 | CDR-L1 | G | G | G | G | G | G | G |
| 30 | 30 | 35 | CDR-L1 | N | Y | N | N | N | N | N |
| 31 | 31 | 36 | CDR-L1 | T | N | T | T | T | T | T |
| 32 | 32 | 37 | CDR-L1 | Y | Y | Y | Y | Y | Y | Y |
| 33 | 33 | 38 | CDR-L1 | L | L | L | L | L | L | L |
| 34 | 34 | 39 | CDR-L1 | Y | D | Y | Y | Y | Y | Y |
| 35 | 35 | 40 | Fr2 | W | W | W | W | W | W | W |
| 36 | 36 | 41 | Fr2 | F | Y | F | Y | Y | F | F |
| 37 | 37 | 42 | Fr2 | L | L | L | L | L | L | L |
| 38 | 38 | 43 | Fr2 | Q | Q | Q | Q | Q | Q | Q |
| 39 | 39 | 44 | Fr2 | R | K | K | K | K | R | R |
| 40 | 40 | 45 | Fr2 | P | P | P | P | P | P | P |
| 41 | 41 | 46 | Fr2 | G | G | G | G | G | G | G |
| 42 | 42 | 47 | Fr2 | Q | Q | Q | Q | Q | Q | Q |
| 43 | 43 | 48 | Fr2 | S | S | S | S | S | S | S |
| 44 | 44 | 49 | Fr2 | P | P | P | P | P | P | P |
| 45 | 45 | 50 | Fr2 | Q | Q | Q | Q | Q | Q | Q |
| 46 | 46 | 51 | Fr2 | L | L | L | L | L | L | L |
| 47 | 47 | 52 | Fr2 | L | L | L | L | L | L | L |
| 48 | 48 | 53 | Fr2 | I | I | I | I | I | I | I |
| 49 | 49 | 54 | Fr2 | Y | Y | Y | Y | Y | Y | Y |
| 50 | 50 | 55 | CDR-L2 | R | S | R | R | R | R | R |
| 51 | 51 | 56 | CDR-L2 | V | G | V | V | V | V | V |
| 52 | 52 | 57 | CDR-L2 | S | S | S | S | S | S | S |
| 53 | 53 | 58 | CDR-L2 | N | N | N | N | N | N | N |
| 54 | 54 | 59 | CDR-L2 | L | R | L | L | L | L | L |
| 55 | 55 | 60 | CDR-L2 | A | A | A | A | A | A | A |

Figure 13C

Humanized 9D5 Vk Regions

| Chothia residue # | Kabat residue # | Linear residue # | FR or CDR | Murine 9D5 VL (SEQ ID NO: 16) | Hu VL Acceptor Fr Acc#ABC66952 (SEQ ID NO: 18) | Hu9D5 VLv1 (SEQ ID NO: 19) | Hu9D5 VLv2 (SEQ ID NO: 20) | Hu9D5 VLv3 (SEQ ID NO: 21) | Hu9D5 VLv4 (SEQ ID NO: 22) | Hu9D5 VLv5 (SEQ ID NO: 23) |
|---|---|---|---|---|---|---|---|---|---|---|
| 56 | 56 | 61 | CDR-L2 | S | S | S | S | S | S | S |
| 57 | 57 | 62 | Fr3 | G | G | G | G | G | G | G |
| 58 | 58 | 63 | Fr3 | V | V | V | V | V | V | V |
| 59 | 59 | 64 | Fr3 | P | P | P | P | P | P | P |
| 60 | 60 | 65 | Fr3 | D | D | D | D | S | S | S |
| 61 | 61 | 66 | Fr3 | R | R | R | R | R | R | R |
| 62 | 62 | 67 | Fr3 | F | F | F | F | F | F | F |
| 63 | 63 | 68 | Fr3 | S | S | S | S | S | S | S |
| 64 | 64 | 69 | Fr3 | G | G | G | G | G | G | G |
| 65 | 65 | 70 | Fr3 | S | S | S | S | S | S | S |
| 66 | 66 | 71 | Fr3 | G | G | G | G | G | G | G |
| 67 | 67 | 72 | Fr3 | S | S | S | S | S | S | S |
| 68 | 68 | 73 | Fr3 | G | G | G | G | G | G | G |
| 69 | 69 | 74 | Fr3 | T | T | T | T | T | T | T |
| 70 | 70 | 75 | Fr3 | A | D | D | D | D | A | A |
| 71 | 71 | 76 | Fr3 | F | F | F | F | F | F | F |
| 72 | 72 | 77 | Fr3 | T | T | T | T | T | T | T |
| 73 | 73 | 78 | Fr3 | L | L | L | L | L | L | L |
| 74 | 74 | 79 | Fr3 | R | K | K | K | K | R | R |
| 75 | 75 | 80 | Fr3 | I | I | I | I | I | I | I |
| 76 | 76 | 81 | Fr3 | S | S | S | S | S | S | S |
| 77 | 77 | 82 | Fr3 | R | R | R | R | R | R | R |
| 78 | 78 | 83 | Fr3 | V | V | V | V | V | V | V |
| 79 | 79 | 84 | Fr3 | E | E | E | E | E | E | E |
| 80 | 80 | 85 | Fr3 | A | A | A | A | A | A | A |
| 81 | 81 | 86 | Fr3 | E | E | E | E | E | E | E |
| 82 | 82 | 87 | Fr3 | D | D | D | D | D | D | D |
| 83 | 83 | 88 | Fr3 | V | V | V | V | V | V | V |
| 84 | 84 | 89 | Fr3 | G | G | G | G | G | G | G |
| 85 | 85 | 90 | Fr3 | V | V | V | V | V | V | V |

Figure 13D

Humanized 9D5 Vk Regions

| Chothia residue # | Kabat residue # | Linear residue # | FR or CDR | Murine 9D5 VL (SEQ ID NO: 16) | Hu VL Acceptor Fr Acc#ABC66952 (SEQ ID NO: 18) | Hu9D5 VLv1 (SEQ ID NO: 19) | Hu9D5 VLv2 (SEQ ID NO: 20) | Hu9D5 VLv3 (SEQ ID NO: 21) | Hu9D5 VLv4 (SEQ ID NO: 22) | Hu9D5 VLv5 (SEQ ID NO: 23) |
|---|---|---|---|---|---|---|---|---|---|---|
| 86 | 86 | 91 | Fr3 | Y | Y | Y | Y | Y | Y | Y |
| 87 | 87 | 92 | Fr3 | Y | Y | Y | Y | Y | Y | Y |
| 88 | 88 | 93 | Fr3 | C | C | C | C | C | C | C |
| 89 | 89 | 94 | CDR-L3 | M | M | M | M | M | M | M |
| 90 | 90 | 95 | CDR-L3 | Q | Q | Q | Q | Q | Q | Q |
| 91 | 91 | 96 | CDR-L3 | H | A | H | H | H | H | H |
| 92 | 92 | 97 | CDR-L3 | I | I | I | I | I | I | I |
| 93 | 93 | 98 | CDR-L3 | E | Q | E | E | E | E | E |
| 94 | 94 | 99 | CDR-L3 | Y | S | Y | Y | Y | Y | Y |
| 95 | 95 | 100 | CDR-L3 | P | P | P | P | P | P | P |
| 96 | 96 | 101 | CDR-L3 | L | Y | L | L | L | L | L |
| 97 | 97 | 102 | CDR-L3 | T | T | T | T | T | T | T |
| 98 | 98 | 103 | Fr4 | F | F | F | F | F | F | F |
| 99 | 99 | 104 | Fr4 | G | G | G | G | G | G | G |
| 100 | 100 | 105 | Fr4 | A | Q | Q | Q | Q | Q | Q |
| 101 | 101 | 106 | Fr4 | G | G | G | G | G | G | G |
| 102 | 102 | 107 | Fr4 | T | T | T | T | T | T | T |
| 103 | 103 | 108 | Fr4 | K | K | K | K | K | K | K |
| 104 | 104 | 109 | Fr4 | L | L | L | L | L | L | L |
| 105 | 105 | 110 | Fr4 | E | E | E | E | E | E | E |
| 106 | 106 | 111 | Fr4 | L | I | I | I | I | I | I |
| 107 | 107 | 112 | Fr4 | K | K | K | K | K | K | K |

Figure 14A

Humanized 14G8 Vh Regions

| Chothia residue # | Kabat residue # | Linear residue # | FR or CDR | Murine 14G8 VH (SEQ ID NO: 61) | Hu VH Acceptor Fr Acc# AAD30410.1 (SEQ ID NO: 63) | Hu VH Acceptor Fr Acc# AAX82494.1 (SEQ ID NO: 4) | Hu14G8 VHv1 (SEQ ID NO: 64) | Hu14G8 VHv2 (SEQ ID NO: 65) | Hu14G8 VHv3 (SEQ ID NO: 66) |
|---|---|---|---|---|---|---|---|---|---|
| 1 | 1 | 1 | Fr1 | E | Q | Q | E | E | E |
| 2 | 2 | 2 | Fr1 | V | V | V | V | V | V |
| 3 | 3 | 3 | Fr1 | K | Q | Q | K | Q | Q |
| 4 | 4 | 4 | Fr1 | L | L | L | L | L | L |
| 5 | 5 | 5 | Fr1 | V | V | Q | V | V | V |
| 6 | 6 | 6 | Fr1 | E | Q | E | E | E | E |
| 7 | 7 | 7 | Fr1 | S | S | S | S | S | S |
| 8 | 8 | 8 | Fr1 | G | G | G | G | G | G |
| 9 | 9 | 9 | Fr1 | G | G | G | G | G | G |
| 10 | 10 | 10 | Fr1 | G | G | G | G | G | G |
| 11 | 11 | 11 | Fr1 | L | L | L | L | L | L |
| 12 | 12 | 12 | Fr1 | V | V | V | V | V | V |
| 13 | 13 | 13 | Fr1 | Q | Q | K | Q | Q | Q |
| 14 | 14 | 14 | Fr1 | P | P | P | P | P | P |
| 15 | 15 | 15 | Fr1 | G | G | G | G | G | G |
| 16 | 16 | 16 | Fr1 | G | G | G | G | G | G |
| 17 | 17 | 17 | Fr1 | S | S | S | S | S | S |
| 18 | 18 | 18 | Fr1 | L | R | L | L | L | L |
| 19 | 19 | 19 | Fr1 | K | K | K | K | K | K |
| 20 | 20 | 20 | Fr1 | L | L | L | L | L | L |
| 21 | 21 | 21 | Fr1 | S | S | S | S | S | S |
| 22 | 22 | 22 | Fr1 | C | C | C | C | C | C |
| 23 | 23 | 23 | Fr1 | A | A | A | A | A | A |
| 24 | 24 | 24 | Fr1 | A | A | A | A | A | A |
| 25 | 25 | 25 | Fr1 | S | S | S | S | S | S |
| 26 | 26 | 26 | Fr1 | G | G | G | G | G | G |
| 27 | 27 | 27 | Fr1 | F | F | F | F | F | F |
| 28 | 28 | 28 | Fr1 | T | T | T | T | T | T |
| 29 | 29 | 29 | Fr1 | F | F | F | F | F | F |
| 30 | 30 | 30 | Fr1 | S | S | S | S | S | S |

Figure 14B

Humanized 14G8 Vh Regions

| Chothia residue # | Kabat residue # | Linear residue # | FR or CDR | Murine 14G8 VH (SEQ ID NO: 61) | Hu VH Acceptor Fr Acc# AAD30410.1 (SEQ ID NO: 63) | Hu VH Acceptor Fr Acc# AAX82494.1 (SEQ ID NO: 4) | Hu14G8 VHv1 (SEQ ID NO: 64) | Hu14G8 VHv2 (SEQ ID NO: 65) | Hu14G8 VHv3 (SEQ ID NO: 66) |
|---|---|---|---|---|---|---|---|---|---|
| 31 | 31 | 31 | CDR-H1 | S | S | S | S | S | S |
| 32 | 32 | 32 | CDR-H1 | Y | Y | Y | Y | Y | Y |
| 33 | 33 | 33 | CDR-H1 | T | A | G | T | T | T |
| 34 | 34 | 34 | CDR-H1 | M | M | M | M | M | M |
| 35 | 35 | 35 | CDR-H1 | S | S | S | S | S | S |
| 36 | 36 | 36 | Fr2 | W | W | W | W | W | W |
| 37 | 37 | 37 | Fr2 | V | V | V | V | V | V |
| 38 | 38 | 38 | Fr2 | R | R | R | R | R | R |
| 39 | 39 | 39 | Fr2 | Q | Q | Q | Q | Q | Q |
| 40 | 40 | 40 | Fr2 | T | T | T | T | T | T |
| 41 | 41 | 41 | Fr2 | P | P | P | P | P | P |
| 42 | 42 | 42 | Fr2 | E | E | D | E | E | E |
| 43 | 43 | 43 | Fr2 | K | K | K | K | K | K |
| 44 | 44 | 44 | Fr2 | R | R | R | R | R | R |
| 45 | 45 | 45 | Fr2 | L | L | L | L | L | L |
| 46 | 46 | 46 | Fr2 | E | E | E | E | E | E |
| 47 | 47 | 47 | Fr2 | L | W | W | L | L | L |
| 48 | 48 | 48 | Fr2 | V | V | V | V | V | V |
| 49 | 49 | 49 | Fr2 | A | A | A | A | A | A |
| 50 | 50 | 50 | CDR-H2 | E | A | T | E | E | E |
| 51 | 51 | 51 | CDR-H2 | I | I | I | I | I | I |
| 52 | 52 | 52 | CDR-H2 | N | S | S | N | N | N |
| 52A | 52A | 53 | CDR-H2 | N | T | S | N | N | N |
| 53 | 53 | 54 | CDR-H2 | S | D | G | S | S | S |
| 54 | 54 | 55 | CDR-H2 | G | G | G | G | G | G |
| 55 | 55 | 56 | CDR-H2 | D | S | S | D | D | D |
| 56 | 56 | 57 | CDR-H2 | T | F | Y | T | T | T |
| 57 | 57 | 58 | CDR-H2 | T | I | T | T | T | T |
| 58 | 58 | 59 | CDR-H2 | Y | Y | Y | Y | Y | Y |
| 59 | 59 | 60 | CDR-H2 | Y | Y | Y | Y | Y | Y |

Figure 14C

Humanized 14G8 Vh Regions

| Chothia residue # | Kabat residue # | Linear residue # | FR or CDR | Murine 14G8 VH (SEQ ID NO: 61) | Hu VH Acceptor Fr Acc# AAD30410.1 (SEQ ID NO: 63) | Hu VH Acceptor Fr Acc# AAX82494.1 (SEQ ID NO: 4) | Hu14G8 VHv1 (SEQ ID NO: 64) | Hu14G8 VHv2 (SEQ ID NO: 65) | Hu14G8 VHv3 (SEQ ID NO: 66) |
|---|---|---|---|---|---|---|---|---|---|
| 60 | 60 | 61 | CDR-H2 | P | A | P | P | P | P |
| 61 | 61 | 62 | CDR-H2 | D | D | D | D | D | D |
| 62 | 62 | 63 | CDR-H2 | T | T | S | T | T | T |
| 63 | 63 | 64 | CDR-H2 | V | V | V | V | V | V |
| 64 | 64 | 65 | CDR-H2 | K | K | K | K | K | K |
| 65 | 65 | 66 | CDR-H2 | G | G | G | G | G | G |
| 66 | 66 | 67 | Fr3 | R | R | R | R | R | R |
| 67 | 67 | 68 | Fr3 | F | F | F | F | F | F |
| 68 | 68 | 69 | Fr3 | T | T | T | T | T | T |
| 69 | 69 | 70 | Fr3 | I | I | I | I | I | I |
| 70 | 70 | 71 | Fr3 | S | S | S | S | S | S |
| 71 | 71 | 72 | Fr3 | R | G | R | R | R | R |
| 72 | 72 | 73 | Fr3 | D | D | D | D | D | D |
| 73 | 73 | 74 | Fr3 | N | N | N | N | N | N |
| 74 | 74 | 75 | Fr3 | A | S | A | A | A | A |
| 75 | 75 | 76 | Fr3 | K | K | K | K | K | K |
| 76 | 76 | 77 | Fr3 | N | N | N | N | N | N |
| 77 | 77 | 78 | Fr3 | T | T | T | T | T | T |
| 78 | 78 | 79 | Fr3 | L | L | L | L | L | L |
| 79 | 79 | 80 | Fr3 | Y | Y | Y | Y | Y | Y |
| 80 | 80 | 81 | Fr3 | L | L | L | L | L | L |
| 81 | 81 | 82 | Fr3 | Q | Q | Q | Q | Q | Q |
| 82 | 82 | 83 | Fr3 | M | M | M | M | M | M |
| 82A | 82A | 84 | Fr3 | S | N | S | S | S | N |
| 82B | 82B | 85 | Fr3 | S | S | S | S | S | S |
| 82C | 82C | 86 | Fr3 | L | L | L | L | L | L |
| 83 | 83 | 87 | Fr3 | K | R | K | K | K | R |
| 84 | 84 | 88 | Fr3 | S | A | S | S | S | A |
| 85 | 85 | 89 | Fr3 | E | E | E | E | E | E |
| 86 | 86 | 90 | Fr3 | D | D | D | D | D | D |

Figure 14D

Humanized 14G8 Vh Regions

| Chothia residue # | Kabat residue # | Linear residue # | FR or CDR | Murine 14G8 VH (SEQ ID NO: 61) | Hu VH Acceptor Fr Acc# AAD30410.1 (SEQ ID NO: 63) | Hu VH Acceptor Fr Acc# AAX82494.1 (SEQ ID NO: 4) | Hu14G8 VHv1 (SEQ ID NO: 64) | Hu14G8 VHv2 (SEQ ID NO: 65) | Hu14G8 VHv3 (SEQ ID NO: 66) |
|---|---|---|---|---|---|---|---|---|---|
| 87 | 87 | 91 | Fr3 | T | T | T | T | T | T |
| 88 | 88 | 92 | Fr3 | A | A | A | A | A | A |
| 89 | 89 | 93 | Fr3 | M | V | M | M | M | V |
| 90 | 90 | 94 | Fr3 | Y | Y | Y | Y | Y | Y |
| 91 | 91 | 95 | Fr3 | Y | Y | Y | Y | Y | Y |
| 92 | 92 | 96 | Fr3 | C | C | C | C | C | C |
| 93 | 93 | 97 | Fr3 | A | A | A | A | A | A |
| 94 | 94 | 98 | Fr3 | R | K | R | R | R | R |
| 95 | 95 | 99 | CDR-H3 | H | D | L | H | H | H |
| 96 | 96 | 100 | CDR-H3 | Y | R | Y | Y | Y | Y |
| 97 | 97 | 101 | CDR-H3 | Y | G | Y | Y | Y | Y |
| 98 | 98 | 102 | CDR-H3 | Y | I | G | Y | Y | Y |
| 99 | 99 | 103 | CDR-H3 | G | D | Y | G | G | G |
| 100 | 100 | 104 | CDR-H3 | G | A | R | G | G | G |
| 100A | 100A | 105 | CDR-H3 | G | T | Y | G | G | G |
| 100B | 100B | 106 | CDR-H3 | Y | A | Y | Y | Y | Y |
| 100C | 100C | 107 | CDR-H3 | G | Q | F | G | G | G |
| 100D | 100D | 108 | CDR-H3 | G | V | - | G | G | G |
| 100E | 100E | 109 | CDR-H3 | W | G | - | W | W | W |
| 100F | 100F | 110 | CDR-H3 | F | R | - | F | F | F |
| 100G | 100G | 111 | CDR-H3 | F | F | - | F | F | F |
| 101 | 101 | 112 | CDR-H3 | D | D | D | D | D | D |
| 102 | 102 | 113 | CDR-H3 | V | P | Y | V | V | V |
| 103 | 103 | 114 | Fr4 | W | W | W | W | W | W |
| 104 | 104 | 115 | Fr4 | G | G | G | G | G | G |
| 105 | 105 | 116 | Fr4 | T | Q | Q | T | Q | Q |
| 106 | 106 | 117 | Fr4 | G | G | G | G | G | G |
| 107 | 107 | 118 | Fr4 | T | T | T | T | T | T |
| 108 | 108 | 119 | Fr4 | T | L | M | L | L | L |
| 109 | 109 | 120 | Fr4 | V | V | V | V | V | V |

Figure 14E
Humanized 14G8 Vh Regions

| Chothia residue # | Kabat residue # | Linear residue # | FR or CDR | Murine 14G8 VH (SEQ ID NO: 61) | Hu VH Acceptor Fr Acc# AAD30410.1 (SEQ ID NO: 63) | Hu VH Acceptor Fr Acc# AAX82494.1 (SEQ ID NO: 4) | Hu14G8 VHv1 (SEQ ID NO: 64) | Hu14G8 VHv2 (SEQ ID NO: 65) | Hu14G8 VHv3 (SEQ ID NO: 66) |
|---|---|---|---|---|---|---|---|---|---|
| 110 | 110 | 121 | Fr4 | T | T | T | T | T | T |
| 111 | 111 | 122 | Fr4 | V | V | V | V | V | V |
| 112 | 112 | 123 | Fr4 | S | S | S | S | S | S |
| 113 | 113 | 124 | Fr4 | S | S | S | S | S | S |

Figure 15A

Humanized 14G8 Vk Regions

| Chothia residue # | Kabat residue # | Linear residue # | FR or CDR | Murine 14G8 VL (SEQ ID NO: 70) | Hu VL Acceptor Fr Acc# ABA71374.1 (SEQ ID NO: 72) | Hu VL Acceptor Fr Acc# ABC66952.1 (SEQ ID NO: 73) | Hu14G8 VLv1 (SEQ ID NO: 74) | Hu14G8 VLv2 (SEQ ID NO: 75) | Hu14G8 VLv3 (SEQ ID NO: 76) |
|---|---|---|---|---|---|---|---|---|---|
| 1 | 1 | 1 | Fr1 | D | D | D | D | D | D |
| 2 | 2 | 2 | Fr1 | I | I | I | I | I | I |
| 3 | 3 | 3 | Fr1 | V | V | V | V | V | V |
| 4 | 4 | 4 | Fr1 | M | M | M | M | M | M |
| 5 | 5 | 5 | Fr1 | T | T | T | T | T | T |
| 6 | 6 | 6 | Fr1 | Q | Q | Q | Q | Q | Q |
| 7 | 7 | 7 | Fr1 | A | T | S | S | S | S |
| 8 | 8 | 8 | Fr1 | A | P | P | A | P | P |
| 9 | 9 | 9 | Fr1 | P | L | L | P | L | L |
| 10 | 10 | 10 | Fr1 | S | S | S | S | S | S |
| 11 | 11 | 11 | Fr1 | V | L | L | L | L | L |
| 12 | 12 | 12 | Fr1 | P | P | P | P | P | P |
| 13 | 13 | 13 | Fr1 | V | V | V | V | V | V |
| 14 | 14 | 14 | Fr1 | T | T | T | T | T | T |
| 15 | 15 | 15 | Fr1 | P | P | P | P | P | P |
| 16 | 16 | 16 | Fr1 | G | G | G | G | G | G |
| 17 | 17 | 17 | Fr1 | E | E | E | E | E | E |
| 18 | 18 | 18 | Fr1 | S | S | P | S | P | P |
| 19 | 19 | 19 | Fr1 | V | A | A | V | A | A |
| 20 | 20 | 20 | Fr1 | S | S | S | S | S | S |
| 21 | 21 | 21 | Fr1 | I | I | I | I | I | I |
| 22 | 22 | 22 | Fr1 | S | S | S | S | S | S |
| 23 | 23 | 23 | Fr1 | C | C | C | C | C | C |
| 24 | 24 | 24 | CDR-L1 | R | R | R | R | R | R |
| 25 | 25 | 25 | CDR-L1 | S | S | S | S | S | S |
| 26 | 26 | 26 | CDR-L1 | N | S | N | N | N | S |
| 27 | 27 | 27 | CDR-L1 | K | Q | Q | K | K | K |
| 27A | 27A | 28 | CDR-L1 | S | S | S | S | S | S |
| 27B | 27B | 29 | CDR-L1 | L | L | L | L | L | L |
| 27C | 27C | 30 | CDR-L1 | L | R | L | L | L | L |

Figure 15B

Humanized 14G8 Vk Regions

| Chothia residue # | Kabat residue # | Linear residue # | FR or CDR | Murine 14G8 VL (SEQ ID NO: 70) | Hu VL Acceptor Fr Acc# ABA71374.1 (SEQ ID NO: 72) | Hu VL Acceptor Fr Acc# ABC66952.1 (SEQ ID NO: 73) | Hu14G8 VLv1 (SEQ ID NO: 74) | Hu14G8 VLv2 (SEQ ID NO: 75) | Hu14G8 VLv3 (SEQ ID NO: 76) |
|---|---|---|---|---|---|---|---|---|---|
| 27D | 27D | 31 | CDR-L1 | H | H | Y | H | H | H |
| 27E | 27E | 32 | CDR-L1 | S | Y | S | S | S | S |
| 27F | 27F | 33 | CDR-L1 | N | S | N | N | N | N |
| 28 | 28 | 34 | CDR-L1 | G | G | G | G | G | G |
| 29 | 29 | 35 | CDR-L1 | N | Y | Y | N | N | N |
| 30 | 30 | 36 | CDR-L1 | T | T | N | T | T | T |
| 31 | 31 | 37 | CDR-L1 | Y | Y | Y | Y | Y | Y |
| 32 | 32 | 38 | CDR-L1 | L | I | L | L | L | L |
| 33 | 33 | 39 | CDR-L1 | Y | D | D | Y | Y | Y |
| 34 | 34 |  | CDR-L1 |  |  |  |  |  |  |
| 35 | 35 | 40 | Fr2 | W | W | W | W | W | W |
| 36 | 36 | 41 | Fr2 | F | Y | Y | F | F | F |
| 37 | 37 | 42 | Fr2 | L | L | L | L | L | L |
| 38 | 38 | 43 | Fr2 | Q | Q | Q | Q | Q | Q |
| 39 | 39 | 44 | Fr2 | R | K | K | K | K | K |
| 40 | 40 | 45 | Fr2 | P | P | P | P | P | P |
| 41 | 41 | 46 | Fr2 | G | G | G | G | G | G |
| 42 | 42 | 47 | Fr2 | Q | Q | Q | Q | Q | Q |
| 43 | 43 | 48 | Fr2 | S | S | S | S | S | S |
| 44 | 44 | 49 | Fr2 | P | P | P | P | P | P |
| 45 | 45 | 50 | Fr2 | Q | Q | Q | Q | Q | Q |
| 46 | 46 | 51 | Fr2 | L | V | L | L | L | L |
| 47 | 47 | 52 | Fr2 | L | L | L | L | L | L |
| 48 | 48 | 53 | Fr2 | I | I | I | I | I | I |
| 49 | 49 | 54 | Fr2 | Y | Y | Y | Y | Y | Y |
| 50 | 50 | 55 | CDR-L2 | R | L | S | R | R | R |
| 51 | 51 | 56 | CDR-L2 | V | G | G | V | V | V |
| 52 | 52 | 57 | CDR-L2 | S | S | S | S | S | S |
| 53 | 53 | 58 | CDR-L2 | N | N | N | N | N | N |
| 54 | 54 | 59 | CDR-L2 | L | R | R | L | L | L |

Figure 15C

Humanized 14G8 Vk Regions

| Chothia residue # | Kabat residue # | Linear residue # | FR or CDR | Murine 14G8 VL (SEQ ID NO: 70) | Hu VL Acceptor Fr Acc# ABA71374.1 (SEQ ID NO: 72) | Hu VL Acceptor Fr Acc# ABC66952.1 (SEQ ID NO: 73) | Hu14G8 VLv1 (SEQ ID NO: 74) | Hu14G8 VLv2 (SEQ ID NO: 75) | Hu14G8 VLv3 (SEQ ID NO: 76) |
|---|---|---|---|---|---|---|---|---|---|
| 55 | 55 | 60 | CDR-L2 | A | A | A | A | A | A |
| 56 | 56 | 61 | CDR-L2 | S | S | S | S | S | S |
| 57 | 57 | 62 | Fr3 | G | G | G | G | G | G |
| 58 | 58 | 63 | Fr3 | V | V | V | V | V | V |
| 59 | 59 | 64 | Fr3 | P | P | P | P | P | P |
| 60 | 60 | 65 | Fr3 | D | D | D | D | D | S |
| 61 | 61 | 66 | Fr3 | R | R | R | R | R | R |
| 62 | 62 | 67 | Fr3 | F | F | F | F | F | F |
| 63 | 63 | 68 | Fr3 | S | S | S | S | S | S |
| 64 | 64 | 69 | Fr3 | G | G | G | G | G | G |
| 65 | 65 | 70 | Fr3 | S | S | S | S | S | S |
| 66 | 66 | 71 | Fr3 | G | G | G | G | G | G |
| 67 | 67 | 72 | Fr3 | S | S | S | S | S | S |
| 68 | 68 | 73 | Fr3 | G | G | G | G | G | G |
| 69 | 69 | 74 | Fr3 | T | T | T | T | T | T |
| 70 | 70 | 75 | Fr3 | A | D | D | A | D | D |
| 71 | 71 | 76 | Fr3 | F | F | F | F | F | F |
| 72 | 72 | 77 | Fr3 | T | T | T | T | T | T |
| 73 | 73 | 78 | Fr3 | L | L | L | L | L | L |
| 74 | 74 | 79 | Fr3 | R | K | K | K | K | K |
| 75 | 75 | 80 | Fr3 | I | I | I | I | I | I |
| 76 | 76 | 81 | Fr3 | S | S | S | S | S | S |
| 77 | 77 | 82 | Fr3 | R | R | R | R | R | R |
| 78 | 78 | 83 | Fr3 | V | V | V | V | V | V |
| 79 | 79 | 84 | Fr3 | E | E | E | E | E | E |
| 80 | 80 | 85 | Fr3 | A | A | A | A | A | A |
| 81 | 81 | 86 | Fr3 | E | E | E | E | E | E |
| 82 | 82 | 87 | Fr3 | D | D | D | D | D | D |
| 83 | 83 | 88 | Fr3 | V | V | V | V | V | V |
| 84 | 84 | 89 | Fr3 | G | G | G | G | G | G |

Figure 15D
Humanized 14G8 Vk Regions

| Chothia residue # | Kabat residue # | Linear residue # | FR or CDR | Murine 14G8 VL (SEQ ID NO: 70) | Hu VL Acceptor Fr Acc# ABA71374.1 (SEQ ID NO: 72) | Hu VL Acceptor Fr Acc# ABC66952.1 (SEQ ID NO: 73) | Hu14G8 VLv1 (SEQ ID NO: 74) | Hu14G8 VLv2 (SEQ ID NO: 75) | Hu14G8 VLv3 (SEQ ID NO: 76) |
|---|---|---|---|---|---|---|---|---|---|
| 85 | 85 | 90 | Fr3 | V | V | V | V | V | V |
| 86 | 86 | 91 | Fr3 | Y | Y | Y | Y | Y | Y |
| 87 | 87 | 92 | Fr3 | Y | Y | Y | Y | Y | Y |
| 88 | 88 | 93 | Fr3 | C | C | C | C | C | C |
| 89 | 89 | 94 | CDR-L3 | M | M | M | M | M | M |
| 90 | 90 | 95 | CDR-L3 | Q | Q | Q | Q | Q | Q |
| 91 | 91 | 96 | CDR-L3 | H | A | A | H | H | H |
| 92 | 92 | 97 | CDR-L3 | L | L | L | L | L | L |
| 93 | 93 | 98 | CDR-L3 | E | Q | Q | E | E | E |
| 94 | 94 | 99 | CDR-L3 | Y | T | S | Y | Y | Y |
| 95 | 95 | 100 | CDR-L3 | P | V | P | P | P | P |
| 96 | 96 | 101 | CDR-L3 | L | C | Y | L | L | L |
| 97 | 97 | 102 | CDR-L3 | T | S | T | T | T | T |
| 98 | 98 | 103 | Fr4 | F | F | F | F | F | F |
| 99 | 99 | 104 | Fr4 | G | G | G | G | G | G |
| 100 | 100 | 105 | Fr4 | A | Q | Q | Q | Q | Q |
| 101 | 101 | 106 | Fr4 | G | G | G | G | G | G |
| 102 | 102 | 107 | Fr4 | T | T | T | T | T | T |
| 103 | 103 | 108 | Fr4 | K | K | K | K | K | K |
| 104 | 104 | 109 | Fr4 | L | L | L | L | L | L |
| 105 | 105 | 110 | Fr4 | E | E | E | E | E | E |
| 106 | 106 | 111 | Fr4 | L | I | I | I | I | I |
| 106A | 106A | 112 | Fr4 | K | K | K | K | K | K |
| 107 | 107 | 113 | Fr4 | R | R | R | R | R | R |

ANTI-TRANSTHYRETIN ANTIBODIES

CROSS REFERENCE TO RELATED APPLICATIONS

This application is a continuation in part of U.S. application Ser. No. 15/009,662 filed Jan. 28, 2016, which claims the benefit of U.S. Provisional Application No. 62/109,002 filed Jan. 28, 2015 and U.S. Provisional Application No. 62/266,556 filed Dec. 11, 2015, each of which is incorporated by reference in its entirety.

REFERENCE TO A SEQUENCE LISTING

This application includes an electronic sequence listing in a file named 477656_SEQLST.TXT, created on Jul. 1, 2016, and containing 135,122 bytes, which is hereby incorporated by reference in its entirety for all purposes.

BACKGROUND

Several diseases are thought to be caused by the abnormal folding and aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Transthyretin (TTR) is one of the many proteins that are known to misfold and aggregate (e.g., undergo amyloidogenesis). Transthyretin-related amyloidosis encompasses two forms of disease: familial disease arising from misfolding of a mutated or variant TTR, and a sporadic, non-genetic disease caused by misaggregation of wild-type TTR. The process of TTR amyloidogenesis can cause pathology in the nervous system and/or heart, as well as in other tissues.

SUMMARY OF THE CLAIMED INVENTION

The invention provides antibodies that bind to transthyretin and comprise three heavy chain CDRs and three light chain CDRs substantially from antibody 14G8. Some antibodies comprise three Kabat heavy chain CDRs and three Kabat light chain CDRs of the antibody 14G8, except that positions H52 and L26 can each be N or S. Some antibodies comprise three Kabat heavy chain CDRs and three Kabat light chain CDRs of the antibody 14G8. Optionally, CDR-H1 is a composite Kabat-Chothia CDR of the antibody 14G8. Some antibodies comprise three Kabat heavy chain CDRs of the antibody 9D5. Optionally, CDR-H1 is a composite Kabat-Chothia CDR of the antibody 9D5.

Some antibodies bind to the same epitope on transthyretin as 9D5 or 14G8 and comprises three light chain CDRs and three heavy chain CDRs, wherein: (a) each CDR has at least 90% sequence identity to a corresponding CDR from the heavy and light chain variable regions of 9D5; or (b) each CDR has at least 90% sequence identity to a corresponding CDR from the heavy and light chain variable regions of 14G8, except that position L26 can be N or S. Some antibodies comprise: (a) the three heavy chain CDRs and the three light chain CDRs of 9D5; or (b) the three heavy chain CDRs and the three light chain CDRs of 14G8, except that position L26 can be N or S. In some antibodies, the three heavy chain CDRs and the three light chain CDRs of 9D5 are SEQ ID NOS: 13-15 and 24-26, respectively. In some antibodies, the three heavy chain CDRs and the three light chain CDRs of 14G8 are SEQ ID NOS: 67-69 and 77-79, respectively, except that position L26 can be N or S.

Any of the above antibodies can be a monoclonal antibody. Any of the above antibodies can be a chimeric, humanized, veneered, or human antibody. Any of the above antibodies can have human IgG1 isotype, human IgG2 isotype, or human IgG4 isotype.

The invention further provides humanized or chimeric antibodies of mouse antibody that specifically binds to transthyretin, wherein the mouse antibody is characterized by a mature heavy chain variable region of SEQ ID NO: 61 and a mature light chain variable region of SEQ ID NO: 70, except that position H52 can be S or N, position H69 can be F or I, position L26 can be S or N, and the R at position L107 is optional. Optionally, the antibodies are a humanized or chimeric 9D5 or 14G8 antibody that specifically binds to transthyretin, wherein 9D5 is a mouse antibody characterized by a mature heavy chain variable region of SEQ ID NO: 1 and a mature light chain variable region of SEQ ID NO: 16, and 14G8 is a mouse antibody characterized by a mature heavy chain variable region of SEQ ID NO: 61 and a mature light chain variable region of SEQ ID NO: 70. Optionally, the humanized antibodies comprise: (a) a humanized mature heavy chain variable region comprising the three heavy chain CDRs of 9D5 and a humanized mature light chain variable region comprising the three light chain CDRs of 9D5; or (b) a humanized mature heavy chain variable region comprising the three heavy chain CDRs of 14G8 and a humanized mature light chain variable region comprising the three light chain CDRs of 14G8, except that position L26 can be N or S. Optionally, the three heavy chain CDRs and the three light chain CDRs of 9D5 are SEQ ID NOS: 13-15 and 24-26, respectively. Optionally, the three heavy chain CDRs and the three light chain CDRs of 14G8 are SEQ ID NOS: 67-69 and 77-79, respectively, except that position L26 can be N or S. Optionally, any differences in CDRs of the mature heavy chain variable region and mature light chain variable region from SEQ ID NOS: 1 and 16, respectively, reside in positions H60-H65. Optionally, any differences in CDRs of the mature heavy chain variable region and mature light chain variable region from SEQ ID NOS: 61 and 70, respectively, reside in positions H60-H65, except that position L26 can be N or S.

Optionally, the humanized antibody comprises a humanized mature heavy chain variable region having an amino acid sequence at least 90% identical to any one of SEQ ID NOS: 5-12 and a humanized mature light chain variable region having an amino acid sequence at least 90% identical to any one of SEQ ID NOS: 19-23, except that position H19 can be R or K, position H40 can be A or T, position H44 can be G or R, position H49 can be S or A, position H77 can be S or T, position H82a can be N or S, position H83 can be R or K, position H84 can be A or S, and position H89 can be V or M. Optionally, at least one of the following positions is occupied by the amino acid as specified: position H42 is occupied by E, position H47 is occupied by L, position H69 is occupied by F, position H82 is occupied by S, position H82b is occupied by L, position H108 is occupied by L, position L8 is occupied by A, position L9 is occupied by P, position L18 is occupied by S, position L19 is occupied by V, position L36 is occupied by F, position L39 is occupied by R, position L60 is occupied by S, position L70 is occupied by A, and position L74 is occupied by R. Optionally, positions H47, H69, and H82 are occupied by L, F, and S, respectively. Optionally, positions H47, H69, H82, and H82b are occupied by L, F, S, and L, respectively. Optionally, positions H42, H47, and H108 are occupied by E, L, and L, respectively. Optionally, positions H69, H82, and H82b are occupied by F, S, and L, respectively. Optionally, positions H47 and H108 are each occupied by L. Optionally, positions H82 and H82b are occupied by S and L, respectively. Optionally, positions H42, H47, and H82b are occupied by E, L, and L, respectively. Optionally, position L36 is occupied by F. Optionally, position L60 is occupied by S. Optionally, positions L8, L9, L19, L36, L39, L60, L70, and L74 are occupied by A, P, V, F, R, S, A, and R, respectively. Optionally, positions L8, L9, L18, L19, L36, L39, L60, L70, and L74 are occupied by A, P, S, V, F, R, S, A, and R, respectively.

Optionally, the humanized antibody comprises a mature heavy chain variable region having an amino acid sequence at least 95% identical to any one of SEQ ID NOS: 5-12 and a mature light chain variable region having an amino acid sequence at least 95% identical to any one of SEQ ID NOS: 19-23, except that position H19 can be R or K, position H40 can be A or T, position H44 can be G or R, position H49 can be S or A, position H77 can be S or T, position H82a can be N or S, position H83 can be R or K, position H84 can be A or S, and position H89 can be V or M. Optionally, the humanized antibody comprises a mature heavy chain variable region having an amino acid sequence at least 98% identical to any one of SEQ ID NOS: 5-12 and a mature light chain variable region having an amino acid sequence at least 98% identical to any one of SEQ ID NOS: 19-23, except that position H19 can be R or K, position H40 can be A or T, position H44 can be G or R, position H49 can be S or A, position H77 can be S or T, position H82a can be N or S, position H83 can be R or K, position H84 can be A or S, and position H89 can be V or M. Optionally, the mature heavy chain variable region has an amino acid sequence of any one of SEQ ID NO: 5-12 and the mature light chain variable region has an amino acid sequence of any one of SEQ ID NO: 19-23. In some antibodies, the mature heavy chain variable region has an amino acid sequence of SEQ ID NO: 11 and the mature light chain variable region has an amino acid sequence of SEQ ID NO: 19.

Optionally, the humanized antibody comprises a humanized mature heavy chain variable region having an amino acid sequence at least 90% identical to any one of SEQ ID NOS: 64-66 and a humanized mature light chain variable region having an amino acid sequence at least 90% identical to any one of SEQ ID NOS: 74-76, except that position H82a can be N or S, position H83 can be R or K, position H84 can be A or S, position H89 can be V or M, and position L18 can be S or P. Optionally, at least one of the following positions is occupied by the amino acid as specified: position H1 is occupied by E, position H47 is occupied by L, and position L36 is occupied by F. Optionally, positions H1 and H47 are occupied by E and L, respectively. Optionally, position L36 is occupied by F. Optionally, at least one of the following positions is occupied by the amino acid as specified: position H3 is occupied by K, position H105 is occupied by T, position L8 is occupied by A, position L9 is occupied by P, position L19 is occupied by V, position L26 is occupied by S, position L60 is occupied by S, and position L70 is occupied by A. Optionally, positions H3 and H105 are occupied by K and T, respectively. Optionally, positions L8, L9, L19, and L70 are occupied by A, P, V, and A, respectively. Optionally, positions L26 and L60 are each occupied by S.

Optionally, the humanized antibody comprises a mature heavy chain variable region having an amino acid sequence at least 95% identical to any one of SEQ ID NOS: 64-66 and a mature light chain variable region having an amino acid sequence at least 95% identical to any one of SEQ ID NOS: 74-76, except that position H82a can be N or S, position H83 can be R or K, position H84 can be A or S, position H89 can be V or M, and position L18 can be S or P. Optionally, the humanized antibody comprises a mature heavy chain variable region having an amino acid sequence at least 98% identical to any one of SEQ ID NOS: 64-66 and a mature light chain variable region having an amino acid sequence at least 98% identical to any one of SEQ ID NOS: 74-76, except that position H82a can be N or S, position H83 can be R or K, position H84 can be A or S, position H89 can be V or M, and position L18 can be S or P. Optionally, the mature heavy chain variable region has an amino acid sequence of any one of SEQ ID NOS: 64-66, and the mature light chain variable region has an amino acid sequence of any one of SEQ ID NOS: 74-76. In some antibodies, the mature heavy chain variable region has an amino acid sequence of SEQ ID NO: 65 and the mature light chain variable region has an amino acid sequence of SEQ ID NO: 76.

Any of the above antibodies can be an intact antibody, a binding fragment, a single-chain antibody, a Fab, or a Fab'$_2$ fragment. In any of the above antibodies, the mature light chain variable region can be fused to a light chain constant region and the mature heavy chain variable region can be fused to a heavy chain constant region. Optionally, the heavy chain constant region is a mutant form of a natural human heavy chain constant region which has reduced binding to a Fcy receptor relative to the natural human heavy chain constant region. Optionally, the heavy chain constant region is of IgG1 isotype. Optionally, the mature heavy chain variable region is fused to a heavy chain constant region having the sequence of SEQ ID NO: 103 and/or the mature light chain variable region is fused to a light chain constant region having the sequence of SEQ ID NO: 104 or 105.

The invention further provides pharmaceutical compositions comprising any of the above antibodies and a pharmaceutically acceptable carrier.

The invention further provides nucleic acids encoding the heavy chain and/or light chain of any of the above antibodies, such as any one of SEQ ID NOS: 40, 42, 44-56, 87, 89, 91-96, and 106-108.

The invention further provides a recombinant expression vector comprising a nucleic acid as described above, and a host cell transformed with the recombinant expression vector.

The invention further provides a method of humanizing an antibody, the method comprising: (a) selecting one or more acceptor antibodies; (b) identifying the amino acid residues of the mouse antibody to be retained; (c) synthesizing a nucleic acid encoding a humanized heavy chain comprising CDRs of the mouse antibody heavy chain and a nucleic acid encoding a humanized light chain comprising CDRs of the mouse antibody light chain; and (d) expressing the nucleic acids in a host cell to produce a humanized antibody; wherein the mouse antibody is 9D5 or 14G8, wherein 9D5 is characterized by a mature heavy chain variable region of SEQ ID NO: 1 and a mature light chain variable region of SEQ ID NO: 16, and 14G8 is characterized by a mature heavy chain variable region of SEQ ID NO: 61 and a mature light chain variable region of SEQ ID NO: 70.

The invention further provides a method of producing a humanized, chimeric, or veneered antibody, the method comprising: (a) culturing cells transformed with nucleic acids encoding the heavy and light chains of the antibody, so that the cells secrete the antibody; and (b) purifying the antibody from cell culture media; wherein the antibody is a humanized, chimeric, or veneered form of 9D5 or 14G8.

The invention further provides a method of producing a cell line producing a humanized, chimeric, or veneered antibody, the method comprising: (a) introducing a vector encoding heavy and light chains of an antibody and a selectable marker into cells; (b) propagating the cells under conditions to select for cells having increased copy number of the vector; (c) isolating single cells from the selected cells; and (d) banking cells cloned from a single cell selected based on yield of antibody; wherein the antibody is a humanized, chimeric, or veneered form of 9D5 or 14G8. Optionally, the method further comprises propagating the cells under selective conditions and screening for cell lines naturally expressing and secreting at least 100 mg/L/$10^6$ cells/24 h.

The invention further provides a method of inhibiting or reducing aggregation of transthyretin in a subject having or at risk of developing a transthyretin-mediated amyloidosis, comprising administering to the subject an effective regime of any of the above antibodies, thereby inhibiting or reducing aggregation of transthyretin in the subject.

The invention further provides a method of inhibiting or reducing transthyretin fibril formation in a subject having or at risk of developing a transthyretin-mediated amyloidosis, comprising administering to the subject an effective regime of any of the above antibodies, thereby inhibiting or reducing transthyretin accumulation in the subject.

The invention further provides a method of reducing transthyretin deposits in a subject having or at risk of developing a transthyretin-mediated amyloidosis, comprising administering to the subject an effective regime of any of the above antibodies, thereby reducing transthyretin deposits in the subject.

The invention further provides a method of clearing aggregated transthyretin in a subject having or at risk of developing a transthyretin-mediated amyloidosis, comprising administering to the subject an effective regime of any of the above antibodies, thereby clearing aggregated transthyretin from the subject relative to a subject having or at risk of developing a transthyretin-mediated amyloidosis who has not received the antibody.

The invention further provides a method of stabilizing a non-toxic conformation of transthyretin in a subject having or at risk of developing a transthyretin-mediated amyloidosis, comprising administering to the subject an effective regime of any of the above antibodies, thereby stabilizing a non-toxic conformation of transthyretin in the subject.

The invention further provides a method of treating or effecting prophylaxis of a transthyretin-mediated amyloidosis in a subject, comprising administering to the subject an effective regime of any of the above antibodies.

The invention further provides a method of delaying the onset of a transthyretin-mediated amyloidosis in a subject, comprising administering to the subject an effective regime of any of the above antibodies.

The invention further provides a method of diagnosing a transthyretin-mediated amyloidosis in a subject, comprising contacting a biological sample from the subject with an effective amount of any of the above antibodies. Optionally, the method further comprises detecting the binding of antibody to transthyretin, wherein the presence of bound antibody indicates the subject has a transthyretin-mediated amyloidosis. Optionally, the method further comprises comparing binding of the antibody to the biological sample with binding of the antibody to a control sample, whereby increased binding of the antibody to the biological sample relative to the control sample indicates the subject has a transthyretin-mediated amyloidosis. Optionally, the biological sample and the control sample comprise cells of the same tissue origin. Optionally, the biological sample and/or the control sample is blood, serum, plasma, or solid tissue. Optionally, the solid tissue is from the heart, peripheral nervous system, autonomic nervous system, kidneys, eyes, or gastrointestinal tract.

In any of the above methods, the transthyretin-mediated amyloidosis can be associated with a condition selected from any of cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, macular degeneration and a ligament or tendon disorder.

The invention further provides a method of treating a subject having or at risk of any of cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, macular degeneration and a ligament or tendon disorder, the method comprising administering to the subject an effective regime of the antibody of any one of claims.

In any of the above methods, the transthyretin-mediated amyloidosis can optionally be a familial transthyretin amyloidosis or a sporadic transthyretin amyloidosis. Optionally, the familial transthyretin amyloidosis is familial amyloid cardiomyopathy (FAC), familial amyloid polyneuropathy (FAP), or central nervous system selective amyloidosis (CNSA). Optionally, the sporadic transthyretin amyloidosis is senile systemic amyloidosis (SSA) or senile cardiac amyloidosis (SCA). In any of the above methods, the transthyretin-mediated amyloidosis can optionally be associated with amyloid accumulation in the heart, peripheral nervous system, autonomic nervous system, kidneys, eyes, or gastrointestinal tract of the subject.

The invention further provides a method of detecting the presence or absence of transthyretin deposits in a subject, comprising contacting a biological sample from the subject suspected of comprising the amyloid accumulation with an effective amount of any of the above antibodies. Optionally, the method further comprises detecting the binding of antibody to transthyretin, wherein detection of bound antibody indicates the presence of transthyretin deposits. Optionally, the method further comprises comparing binding of the antibody to the biological sample with binding of the antibody to a control sample, whereby increased binding of the antibody to the biological sample relative to the control sample indicates the subject has a transthyretin-mediated amyloidosis. Optionally, the biological sample and the control sample comprise cells of the same tissue origin. Optionally, the biological sample and/or the control sample is blood, serum, plasma, or solid tissue. Optionally, the solid tissue is from the heart, peripheral nervous system, autonomic nervous system, kidneys, eyes, or gastrointestinal tract.

The invention further provides a method of determining a level of transthyretin deposits in a subject, comprising administering any of the above antibodies and detecting the presence of bound antibody in the subject. Optionally, the presence of bound antibody is determined by positron emission tomography (PET).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A.1 & 1A.2 depict an alignment of heavy chain variable regions of the mouse 9D5 antibody, mouse model antibodies, human acceptor antibodies, and humanized versions of the 9D5 antibody. The CDRs as defined by Kabat are enclosed in boxes, except that the first enclosed box is a composite of the Chothia CDR-H1 and the Kabat CDR-H1, with the Kabat CDR-H1 underlined and bolded.

FIG. 1B depicts an alignment of light chain variable regions of the mouse 9D5 antibody, a mouse model antibody, a human acceptor antibody, and humanized versions of the 9D5 antibody. The CDRs as defined by Kabat are enclosed in boxes.

FIG. 2A depicts an alignment of heavy chain variable regions of the mouse 14G8 antibody, a mouse model antibody, human acceptor antibodies, and humanized versions of the 14G8 antibody. The CDRs as defined by Kabat are enclosed in boxes, except that the first enclosed box is a composite of the Chothia CDR-H1 and the Kabat CDR-H1, with the Kabat CDR-H1 underlined and bolded.

FIG. 2B depicts an alignment of light chain variable regions of the mouse 14G8 antibody, a mouse model antibody, human acceptor antibodies, and humanized versions of the 14G8 antibody. The CDRs as defined by Kabat are enclosed in boxes.

FIG. 3A depicts binding curves of murine 5A1, 6C1, 9D5, and 14G8 antibodies to pH4-treated TTR. FIG. 3B depicts binding curves of murine 5A1, 6C1, 9D5, and 14G8 antibodies to native TTR.

FIG. 4A depicts the inhibition of TTR-Y78F fiber formation by mis-TTR antibodies. FIG. 4B depicts the inhibition of TTR-V122I fiber formation by 14G8. FIG. 4C depicts the inhibition of TTR-V122I fiber formation by a control antibody.

FIG. 5A depicts a densitometry analysis of a Western blot analysis of plasma samples from patients confirmed for V30M ATTR (Sample #11, #12, #15, #18, #19, #20) and samples from normal subjects (Sample #21, #22, #23, #24, #25, #27) using the 9D5 mis-TTR antibody. FIG. 5B depicts a densitometry analysis of a Western blot analysis of the same samples using the 5A1 mis-TTR antibody.

FIG. 7A depicts the effect of antibody 14G8 on the uptake of F87M/L110M TTR by THP-1 cells. FIG. 7B depicts the effect of each of the mis-TTR antibodies on the uptake of V30M TTR by THP-1 cells.

FIGS. 8A-D and FIGS. 8D.1-2: 14G8 binds to TTR-V122I fibril ends and to oligomeric aggregates as assessed using TEM and AFM. Immunogold labeling with 14G8 was observed in TTR-V122I oligomer aggregates and fibril ends (FIG. 8A), whereas immunogold labeling with an anti-TTR pAb showed binding along the lengths of TTR fibers and to oligomeric clusters (FIG. 8B). IgG1 isotype control mAb did not show immunogold labeling (FIG. 8C). TTR-V122I fibers, alone and in the presence of 14G8±6 nm colloidal gold-conjugated secondary antibody, were assessed using AFM. Gold labeling was observed at fiber ends (FIG. 8D).

FIGS. 10A.1-2, 10B.1-2, 10C.1-2, 10D-F, and 10G.1-3 show 14G8 immunolabeled TTR amyloid present between fibers of the nerve fascicle a patient with ATTR amyloidosis resulting from a TTR-V30M mutation. FIG. 10A panels 1 and 2 show amyloid between fibers of the nerve fascicle, which overlapped with staining by Congo red (FIG. 8B panels 1 and 2) and thioflavin T (FIG. 10C panels 1 and 2), and immunolabeling by a total-TTR antibody (FIG. 10D) in tissue derived from a patient with ATTR amyloidosis. No staining was seen with the use of 2 isotype control antibodies (FIGS. 10E-F); however, axonal degeneration (lack of Schwann cell nuclei) in the areas laden with TTR amyloid deposits were also observed (FIGS. 10E-F [red areas in 6E]). Peripheral nerves from a healthy control were not labeled using either 14G8 or a total-TTR antibody (FIG. 10G panels 1-3).

FIGS. 11A.1-3, 11B.1-3, 11C.1-3, 11D.1-3, and 11E.1-4 shows antibody 14G8 immunolabels TTR amyloid in the gastrointestinal tract derived from a patient with TTR-C30M amyloidosis. FIG. 11A, B panels 1 show Meissner's plexus and glands in the esophagus, FIG. 11C panel 1 shows the rich vasculature bed in the submucosa, FIG. 11D panel 1 shows the muscularis propria (MP) and muscularis mucosa 14G8-positive TTR amyloid overlapped with Congo red fluorescent staining (FIGS. 11A-D panels 2). FIGS. 11A-D panels 3 show ATTR amyloidosis tissue stained with an isotype control mAb 14G8 immunoreactivity was absent in healthy control tissue (FIG. 11 panels 1-4).

FIGS. 12A-E show exemplary humanized 9D5 Vh designs, with backmutations and other mutations based on selected human frameworks. The gray-shaded areas in the first column indicate the CDRs as defined by Chothia, and the gray-shaded areas in the remaining columns indicate the CDRs as defined by Kabat.

FIGS. 13A-D show exemplary humanized 9D5 Vk designs, with backmutations and other mutations based on selected human frameworks. The gray-shaded areas in the first column indicate the CDRs as defined by Chothia, and the gray-shaded areas in the remaining columns indicate the CDRs as defined by Kabat.

FIGS. 14A-E show exemplary humanized 14G8 Vh designs, with backmutations and other mutations based on selected human frameworks. The gray-shaded areas in the first column indicate the CDRs as defined by Chothia, and the gray-shaded areas in the remaining columns indicate the CDRs as defined by Kabat.

FIGS. 15A-D show exemplary humanized 14G8 Vk designs, with backmutations and other mutations based on selected human frameworks. The gray-shaded areas in the first column indicate the CDRs as defined by Chothia, and the gray-shaded areas in the remaining columns indicate the CDRs as defined by Kabat.

BRIEF DESCRIPTION OF THE SEQUENCES

Figure 3A:
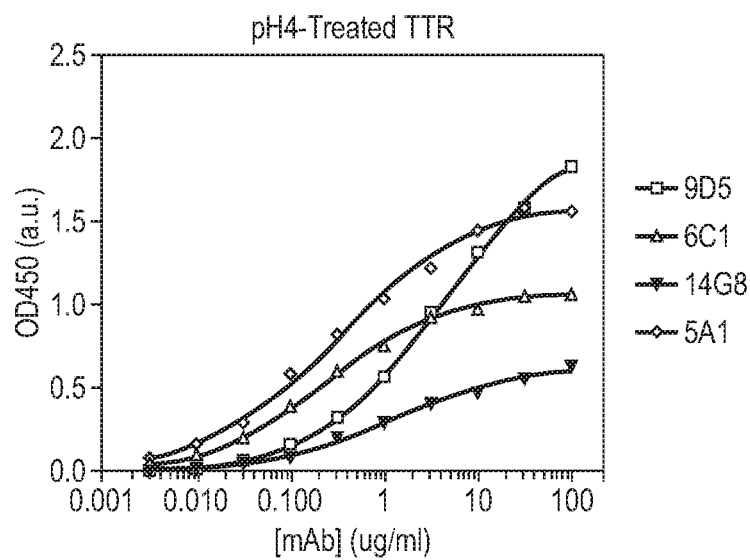
FIGS. 3A & 3B.

SEQ ID NO: 1 sets forth the amino acid sequence of the heavy chain variable region of the mouse 9D5 antibody.

SEQ ID NO: 2 sets forth the amino acid sequence of the mouse heavy chain variable region structure template 1SEQ_H.

SEQ ID NO: 3 sets forth the amino acid sequence of the heavy chain variable acceptor ACC #BAC02114.

SEQ ID NO: 4 sets forth the amino acid sequence of the heavy chain variable acceptor ACC#AAX82494.1.

SEQ ID NO: 5 sets forth the amino acid sequence of the heavy chain variable region of the humanized 9D5 antibody version 1 (Hu9D5VHv1).

SEQ ID NO: 6 sets forth the amino acid sequence of the heavy chain variable region of the humanized 9D5 antibody version 2 (Hu9D5VHv2).

SEQ ID NO: 7 sets forth the amino acid sequence of the heavy chain variable region of the humanized 9D5 antibody version 2b (Hu9D5VHv2b).

SEQ ID NO: 8 sets forth the amino acid sequence of the heavy chain variable region of the humanized 9D5 antibody version 3 (Hu9D5VHv3).

SEQ ID NO: 9 sets forth the amino acid sequence of the heavy chain variable region of the humanized 9D5 antibody version 3b (Hu9D5VHv3b).

SEQ ID NO: 10 sets forth the amino acid sequence of the heavy chain variable region of the humanized 9D5 antibody version 4 (Hu9D5VHv4).

SEQ ID NO: 11 sets forth the amino acid sequence of the heavy chain variable region of the humanized 9D5 antibody version 4b (Hu9D5VHv4b).

SEQ ID NO: 12 sets forth the amino acid sequence of the heavy chain variable region of the humanized 9D5 antibody version 5 (Hu9D5VHv5).

SEQ ID NO: 13 sets forth the amino acid sequence of Kabat CDR-H1 of the mouse 9D5 antibody.

SEQ ID NO: 14 sets forth the amino acid sequence of Kabat CDR-H2 of the mouse 9D5 antibody.

SEQ ID NO: 15 sets forth the amino acid sequence of Kabat CDR-H3 of the mouse 9D5 antibody.

SEQ ID NO: 16 sets forth the amino acid sequence of the light chain variable region of the mouse 9D5 antibody.

SEQ ID NO: 17 sets forth the amino acid sequence of mouse light chain variable region structure template 1MJU_L.

SEQ ID NO: 18 sets forth the amino acid sequence of the light chain variable acceptor ACC #ABC66952.

SEQ ID NO: 19 sets forth the amino acid sequence of the light chain variable region of the humanized 9D5 antibody version 1 (Hu9D5VLv1).

SEQ ID NO: 20 sets forth the amino acid sequence of the light chain variable region of the humanized 9D5 antibody version 2 (Hu9D5VLv2).

SEQ ID NO: 21 sets forth the amino acid sequence of the light chain variable region of the humanized 9D5 antibody version 3 (Hu9D5VLv3).

SEQ ID NO: 22 sets forth the amino acid sequence of the light chain variable region of the humanized 9D5 antibody version 4 (Hu9D5VLv4).

SEQ ID NO: 23 sets forth the amino acid sequence of the light chain variable region of the humanized 9D5 antibody version 5 (Hu9D5VLv5).

SEQ ID NO: 24 sets forth the amino acid sequence of Kabat CDR-L1 of the mouse 9D5 antibody.

SEQ ID NO: 25 sets forth the amino acid sequence of Kabat CDR-L2 of the mouse 9D5 antibody.

SEQ ID NO: 26 sets forth the amino acid sequence of Kabat CDR-L3 of the mouse 9D5 antibody.

SEQ ID NO: 27 sets forth the amino acid sequence of humanized 9D5 heavy chain version 1.

SEQ ID NO: 28 sets forth the amino acid sequence of humanized 9D5 heavy chain version 2.

SEQ ID NO: 29 sets forth the amino acid sequence of humanized 9D5 heavy chain version 2b.

SEQ ID NO: 30 sets forth the amino acid sequence of humanized 9D5 heavy chain version 3.

SEQ ID NO: 31 sets forth the amino acid sequence of humanized 9D5 heavy chain version 3b.

SEQ ID NO: 32 sets forth the amino acid sequence of humanized 9D5 heavy chain version 4.

SEQ ID NO: 33 sets forth the amino acid sequence of humanized 9D5 heavy chain version 4b.

SEQ ID NO: 34 sets forth the amino acid sequence humanized 9D5 heavy chain version 5.

SEQ ID NO: 35 sets forth the amino acid sequence of humanized 9D5 light chain version 1.

SEQ ID NO: 36 sets forth the amino acid sequence of humanized 9D5 light chain version 2.

SEQ ID NO: 37 sets forth the amino acid sequence of humanized 9D5 light chain version 3.

SEQ ID NO: 38 sets forth the amino acid sequence of humanized 9D5 light chain version 4.

SEQ ID NO: 39 sets forth the amino acid sequence of humanized 9D5 light chain version 5.

SEQ ID NO: 40 sets forth the nucleic acid sequence of the heavy chain variable region of the mouse 9D5 antibody with signal peptide.

SEQ ID NO: 41 sets forth the amino acid sequence of the heavy chain variable region of the mouse 9D5 antibody with signal peptide.

SEQ ID NO: 42 sets forth the nucleic acid sequence of the light chain variable region of the mouse 9D5 antibody with signal peptide.

SEQ ID NO: 43 sets forth the amino acid sequence of the light chain variable region of the mouse 9D5 antibody with signal peptide.

SEQ ID NO: 44 sets forth the nucleic acid sequence of the heavy chain variable region of the humanized 9D5 antibody version 1 (Hu9D5VHv1).

SEQ ID NO: 45 sets forth the nucleic acid sequence of the heavy chain variable region of the humanized 9D5 antibody version 2 (Hu9D5VHv2).

SEQ ID NO: 46 sets forth the nucleic acid sequence of the heavy chain variable region of the humanized 9D5 antibody version 2b (Hu9D5VHv2b).

SEQ ID NO: 47 sets forth the nucleic acid sequence of the heavy chain variable region of the humanized 9D5 antibody version 3 (Hu9D5VHv3).

SEQ ID NO: 48 sets forth the nucleic acid sequence of the heavy chain variable region of the humanized 9D5 antibody version 3b (Hu9D5VHv3b).

SEQ ID NO: 49 sets forth the nucleic acid sequence of the heavy chain variable region of the humanized 9D5 antibody version 4 (Hu9D5VHv4).

SEQ ID NO: 50 sets forth the nucleic acid sequence of the heavy chain variable region of the humanized 9D5 antibody version 4b (Hu9D5VHv4b).

SEQ ID NO: 51 sets forth the nucleic acid sequence of the heavy chain variable region of the humanized 9D5 antibody version 5 (Hu9D5VHv5).

SEQ ID NO: 52 sets forth the nucleic acid sequence of the light chain variable region of the humanized 9D5 antibody version 1 (Hu9D5VLv1).

SEQ ID NO: 53 sets forth the nucleic acid sequence of the light chain variable region of the humanized 9D5 antibody version 2 (Hu9D5VLv2).

SEQ ID NO: 54 sets forth the nucleic acid sequence of the light chain variable region of the humanized 9D5 antibody version 3 (Hu9D5VLv3).

SEQ ID NO: 55 sets forth the nucleic acid sequence of the light chain variable region of the humanized 9D5 antibody version 4 (Hu9D5VLv4).

SEQ ID NO: 56 sets forth the nucleic acid sequence of the light chain variable region of the humanized 9D5 antibody version 5 (Hu9D5VLv5).

SEQ ID NO: 57 sets forth the amino acid sequence of the mouse 9D5 heavy chain variable region signal peptide.

SEQ ID NO: 58 sets forth the nucleic acid sequence of the mouse 9D5 heavy chain variable region signal peptide.

SEQ ID NO: 59 sets forth the amino acid sequence of the mouse 9D5 light chain variable region signal peptide.

SEQ ID NO: 60 sets forth the nucleic acid sequence of the mouse 9D5 light chain variable region signal peptide.

SEQ ID NO: 61 sets forth the amino acid sequence of the heavy chain variable region of the mouse 14G8 antibody.

SEQ ID NO: 62 sets forth the amino acid sequence of the mouse heavy chain variable region structure template 1MQK_H.

SEQ ID NO: 63 sets forth the amino acid sequence of the heavy chain variable acceptor ACC #AAD30410.1.

SEQ ID NO: 64 sets forth the amino acid sequence of the heavy chain variable region of the humanized 14G8 antibody version 1 (Hu14G8VHv1).

SEQ ID NO: 65 sets forth the amino acid sequence of the heavy chain variable region of the humanized 14G8 antibody version 2 (Hu14G8VHv2).

SEQ ID NO: 66 sets forth the amino acid sequence of the heavy chain variable region of the humanized 14G8 antibody version 3 (Hu14G8VHv3).

SEQ ID NO: 67 sets forth the amino acid sequence of Kabat CDR-H1 of the mouse 14G8 antibody.

SEQ ID NO: 68 sets forth the amino acid sequence of Kabat CDR-H2 of the mouse 14G8 antibody.

SEQ ID NO: 69 sets forth the amino acid sequence of Kabat CDR-H3 of the mouse 14G8 antibody.

SEQ ID NO: 70 sets forth the amino acid sequence of the light chain variable region of the mouse 14G8 antibody.

SEQ ID NO: 71 sets forth the amino acid sequence of the mouse light chain variable region structure template 1MJU_L.

SEQ ID NO: 72 sets forth the amino acid sequence of the light chain variable acceptor ACC #ABA71374.1.

SEQ ID NO: 73 sets forth the amino acid sequence of the light chain variable acceptor ACC #ABC66952.1.

SEQ ID NO: 74 sets forth the amino acid sequence of the light chain variable region of the humanized 14G8 antibody version 1 (Hu14G8VLv1).

SEQ ID NO: 75 sets forth the amino acid sequence of the light chain variable region of the humanized 14G8 antibody version 2 (Hu14G8VLv2).

SEQ ID NO: 76 sets forth the amino acid sequence of the light chain variable region of the humanized 14G8 antibody version 3 (Hu14G8VLv3).

SEQ ID NO: 77 sets forth the amino acid sequence of Kabat CDR-L1 of the mouse 14G8 antibody.

SEQ ID NO: 78 sets forth the amino acid sequence of Kabat CDR-L2 of the mouse 14G8 antibody.

SEQ ID NO: 79 sets forth the amino acid sequence of Kabat CDR-L3 of the mouse 14G8 antibody.

SEQ ID NO: 80 sets forth the amino acid sequence of Kabat CDR-L1 of the humanized 14G8 antibody version 3 (Hu14G8VLv3).

SEQ ID NO: 81 sets forth the amino acid sequence of humanized 14G8 heavy chain version 1.

SEQ ID NO: 82 sets forth the amino acid sequence of humanized 14G8 heavy chain version 2.

SEQ ID NO: 83 sets forth the amino acid sequence of humanized 14G8 heavy chain version 3.

SEQ ID NO: 84 sets forth the amino acid sequence of humanized 14G8 light chain version 1.

SEQ ID NO: 85 sets forth the amino acid sequence of humanized 14G8 light chain version 2.

SEQ ID NO: 86 sets forth the amino acid sequence of humanized 14G8 light chain version 3.

SEQ ID NO: 87 sets forth the nucleic acid sequence of the heavy chain variable region of the mouse 14G8 antibody with signal peptide.

SEQ ID NO: 88 sets forth the amino acid sequence of the heavy chain variable region of the mouse 14G8 antibody with signal peptide.

SEQ ID NO: 89 sets forth the nucleic acid sequence of the light chain variable region of the mouse 14G8 antibody with signal peptide.

SEQ ID NO: 90 sets forth the amino acid sequence of the light chain variable region of the mouse 14G8 antibody with signal peptide.

SEQ ID NO: 91 sets forth the nucleic acid sequence of the heavy chain variable region of the humanized 14G8 antibody version 1 (Hu14G8VHv1).

SEQ ID NO: 92 sets forth the nucleic acid sequence of the heavy chain variable region of the humanized 14G8 antibody version 2 (Hu14G8VHv2).

SEQ ID NO: 93 sets forth the nucleic acid sequence of the heavy chain variable region of the humanized 14G8 antibody version 3 (Hu14G8VHv3).

SEQ ID NO: 94 sets forth the nucleic acid sequence of the light chain variable region of the humanized 14G8 antibody version 1 (Hu14G8VLv1).

SEQ ID NO: 95 sets forth the nucleic acid sequence of the light chain variable region of the humanized 14G8 antibody version 2 (Hu14G8VLv2).

SEQ ID NO: 96 sets forth the nucleic acid sequence of the light chain variable region of the humanized 14G8 antibody version 3 (Hu14G8VLv3).

SEQ ID NO: 97 sets forth the amino acid sequence of the mouse 14G8 heavy chain variable region signal peptide.

SEQ ID NO: 98 sets forth the nucleic acid sequence of the mouse 14G8 heavy chain variable region signal peptide.

SEQ ID NO: 99 sets forth the amino acid sequence of the mouse 14G8 light chain variable region signal peptide.

SEQ ID NO: 100 sets forth the nucleic acid sequence of the mouse 14G8 light chain variable region signal peptide.

SEQ ID NO: 101 sets forth the amino acid sequence of an exemplary human IgG1 heavy chain constant region.

SEQ ID NO: 102 sets forth the amino acid sequence of an exemplary human IgG1 heavy chain constant region of the IgG1 G1m3 allotype.

SEQ ID NO: 103 sets forth the amino acid sequence of an exemplary human IgG1 heavy chain constant region of the IgG1 G1m3 allotype.

SEQ ID NO: 104 sets forth the amino acid sequence of an exemplary human kappa light chain constant region having an N-terminal arginine.

SEQ ID NO: 105 sets forth the amino acid sequence of an exemplary human kappa light chain constant region without an N-terminal arginine.

SEQ ID NO: 106 sets forth the nucleic acid sequence of an exemplary heavy chain constant region of the G1m3 allotype.

SEQ ID NO: 107 sets forth the nucleic acid sequence of an exemplary light chain constant region having an N-terminal arginine.

SEQ ID NO: 108 sets forth the nucleic acid sequence of an exemplary light chain constant region without an N-terminal arginine.

SEQ ID NO: 109 sets forth the amino acid sequence of human transthyretin set forth in accession number P02766.1 (UniProt).

SEQ ID NO: 110 sets forth the amino acid sequence of human transthyretin set forth in accession number AAB35639.1 (GenBank).

SEQ ID NO: 111 sets forth the amino acid sequence of human transthyretin set forth in accession number AAB35640.1 (GenBank).

SEQ ID NO: 112 sets forth the amino acid sequence of human transthyretin set forth in accession number ABI63351.1 (GenBank).

SEQ ID NO: 113 sets forth the amino acid sequence of residues 89-97 of human transthyretin.

SEQ ID NO: 114 sets forth the amino acid sequence of a potential transthyretin immunogen.

SEQ ID NO: 115 sets forth the amino acid sequence of a potential transthyretin immunogen.

SEQ ID NO: 116 sets forth the amino acid sequence of a potential transthyretin immunogen.

SEQ ID NO: 117 sets forth the amino acid sequence of composite Chothia-Kabat CDR-H1 of the mouse 9D5 antibody.

SEQ ID NO: 118 sets forth the amino acid sequence of composite Chothia-Kabat CDR-H1 of the mouse 14G8 antibody.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, Md., 1987 and 1991), The Chothia definition (Chothia & Lesk, *J. Mol. Biol.* 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modeling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 . . . H34* | H26--H35B* | H26--H35B | H30--H35B |

TABLE 1-continued

Conventional Definitions of CDRs Using Kabat Numbering

| Loop | Kabat | Chothia | Composite of Chothia & Kabat | AbM | Contact |
|------|-------|---------|------------------------------|-----|---------|
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992)). In some bispecific antibodies, the two different heavy/light chain pairs include a humanized 9D5 heavy chain/light chain pair and a heavy chain/light chain pair specific for a different epitope on transthyretin than that bound by 9D5. In some bispecific antibodies, the two different heavy/light chain pairs include a humanized 14G8 heavy chain/light chain pair and a heavy chain/light chain pair specific for a different epitope on transthyretin than that bound by 14G8.

In some bispecific antibodies, one heavy chain/light chain pair is a humanized 9D5 or 14G8 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996). The epitope can be linear, such as an epitope of, for example, 2-5, 3-5, 3-9, or 5-9 contiguous amino acids from SEQ ID NO: 109. The epitope can also be a conformational epitope including, for example, two or more non-contiguous segments of amino acids within residues 89-97 of SEQ ID NO: 109.

If an antibody is said to bind to an epitope within amino acids 89-97 of transthyretin (TTR), for example, what is meant is that the epitope is within the recited range of amino acids including those defining the outer-limits of the range. It does not necessarily mean that every amino acid within the range constitutes part of the epitope. Thus, for example, an epitope within amino acids 89-97 of TTR may consist of amino acids 89-97, 89-96, 90-96, 91-96, 92-96, 93-96, 94-96, 89-96, 89-95, 89-94, 89-93, 89-92 or 89-93, among other linear segments of SEQ ID NO: 113, or in the case of conformational epitopes, non-contiguous segments of amino acids of SEQ ID NO: 113.

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "native" with respect to the structure transthyretin (TTR) refers to the normal folded structure of TTR in its properly functioning state (i.e., a TTR tetramer). As TTR is a tetramer in its natively folded form, non-native forms of TTR include, for example, misfolded TTR tetramers, TTR monomers, aggregated forms of TTR, and fibril forms of TTR. Non-native forms of TTR can include molecules comprising wild-type TTR amino acid sequences or mutations.

The term "misfolded" with respect to TTR refers to the secondary and tertiary structure of a TTR polypeptide monomer or multimer, and indicates that the polypeptide has adopted a conformation that is not normal for that protein in its properly functioning state. Although TTR misfolding can be caused by mutations in the protein (e.g., deletion, substitution, or addition), wild-type TTR proteins can also be misfolded in diseases, exposing specific epitopes.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include monomeric, misfolded, aggregated, or fibril forms of transthyretin (TTR), such as in TTR amyloid deposits. Control samples can be obtained from individuals not afflicted with a TTR amyloidosis or a specifically chosen type of TTR amyloidosis. Alternatively, control samples can be obtained from patients afflicted with TTR amyloidosis or a specifically chosen type of TTR amyloidosis. Such samples can be obtained at the same time as a biological sample thought to comprise the TTR amyloidosis or on a different occasion. A biological sample and a control sample can both be obtained from the same tissue (e.g., a tissue section containing both TTR amyloid deposits and surrounding normal tissue). Preferably, control samples consist essentially or entirely of tissue free of TTR amyloid deposits and can be used in comparison to a biological sample thought to comprise TTR amyloid deposits. Preferably, the tissue in the control sample is the same type as the tissue in the biological sample (e.g., cardiomyocytes in the heart).

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

Statistical significance means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to residues 89-97 of transthyretin (TTR). The antibodies have the capacity to bind to monomeric, misfolded, aggregated, or fibril forms of TTR. The antibodies can be used for treating or effecting prophylaxis of diseases or disorders associated with TTR accumulation or accumulation of TTR deposits (e.g., TTR amyloidosis). The antibodies can also be used for diagnosing TTR amyloidosis and inhibiting or reducing aggregation of TTR, among other applications.

II. Target Molecules

Transthyretin (TTR) is a 127-amino acid, 55 kDa serum and cerebrospinal fluid transport protein primarily synthesized by the liver. It has also been referred to as prealbumin, thyroxine binding prealbumin, ATTR, and TBPA. In its native state, TTR exists as a tetramer. In homozygotes, the tetramers comprise identical 127-amino-acid beta-sheet-rich subunits. In heterozygotes, the TTR tetramers are made up of variant and/or wild-type subunits, typically combined in a statistical fashion.

The established function of TTR in the blood is to transport holo-retinol binding protein. Although TTR is the major carrier of thyroxine ($T_4$) in the blood of rodents, utilizing binding sites that are orthogonal to those used for holo-retinol binding protein, the $T_4$ binding sites are effectively unoccupied in humans.

TTR is one of at least thirty different human proteins whose extracellular misfolding and/or misassembly (amyloidogenesis) into a spectrum of aggregate structures is thought to cause degenerative diseases referred to as amyloid diseases. TTR undergoes conformational changes in order to become amyloidogenic. Partial unfolding exposes stretches of largely uncharged hydrophobic residues in an extended conformation that efficiently misassemble into largely unstructured spherical aggregates that ultimately undergo conformation conversion into cross-beta sheet amyloid structures.

Unless otherwise apparent from context, reference to transthyretin (TTR) or its fragments or domains includes the natural human amino acid sequences including isoforms, mutants, and allelic variants thereof. Exemplary TTR polypeptide sequences are designated by Accession Numbers P02766.1 (UniProt), AAB35639.1 (GenBank), AAB35640.1 (GenBank), and ABI63351.1 (GenBank) (SEQ ID NOS: 109-112, respectively). Residues are numbered according to Swiss Prot P02766.1, with the first amino acid of the mature protein (i.e., not including the 20 amino acid signal sequence) designated residue 1. In any other TTR protein, residues are numbered according to the corresponding residues in P02766.1 on maximum alignment.

III. Transthyretin Amyloidosis

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. See, e.g., Almeida and Saraiva, *FEBS Letters* 586:2891-2896 (2012); Ando et al., *Orphanet Journal of Rare Diseases* 8:31 (2013).

In humans, both wild-type TTR tetramers and mixed tetramers comprised of mutant and wild-type subunits can dissociate, misfold, and aggregate, with the process of amyloidogenesis leading to the degeneration of post-mitotic tissue. Thus, TTR amyloidoses encompass diseases caused by pathogenic misfolded TTR resulting from mutations in TTR or resulting from non-mutated, misfolded TTR.

For example, senile systemic amyloidosis (SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. The TTR amyloidoses associated with point mutations in the TTR gene include familial amyloid polyneuropathy (FAP), familial amyloid cardiomyopathy (FAC), and the rare central nervous system selective amyloidosis (CNSA). Patients with hereditary (familial) TTR amyloidosis are almost always heterozygotes, meaning that the TTR tetramers are composed of mutant and/or wild-type TTR subunits, generally statistically distributed. Hereditary (familial) versions of TTR amyloidosis are generally autosomal dominant and are typically earlier onset than the sporadic diseases (SSA and SCA).

There are over 100 mutations in the gene encoding TTR that have been implicated in the autosomal dominant disorders FAP and FAC. See, e.g., US 2014/0056904; Saraiva, *Hum. Mutat.* 17(6):493-503 (2001); Damas and Saraiva, *J. Struct. Biol.* 130:290-299; Dwulet and Benson, *Biochem. Biophys. Res. Commun.* 114:657-662 (1983). These amyloid-causing mutations are distributed throughout the entire molecule of TTR. Generally, the more destabilizing the mutant subunits are to the TTR tetramer structure, the earlier the onset of amyloid disease. The pathogenic potential of a TTR variant is generally determined by a combination of its instability and its cellular secretion efficiency. The initial pathology caused by some TTR variants comes from their selective destruction of cardiac tissue, whereas that from other TTR variants comes from compromising the peripheral and autonomic nervous system. The tissue damage caused by TTR amyloidogenesis appear to stem largely from the toxicity of small, diffusible TTR aggregates, although accumulation of extracellular amyloid may contribute and almost certainly compromises organ structure in the late stages of the TTR amyloidosis.

TTR amyloidosis presents in many different forms, with considerable phenotypic variation across individuals and geographic locations. For example, TTR amyloidosis can present as a progressive, axonal sensory autonomic and motor neuropathy. TTR amyloidosis can also present as an infiltrative cardiomyopathy.

The age at onset of disease-related symptoms varies between the second and ninth decades of life, with great variations across different populations. The multisystem involvement of TTR amyloidosis is a clue to its diagnosis. For example, TTR amyloidosis diagnosis is considered when one or several of the following are present: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic gladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., *Orphanet Journal of Rare Diseases* 8:31 (2013). Other symptoms can include, for example, polyneuropathy, sensory loss, pain, weakness in lower limbs, dyshidrosis, diarrhea, constipation, weight loss, and urinary incontinence/retention.

Diagnosis of TTR amyloidosis typically relies on target organ biopsies, followed by histological staining of the excised tissue with the amyloid-specific dye, Congo red. If a positive test for amyloid is observed, immunohistochemical staining for TTR is subsequently performed to ensure that the precursor protein responsible for amyloid formation is indeed TTR. For familial forms of the diseases, demonstration of a mutation in the gene encoding TTR is then needed before diagnosis can be made. This can be accomplished, for example, through isoelectric focusing electrophoresis, polymerase chain reaction, or laser dissection/ liquid chromatography-tandem mass spectrometry. See, e.g., US 2014/0056904; Ruberg and Berk, *Circulation* 126:1286-1300 (2012); Ando et al., *Orphanet Journal of Rare Diseases* 8:31 (2013).

IV. Antibodies

A. Binding Specificity and Functional Properties

The invention provides monoclonal antibodies binding to transthyretin (TTR) protein, more specifically, to epitopes within amino acid residues 89-97 (SEQ ID NO: 113) of TTR. Such epitopes are buried in the native TTR tetramer and exposed in monomeric, misfolded, aggregated, or fibril forms of TTR.

Antibodies designated 9D5 and 14G8 are two such exemplary mouse antibodies. Unless otherwise apparent from context, reference to 9D5 or 14G8 should be understood as referring to any of the mouse, chimeric, veneered, and humanized forms of these antibodies. These antibodies specifically bind within amino acid residues 89-97 (SEQ ID NO: 113) of TTR. These antibodies are further characterized by their ability to bind to monomeric, misfolded, aggregated, or fibril forms of TTR but not to native tetrameric forms of TTR. In addition, these antibodies are characterized by their immunoreactivity on TTR-mediated amyloidosis cardiac tissue but not on healthy cardiac tissue. Ability to bind to specific proteins or fragments thereof may be demonstrated using exemplary assay formats provided in the examples.

Some antibodies bind to the same or overlapping epitope as an antibody designated 9D5 or 14G8. The sequences of the heavy and light chain mature variable regions of these antibodies are designated SEQ ID NOS: 1 and 16 (9D5), and 61 and 70 (14G8), respectively. Other antibodies having such a binding specificity can be produced by immunizing mice with TTR, or a portion thereof including the desired epitope (e.g., SEQ ID NO: 113), and screening resulting antibodies for binding to monomeric TTR or a peptide comprising SEQ ID NO: 113, optionally in competition with an antibody having the variable regions of mouse 9D5 or 14G8 (IgG1 kappa). Fragments of TTR including the desired epitope can be linked to a carrier that helps elicit an antibody response to the fragment and/or be combined with an adjuvant that helps elicit such a response. Such antibodies can be screened for differential binding to wild-type, monomeric versions of TTR or a fragment thereof (e.g., SEQ ID NO: 113) compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 9D5 or 14G8) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding (e.g., at least $10^8$ and preferably at least $10^9$ M$^{-1}$) for monomeric TTR or a fragment thereof (e.g., amino acid residues 89-97) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for monomeric TTR or a fragment thereof (e.g., amino acid residues 89-97) are selected. The resulting antibodies usually have the same or similar epitope specificity as the murine starting material. Kabat CDRs of the heavy chain of 9D5 are designated SEQ ID NOS: 13-15, respectively, and Kabat CDRs of the light chain of 9D5 are designated SEQ ID NOS: 24-26, respectively. A composite Chothia-Kabat CDR-H1 of 9D5 is designated SEQ ID NO: 117. Kabat CDRs of the heavy chain of 14G8 are designated SEQ ID NOS: 67-69, respectively, and Kabat CDRs of the light chain of 14G8 are designated SEQ ID NOS: 77-79, respectively. A composite Chothia-Kabat CDR-H1 of 14G8 is designated SEQ ID NO: 118. A variant of CDR-L1 of 14G8 is designated SEQ ID NO: 80.

Other antibodies can be obtained by mutagenesis of cDNA encoding the heavy and light chains of an exemplary antibody, such as 9D5 or 14G8. Monoclonal antibodies that are at least 70%, 80%, 90%, 95%, 96%, 97%, 98%, or 99% identical to 9D5 or 14G8 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 9D5 or 14G8 are also included.

The invention also provides antibodies having some or all (e.g., 3, 4, 5, and 6) CDRs entirely or substantially from 9D5 or 14G8. Such antibodies can include a heavy chain variable region that has at least two, and usually all three, CDRs entirely or substantially from the heavy chain variable region of 9D5 or 14G8 and/or a light chain variable region having at least two, and usually all three, CDRs entirely or substantially from the light chain variable region of 9D5 or 14G8. The antibodies can include both heavy and light chains. A CDR is substantially from a corresponding 9D5 or 14G8 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 9D5 or 14G8 in the amino acid sequence of the mature heavy and/or light chain variable regions and maintain their functional properties, and/or differ from 9D5 or 14G8 by a small number of functionally inconsequential amino acid substitutions (e.g., conservative substitutions), deletions, or insertions.

Some antibodies identified by such assays can bind to monomeric, misfolded, aggregated, or fibril forms of TTR but not to native tetrameric forms of TTR, as described in the examples or otherwise. Likewise, some antibodies are immunoreactive on TTR-mediated amyloidosis tissue but not on healthy tissue.

Some antibodies can inhibit or reduce aggregation of TTR, inhibit or reduce TTR fibril formation, reduce or clear TTR deposits or aggregated TTR, or stabilize non-toxic conformations of TTR in an animal model or clinical trial. Some antibodies can treat, effect prophylaxis of, or delay the onset of a TTR amyloidosis as shown in an animal model or clinical trial. Exemplary animal models for testing activity against a TTR amyloidosis include those described in Kohno et al., *Am. J. Path.* 150(4):1497-1508 (1997); Teng et al., *Laboratory Investigations* 81:385-396 (2001); Wakasugi et al., *Proc. Japan Acad.* 63B:344-347 (1987); Shimada et al., *Mol. Biol. Med.* 6:333-343 (1989); Nagata et al., *J. Biochem.* 117:169-175 (1995); Sousa et al., *Am. J. Path.* 161:1935-1948 (2002); and Santos et al., *Neurobiology of Aging* 31:280-289 (2010).

B. Non-Human Antibodies

The production of other non-human antibodies, e.g., murine, guinea pig, primate, rabbit or rat, against monomeric TTR or a fragment thereof (e.g., amino acid residues 89-97) can be accomplished by, for example, immunizing the animal with TTR or a fragment thereof. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to monomeric TTR or an epitope within TTR (e.g., an epitope comprising one or more of amino acid residues 89-97). Such screening can be accomplished by determining binding of an antibody to a collection of monomeric TTR variants, such as TTR variants containing amino acid residues 89-97 or mutations within these residues, and determining which TTR variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by any conventional definition but preferably defined by Kabat are identical.

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.*, 320: 415-428, 2002; Iwahashi et al., *Mol. Immunol.* 36:1079-1091, 1999; Tamura et al, *J. Immunol.*, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Examples of acceptor sequences for the heavy chain are the human mature heavy chain variable regions with NCBI accession codes BAC02114 and AAX82494.1 (SEQ ID NOS: 3 and 4) and heavy chain variable regions of human Kabat subgroup 3. BAC02114 shares the same canonical form as mouse 9D5 heavy chain. Other examples of acceptor sequences for the heavy chain are the human mature heavy chain variable regions with NCBI accession codes AAD30410.1 and AAX82494.1 (SEQ ID NOS: 63 and 4, respectively) and heavy chain variable regions of human Kabat subgroup 1. AAD30410.1 and AAX82494.1 include two CDRs having the same canonical form as mouse 14G8 heavy chain. Examples of acceptor sequences for the light chain are the human mature light chain variable region with NCBI accession code ABC66952 (SEQ ID NO: 18) and light chain variable regions of human Kabat subgroup 3. ABC66952 includes two CDRs having the same canonical form as mouse 9D5 light chain. Other examples of acceptor sequences for the light chain are the human mature light chain variable regions with NCBI accession codes ABA71374.1 and ABC66952.1 (SEQ ID NOS: 72 and 73, respectively) and light chain variable regions of human Kabat subgroup 2. ABA71374.1 and ABC66952.1 have the same canonical form as mouse 14G8 light chain.

If more than one human acceptor antibody sequence is selected, a composite or hybrid of those acceptors can be used, and the amino acids used at different positions in the humanized light chain and heavy chain variable regions can be taken from any of the human acceptor antibody sequences used. For example, the human mature heavy chain variable regions with NCBI accession codes BAC02114 and AAX82494.1 (SEQ ID NOS: 3 and 4) were used as acceptor sequences for humanization of the 9D5 mature heavy chain variable region. Examples of positions in which these two acceptors differ include positions H19 (R or K), H40 (A or T), H44 (G or R), H49 (S or A), H77 (S or T), H82a (N or S), H83 (R or K), H84 (A or S), and H89 (V or M). Humanized versions of the 9D5 heavy chain variable region can include either amino acid at any of these positions. Similarly, the human mature heavy chain variable regions with NCBI accession codes AAD30410.1 and AAX82494.1 (SEQ ID NOS: 63 and 4, respectively) were used as acceptor sequences for humanization of the 14G8 mature heavy chain variable region. Examples of positions in which these two acceptors differ include positions H82a (N or S), H83 (R or K), H84 (A or S), and H89 (V or M). Humanized versions of the 14G8 heavy chain variable region can include either amino acid at any of these positions. Similarly, the human mature light chain variable regions with NCBI accession codes ABA71374.1 and ABC66952.1 (SEQ ID NOS: 72 and 73, respectively) were used as acceptor sequences for humanization of the 14G8 mature light chain variable region. An example of a position in which these two acceptors differ is position L18 (S or P). Humanized versions of the 14G8 light chain variable region can include either amino acid at this position.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Exemplary humanized antibodies are humanized forms of the mouse 9D5 or 14G8 antibodies, designated Hu9D5 or Hu14G8, respectively. The mouse 9D5 antibody comprises mature heavy and light chain variable regions having amino acid sequences comprising SEQ ID NO: 1 and SEQ ID NO: 16, respectively. The invention provides eight exemplified humanized mature heavy chain variable regions: Hu9D5VHv1, Hu9D5VHv2, Hu9D5VHv2b, Hu9D5VHv3, Hu9D5VHv3b, Hu9D5VHv4, Hu9D5VHv4b, and Hu9D5VHv5 (SEQ ID NOS: 5-12, respectively). The invention further provides five exemplified human mature light chain variable regions: Hu9D5VLv1, Hu9D5VLv2, Hu9D5VLv3, Hu9D5VLv4, and Hu9D5VLv5 (SEQ ID NOS: 19-23, respectively). FIG. 1 shows alignments of 9D5, mouse model antibodies, human acceptor antibodies, and various humanized antibodies.

The mouse 14G8 antibody comprises mature heavy and light chain variable regions having amino acid sequences comprising SEQ ID NO: 61 and SEQ ID NO: 70, respectively. The invention provides three exemplified humanized mature heavy chain variable regions: Hu14G8VHv1, Hu14G8VHv2, and Hu14G8VHv3 (SEQ ID NOS: 64-66, respectively). The invention further provides three exemplified human mature light chain variable regions: Hu14G8VLv1, Hu14G8VLv2, and Hu14G8VLv3 (SEQ ID NOS: 74-76, respectively). FIG. 2 shows alignments of 14G8, mouse model antibodies, human acceptor antibodies, and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 15 variable region framework positions were considered as candidates for substitutions in the eight exemplified Hu9D5 mature heavy chain variable regions and the five exemplified Hu9D5 mature light chain variable regions, as further specified in the examples: H42 (G42E), H47 (W47L), H69 (I69F), H82 (M82S), H82b (S82(b)L), H108 (T108L), L8 (P8A), L9 (L9P), L18 (P18S), L19 (A19V), L36 (Y36F), L39 (K39R), L60 (D60S), L70

(D70A), and L74 (K74R). Likewise, the following 11 variable region framework positions were considered as candidates for substitutions in the three exemplified Hu14G8 mature heavy chain variable regions and the three exemplified Hu14G8 mature light chain variable regions, as further specified in the examples: H1 (Q1E), H3 (Q3K), H47 (W47L), H105 (Q105T), L8 (P8A), L9 (L9P), L19 (A19V), L26 (N26S), L36 (Y36F), L60 (D60S), and L70 (D70A).

Here, as elsewhere, the first-mentioned residue is the residue of a humanized antibody formed by grafting Kabat CDRs or a composite Chothia-Kabat CDR in the case of CDR-H1 into a human acceptor framework (e.g., a composite or hybrid human acceptor framework), and the second-mentioned residue is a residue being considered for replacing such residue. Thus, within variable region frameworks, the first mentioned residue is human, and within CDRs, the first mentioned residue is mouse.

Exemplified Hu9D5 antibodies include any permutations or combinations of the exemplified mature heavy and light chain variable regions (e.g., VHv1/VLv1 or H1L1, VHv1/VLv2 or H1L2, VHv1/VLv3 or H1L3, VHv1/VLv4 or H1L4, VHv1/VLv5 or H1L5, VHv2/VLv1 or H2L1, VHv2/VLv2 or H2L2, VHv2/VLv3 or H2L3, VHv2/VLv4 or H2L4, VHv2/VLv5 or H2L5, VHv2b/VLv1 or H2bL1, VHv2b/VLv2 or H2bL2, VHv2b/VLv3 or H2bL3, VHv2b/VLv4 or H2bL4, VHv2b/VLv5 or H2bL5, VHv3/VLv1 or H3L1, VHv3/VLv2 or H3L2, VHv3/VLv3 or H3L3, VHv3/VLv4 or H3L4, VHv3/VLv5 or H3L5, VHv3b/VLv1 or H3bL1, VHv3b/VLv2 or H3bL2, VHv3b/VLv3 or H3bL3, VHv3b/VLv4 or H3bL4, VHv3b/VLv5 or H3bL5, VHv4/VLv1 or H4L1, VHv4/VLv2 or H4L2, VHv4/VLv3 or H4L3, VHv4/VLv4 or H4L4, VHv4/VLv5 or H4L5, VHv4b/VLv1 or H4bL1, VHv4b/VLv2 or H4bL2, VHv4b/VLv3 or H4bL3, VHv4b/VLv4 or H4bL4, VHv4b/VLv5 or H4bL5, VHv5/VLv1 or H5L1, VHv5/VLv2 or H5L2, VHv5/VLv3 or H5L3, VHv5/VLv4 or H5L4, and VHv5/VLv5 or H5L5).

The invention provides variants of humanized 9D5 antibodies in which the humanized mature heavy chain variable region shows at least 90%, 95%, 96%, 97%, 98%, or 99% identity to a humanized Hu9D5VHv4b (SEQ ID NO: 11) and the humanized mature light chain variable region shows at least 90%, 95%, 96%, 97%, 98%, or 99% identity to a Hu9D5VLv1 (SEQ ID NO: 19). In some such antibodies, at least 1, 2, or all 3 of the backmutations or other mutations in Hu9D5 H4bL1 are retained. The invention also provides variants of the other exemplified humanized 9D5 antibodies. Such variants have mature light and heavy chain variable regions showing at least 90%, 95%, 96%, 97%, 98%, or 99% sequence identity to the mature light and heavy chain variable regions of the exemplified humanized 9D5 H1L1, H1L2, H1L3, H1L4, H1L5, H2L1, H2L2, H2L3, H2L4, H2L5, H2bL1, H2bL2, H2bL3, H2bL4, H2bL5, H3L1, H3L2, H3L3, H3L4, H3L5, H3bL1, Hb3L2, H3bL3, Hb3L4, H3bL5, H4L1, H4L2, H4L3, H4L4, H4L5, H4bL1, H4bL2, H4bL3, H4bL4, H4bL5, H5L1, H5L2, H5L3, H5L4, or H5L5 antibodies.

In some antibodies, at least one of positions H42, H47, H69, H82, H82b, and H108 in the Vh region is occupied by E, L, F, S, L, and L, respectively. In some antibodies, positions H47, H69, and H82 in the Vh region are occupied by L, F, and S, respectively, as in Hu9D5VHv1. In some antibodies, positions H47, H69, H82, and H82b in the Vh region are occupied by L, F, S, and L, respectively, as in Hu9D5VHv2. In some antibodies, positions H42, H47, and H108 in the Vh region are occupied by E, L, and L, respectively, as in Hu9D5VHv2b. In some antibodies, positions H69, H82, and H82b in the Vh region are occupied by F, S, and L, respectively, as in Hu9D5VHv3. In some antibodies, positions H47 and H108 in the Vh region are each occupied by L, as in Hu9D5VHv3b and Hu9D5Vhv4b. In some antibodies, positions H82 and H82b in the Vh region are occupied by S and L, respectively, as in Hu9D5VHv4. In some antibodies, positions H42, H47, and H82b in the Vh region are occupied by E, L, and L, respectively, as in Hu9D5VHv5. In some antibodies, at least one of positions L8, L9, L18, L19, L36, L39, L60, L70, and L74 in the Vk region is occupied by A, P, S, V, F, R, S, A, and R, respectively. In some antibodies, position L36 in the Vk region is occupied by F, as in Hu9D5VLv1. In some antibodies, position L60 in the Vk region is occupied by S, as in Hu9D5VLv3. In some antibodies, positions L8, L9, L19, L36, L39, L60, L70, and L74 in the Vk region are occupied by A, P, V, F, R, S, A, and R, respectively, as in Hu9D5VLv4. In some antibodies, positions L8, L9, L18, L19, L36, L39, L60, L70, and L74 in the Vk region are occupied by A, P, S, V, F, R, S, A, and R, respectively, as in Hu9D5VLv5. The CDR regions of such humanized antibodies can be identical or substantially identical to the CDR regions of the 9D5 mouse donor antibody or any of the above exemplified humanized 9D5 antibodies. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu9D5 heavy and light chains by a small number (e.g., typically no more than 1, 2, 3, 5, 10, or 15) of replacements, deletions or insertions. Such differences are usually in the framework but can also occur in the CDRs.

Exemplified Hu14G8 antibodies include any permutations or combinations of the exemplified mature heavy and light chain variable regions (e.g., VHv1/VLv1 or H1L1, VHv1/VLv2 or H1L2, VHv1/VLv3 or H1L3, VHv2/VLv1 or H2L1, VHv2/VLv2 or H2L2, VHv2/VLv3 or H2L3, VHv3/VLv1 or H3L1, VHv3/VLv2 or H3L2, and VHv3/VLv3 or H3L3).

The invention provides variants of humanized 14G8 antibodies in which the humanized mature heavy chain variable region shows at least 90%, 95%, 96%, 97%, 98%, or 99% identity to Hu14G8VHv2 (Hu14G8 H2) (SEQ ID NO: 65) and the humanized mature light chain variable region shows at least 90%, 95%, 96%, 97%, 98%, or 99% identity to Hu14G8VLv3 (Hu14G8 L3) (SEQ ID NO: 76). In some such antibodies, at least 1, 2, 3, 4, or all 5 of the backmutations or other mutations in Hu14G8 H2L3 are retained. The invention also provides variants of the other exemplified humanized 14G8 antibodies. Such variants have mature light and heavy chain variable regions showing at least 90%, 95%, 96%, 97%, 98%, or 99% sequence identity to the mature light and heavy chain variable regions of the exemplified humanized 14G8 H1L1, H1L2, H1L3, H2L1, H2L2, H2L3, H3L1, H3L2, or H3L3 antibodies.

In some antibodies, at least one of positions H1 and H47 in the Vh region is occupied by E and L, respectively. In some antibodies, positions H1 and H47 in the Vh region are occupied by E and L, respectively, as in Hu14G8VHv2 and Hu14G8VHv3. In some antibodies, at least one of positions H3 and H105 in the Vh region is occupied by K and T, respectively. In some antibodies, positions H3 and H105 in the Vh region are occupied by K and T, respectively, as in Hu14G8VHv1. In some antibodies, position L36 in the Vk region is occupied by F, as in Hu14G8VLv2. In some antibodies, at least one of positions L8, L9, L19, L26, L60, and L70 in the Vk region is occupied by A, P, V, S, S, and A, respectively. In some antibodies, positions L8, L9, L19, and L70 in the Vk region are occupied by A, P, V, and A, respectively, as in Hu14G8VLv1. In some antibodies, positions L26 and L60 in the Vk region are each occupied by S, as in Hu14G8VLv3. The CDR regions of such humanized antibodies can be identical or substantially identical to the CDR regions of the 14G8 mouse donor antibody. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu14G8 heavy and light chains by a small number (e.g., typically no more than 1, 2, 3, 5, 10, or 15) of replacements, deletions or insertions. Such differences are usually in the framework but can also occur in the CDRs A possibility for additional variation in humanized 9D5 or 14G8 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 9D5 or 14G8 variants (whether or not conservative) have no substantial effect on the binding affinity or potency of the humanized mAb, that is, its ability to bind to monomeric TTR (e.g., the potency in some or all of the assays described in the present examples of the variant humanized 9D5 or 14G8 antibody is essentially the same, i.e., within experimental error, as that of murine 9D5 or 14G8 antibody).

D. Chimeric and Veneered Antibodies

The invention further provides chimeric and veneered forms of non-human antibodies, particularly the 9D5 or 14G8 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 9D5 or 14G8 antibody are included in the invention.

E. Human Antibodies

Human antibodies against monomeric TTR or a fragment thereof (e.g., amino acid residues 89-97 (SEQ ID NO: 113) of TTR) are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for particular epitope specificity by using only a fragment of TTR, such as a TTR variant containing only amino acid residues 89-97 of TTR, as the target antigen, and/or by screening antibodies against a collection of TTR variants, such as TTR variants containing various mutations within amino acid residues 89-97 of TTR.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397; U.S. Pat. No. 5,874,299; U.S. Pat. No. 5,814,318; U.S. Pat. No. 5,789,650; U.S. Pat. No. 5,770,429; U.S. Pat. No. 5,661,016; U.S. Pat. No. 5,633,425; U.S. Pat. No. 5,625,126; U.S. Pat. No. 5,569,825; U.S. Pat. No. 5,545,806; Neuberger, *Nat. Biotechnol.* 14:826 (1996); and Kucherlapati, WO 91/10741 (1991)) and phage display methods (see, e.g., Dower et al., WO 91/17271; McCafferty et al., WO 92/01047; U.S. Pat. No. 5,877,218; U.S. Pat. No. 5,871,907; U.S. Pat. No. 5,858,657; U.S. Pat. No. 5,837,242; U.S. Pat. No. 5,733,743; and U.S. Pat. No. 5,565,332).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcy receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO: 102. In some antibodies, the isotype is human IgG2 or IgG4.

An exemplary human light chain kappa constant region has the amino acid sequence of SEQ ID NO: 104. The N-terminal arginine of SEQ ID NO: 104 can be omitted, in which case light chain kappa constant region has the amino acid sequence of SEQ ID NO: 105. An exemplary human IgG1 heavy chain constant region has the amino acid sequence of SEQ ID NO: 101 (with or without the C-terminal lysine). Antibodies can be expressed as tetramers containing two light and two heavy chains, as separate heavy chains, light chains, as Fab, Fab', F(ab')$_2$, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence of SEQ ID NO: 103. Another heavy chain constant region of the IgG1 G1m3 allotype has the amino acid sequence of SEQ ID NO: 102 (with or without the C-terminal lysine). Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO: 106, which encodes a human IgG1 constant region (SEQ ID NO: 103), and SEQ ID NOS: 107 and 108, which encode human kappa light chain constant regions (SEQ ID NOS: 104 and 105, respectively).

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. No. 5,741,957; U.S. Pat. No. 5,304,489; and U.S. Pat. No. 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. No. 5,786,464; U.S. Pat. No. 6,114,148; U.S. Pat. No. 6,063,598; U.S. Pat. No. 7,569,339; WO2004/050884; WO2008/012142; WO2008/012142; WO2005/019442; WO2008/107388; WO2009/027471; and U.S. Pat. No. 5,888,809).

H. Antibody Screening Assays

Antibodies can be subject to several screens including binding assays, functional screens, screens in animal models of diseases associated with TTR deposits, and clinical trials. Binding assays test for specific binding and, optionally, affinity and epitope specificity to monomeric TTR or a fragment thereof. For example, binding assays can screen for antibodies that bind to amino acid residues 89-97 (SEQ ID NO: 113) of TTR, which is an epitope that is buried in the native TTR tetramer and exposed in monomeric, misfolded, aggregated, or fibril forms of TTR. Antibodies can also be screened for the ability to bind pre-fibrillar, non-native conformations of TTR and TTR amyloid fibrils but not native TTR conformations. For example, antibodies can be screened for the ability to bind to monomeric forms of TTR created by dissociation or disaggregation of native tetrameric TTR, and can be counter-screened against native tetrameric TTR, as described in the examples or otherwise. Likewise, antibodies can also be screened for their immunoreactivity on TTR-mediated amyloidosis tissue but not on healthy tissue. Such screens are sometimes performed in competition with an exemplary antibody, such as an antibody having the variable regions of 9D5 or 14G8 (IgG1 kappa isotype). Optionally, either the antibody or TTR target is immobilized in such assay.

Functional assays can be performed in cellular models including cells naturally expressing TTR or transfected with DNA encoding TTR or a fragment thereof. Suitable cells include cells derived from cardiac tissue or other tissues affected by TTR amyloidogenesis. Cells can be screened for reduced levels of monomeric, misfolded, aggregated, or fibril forms of TTR (e.g., by Western blotting or immunoprecipitation of cell extracts or supernatants) or reduced toxicity attributable to monomeric, misfolded, aggregated, or fibril forms of TTR. For example, antibodies can tested for the ability to inhibit or reduce aggregation of TTR, inhibit or reduce TTR fibril formation, reduce TTR deposits, clear aggregated TTR, or stabilize non-toxic conformations of TTR.

Other functional assays can be performed in solution, such as testing whether an antibody is capable of disrupting or reducing TTR fibril formation when monomeric TTR or misfolded TTR intermediates in solution are contacted with the antibody. The extent of fibril formation can be probed by turbidity measurements, for example, at 400 nm on a UV-visible spectrometer equipped with a temperature control unit. Thioflavin-T can also be used to assess the extent of amyloid fibril formation. For example, a five-fold molar excess of Thioflavin-T can be added to TTR samples and left at room temperature for 30 minutes before measurements are taken. Thioflavin-T fluorescence can be monitored using a spectrofluorimeter. See US 2014/0056904.

Animal model screens test the ability of the antibody to therapeutically or prophylactically treat signs or symptoms in an animal model simulating a human disease associated with accumulation of TTR or TTR deposits. Such diseases include types of TTR amyloidosis, such as senile systemic amyloidosis (SSA), senile cardiac amyloidosis (SCA), familial amyloid polyneuropathy (FAP), familial amyloid cardiomyopathy (FAC), and central nervous system selective amyloidosis (CNSA). Suitable signs or symptoms that can be monitored include the presence and extent of amyloid deposits in various tissues, such as the gastrointestinal tract or heart. The extent of reduction of amyloid deposits can be determined by comparison with an appropriate control, such the level of TTR amyloid deposits in control animals that have received a control antibody (e.g., an isotype matched control antibody), a placebo, or no treatment at all. An exemplary animal model for testing activity against a TTR amyloidosis is a mouse model carrying a null mutation at the endogenous mouse Ttr locus and the human mutant TTR gene comprising a V30M mutation that is associated with familial amyloidotic polyneuropathy. See, e.g., Kohno et al., *Am. J. Path.* 150(4):1497-1508 (1997); Cardoso and Saraiva, *FASEB J* 20(2):234-239 (2006). Similar models also exist, including other models for familial versions of TTR amyloidosis and models for sporadic versions of TTR amyloidosis. See, e.g., Teng et al., *Lab. Invest.* 81(3): 385-396 (2001); Ito and Maeda, Mouse Models of Transthyretin Amyloidosis, in Recent Advances in Transthyretin Evolution, Structure, and Biological Functions, pp. 261-280 (2009) (Springer Berlin Heidelberg). Transgenic animals can include a human TTR transgene, such as a TTR transgene with a mutation associated with TTR amyloidosis or a wild-type TTR transgene. To facilitate testing in animal models, chimeric antibodies having a constant region appropriate for the animal model can be used (e.g., mouse-rat chimeras could be used for testing antibodies in rats). It can be concluded that a humanized version of an antibody will be effective if the corresponding mouse antibody or chimeric antibody is effective in an appropriate animal model and the humanized antibody has similar binding affinity (e.g., within experimental error, such as by a factor of 1.5, 2, or 3).

Clinical trials test for safety and efficacy in a human having a disease associated with TTR amyloidosis.

I. Nucleic Acids

The invention further provides nucleic acids encoding any of the heavy and light chains described above (e.g., SEQ ID NOS: 40, 42, 44-56, 87, 89, 91-96, and 106-108). Optionally, such nucleic acids further encode a signal peptide and can be expressed with the signal peptide linked to the constant region (e.g., signal peptides having amino acid sequences of SEQ ID NOS: 41 and 88 (heavy chain) and 43 and 90 (light chain) that can be encoded by SEQ ID NOS: 40 and 87, respectively (heavy chain) and 42 and 89, respectively (light chain)). Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens exposed in pathogenic forms of TTR but not in native tetrameric forms of TTR, such as amino acid residues 89-97 (SEQ ID NO: 113) of TTR, are useful in detecting the presence of monomeric, misfolded, aggregated, or fibril forms of TTR; monitoring and evaluating the efficacy of therapeutic agents being used to treat patients diagnosed with a TTR amyloidosis; inhibiting or reducing aggregation of TTR; inhibiting or reducing TTR fibril formation; reducing or clearing TTR deposits; stabilizing non-toxic conformations of TTR; or treating or effecting prophylaxis of a TTR amyloidosis in a patient. For example, such antibodies can be conjugated with other therapeutic moieties, other proteins, other antibodies, and/or detectable labels. See WO 03/057838; U.S. Pat. No. 8,455,622.

Conjugated therapeutic moieties can be any agent that can be used to treat, combat, ameliorate, prevent, or improve an unwanted condition or disease in a patient, such as a TTR amyloidosis. Therapeutic moieties can include, for example, immunomodulators or any biologically active agents that facilitate or enhance the activity of the antibody. An immunomodulator can be any agent that stimulates or inhibits the development or maintenance of an immunologic response. If such therapeutic moieties are coupled to an antibody specific for monomeric, misfolded, aggregated, or fibril forms of TTR, such as the antibodies described herein, the coupled therapeutic moieties will have a specific affinity for non-native, pathogenic forms of TTR over native tetrameric forms of TTR. Consequently, administration of the conjugated antibodies directly targets tissues comprising pathogenic forms of TTR with minimal damage to surrounding normal, healthy tissue. This can be particularly useful for therapeutic moieties that are too toxic to be administered on their own. In addition, smaller quantities of the therapeutic moieties can be used.

Examples of suitable therapeutic moieties include drugs that reduce levels of TTR, stabilize the native tetrameric structure of TTR, inhibit aggregation of TTR, disrupt TTR fibril or amyloid formation, or counteract cellular toxicity. See, e.g., Almeida and Saraiva, *FEBS Letters* 586:2891-2896 (2012); Saraiva, *FEBS Letters* 498:201-203 (2001); Ando et al., *Orphanet Journal of Rare Diseases* 8:31 (2013); Ruberg and Berk, *Circulation* 126:1286-1300 (2012); and Johnson et al., *J. Mol. Biol.* 421(2-3):185-203 (2012). For example, antibodies can be conjugated to tafamidis, diflunisal, ALN-TTR01, ALNTTR02, ISIS-TTRRx, doxycycline (doxy), tauroursodeoxycholic acid (TUDCA), Doxy-TUDCA, epigallocatechin gallate (EGCG), curcumin, or resveratrol (3,5,4'-trihydroxystilbene). Other representative therapeutic moieties include other agents known to be useful for treatment, management, or amelioration of a TTR amyloidosis or symptoms of a TTR amyloidosis. See, e.g., Ando et al., *Orphanet Journal of Rare Diseases* 8:31 (2013) for common clinical symptoms of TTR amyloidosis and typical agents used to treat those symptoms.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within TTR or a portion thereof or can bind to a different target antigen.

Antibodies can also be coupled with a detectable label. Such antibodies can be used, for example, for diagnosing a TTR amyloidosis, for monitoring progression of a TTR amyloidosis, and/or for assessing efficacy of treatment. Such antibodies are particularly useful for performing such determinations in subjects having or being susceptible to a TTR amyloidosis, or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as yttrium$^{90}$ (90Y), radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.*, 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., Immunol. Rev., 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

V. Therapeutic Applications

The above antibodies can be used for treating or effecting prophylaxis of a disease in a patient having or at risk for the disease mediated at least in part by transthyretin (TTR), and particularly by monomeric, misfolded, aggregated, or fibril forms of TTR. Although an understanding of mechanism is not required for practice, it is believed that any or all of the following mechanisms may contribute to treatment of TTR amyloidosis using the above antibodies: antibody-mediated inhibition of TTR aggregation and fibril formation, antibody-mediated stabilization of non-toxic conformations of TTR (e.g., tetrameric forms), or antibody-mediated clearance of aggregated TTR, oligomeric TTR, or monomeric TTR. Antibody-drug conjugates can have additional mechanisms of action determined by the conjugated moiety.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

VI. Pharmaceutical Compositions and Methods of Use

Provided herein are several methods of diagnosing, monitoring, treating or effecting prophylaxis of diseases or conditions mediated at least in part by transthyretin (TTR), and particularly by monomeric, misfolded, aggregated, or fibril forms of TTR (e.g., TTR amyloidosis). Examples of such diseases include familial TTR amyloidoses, such as familial amyloid cardiomyopathy (FAC) or cardiomyopathy or hypertrophy in athletes or others undergoing extreme aerobic exercise, familial amyloid polyneuropathy (FAP), or central nervous system selective amyloidosis (CNSA), and sporadic TTR amyloidoses, such as senile systemic amyloidosis (SSA) or senile cardiac amyloidosis (SCA). TTR amyloidosis can also be associated as a cause or result of various diseases and conditions characterized by tissue or organ degeneration or trauma. Accumulation of TTR deposits contributes to organ or tissue dysfunction associated with the disease or condition. An example of such a condition amenable to treatment or prophylaxis with the present agents and methods is spinal stenosis (Westermark et al., Upsala J. Medical Sciences 119, 223-238 (2014) and Yanagisawa et al., Modern Pathology 28, 201-207 (2015). Another disease likewise amenable to treatment or prophylaxis is osteoarthritis (Takanashi et al., Amyloid 20, 151-155 (2013), Gu et al., Biomed & Biotechnol. 15, 92-99; Takinami et al., Biomarker Insights 8, 85-95 (2014); Akasaki et al., Arthritis Rheumatol. 67, 2097-2107 (2015). Another disease likewise amenable to treatment or prophylaxis is rheumatoid arthritis (Clement et al., JCI Insight 1 epublish (2016). Another disease amenable to treatment or prophylaxis is juvenile idiopathic arthritis (Sharma et al., PLOSone 9, 1-12 (2014). Another disease amenable to treatment or prophylaxis is age related macular degeneration (wet or dry). Another class of conditions likewise amenable to treatment or prophylaxis are ligament and tendon disorders, such as disorders of the rotator cuff (Sueyoshi et al., Human Pathol. 42, 1259-64 (2011).

Antibodies described above can be incorporated into a pharmaceutical composition for use treatment or prophylaxis of any of the above diseases and conditions. In general, an antibody or pharmaceutical composition containing an antibody is administered to a subject in need thereof. Patients amenable to treatment include individuals at risk of TTR amyloidosis but not showing symptoms, as well as patients presently showing symptoms. Some patients can be treated during the prodromal stage of TTR amyloidosis.

Individuals suffering from TTR amyloidosis can sometimes be recognized from the clinical manifestations of TTR amyloidosis, including one or more of the following: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic gladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., *Orphanet Journal of Rare Diseases* 8:31 (2013). Definitive diagnosis of TTR amyloidosis, however, typically relies on target organ biopsies, followed by histological staining of the excised tissue with the amyloid-specific dye, Congo red. If a positive test for amyloid is observed, immunohistochemical staining for TTR is subsequently performed to ensure that the precursor protein responsible for amyloid formation is indeed TTR. For familial forms of the diseases, demonstration of a mutation in the gene encoding TTR is then needed before a definitive diagnosis can be made.

The identification of the subject can occur in a clinical setting, or elsewhere, such as in the subject's home, for example, through the subject's own use of a self-testing kit. For example, the subject can be identified based on various symptoms such as peripheral neuropathy (sensory and motor), autonomic neuropathy, gastrointestinal impairment, cardiomyopathy, nephropathy, or ocular deposition. See Ando et al., *Orphanet Journal of Rare Diseases* 8:31 (2013). The subject can also be identified by increased levels of non-native forms of TTR in plasma samples from the subject compared to control samples, as disclosed in the examples.

As warranted by family history, genetic testing, or medical screening for TTR amyloidosis, treatment can begin at any age (e.g., 20, 30, 40, 50, 60, or 70 years of age). Treatment typically entails multiple dosages over a period of time and can be monitored by assaying antibody or activated T-cell or B-cell responses to a therapeutic agent (e.g., a truncated form of TTR comprising amino acid residues 89-97) over time. If the response falls, a booster dosage is indicated.

In prophylactic applications, an antibody or a pharmaceutical composition of the same is administered to a subject susceptible to, or otherwise at risk of a disease (e.g., TTR amyloidosis) in a regime (dose, frequency and route of administration) effective to reduce the risk, lessen the severity, or delay the onset of at least one sign or symptom of the disease. In therapeutic applications, an antibody or immunogen to induce an antibody is administered to a subject suspected of, or already suffering from a disease (e.g., TTR amyloidosis) in a regime (dose, frequency and route of administration) effective to ameliorate or at least inhibit further deterioration of at least one sign or symptom of the disease.

A regime is considered therapeutically or prophylactically effective if an individual treated subject achieves an outcome more favorable than the mean outcome in a control population of comparable subjects not treated by methods disclosed herein, or if a more favorable outcome is demonstrated for a regime in treated subjects versus control subjects in a controlled clinical trial (e.g., a phase II, phase II/III, or phase III trial) or an animal model at the $p<0.05$ or $0.01$ or even $0.001$ level.

An effective regime of an antibody can be used for, e.g., inhibiting or reducing aggregation of TTR in a subject having or at risk of a condition associated with TTR accumulation; inhibiting or reducing TTR fibril formation in a subject having or at risk of a condition associated with TTR accumulation; reducing or clearing TTR deposits or aggregated TTR in a subject having or at risk of a condition associated with TTR accumulation; stabilizing non-toxic conformations of TTR in a subject having or at risk of a condition associated with TTR accumulation; inhibiting toxic effects of TTR aggregates, fibrils or deposits in a subject having or at risk of a condition associated with TTR accumulation; diagnosing the presence or absence of TTR amyloid accumulation in a tissue suspected of comprising the amyloid accumulation; determining a level of TTR deposits in a subject by detecting the presence of bound antibody in the subject following administration of the antibody; detecting the presence of monomeric, misfolded, aggregated, or fibril forms of TTR in a subject; monitoring and evaluating the efficacy of therapeutic agents being used to treat patients diagnosed with a TTR amyloidosis; inducing an immune response comprising antibodies to TTR in a subject; delaying the onset of a condition associated with TTR amyloid accumulation in a subject; or treating or effecting prophylaxis of a TTR amyloidosis in a patient.

Effective doses vary depending on many different factors, such as means of administration, target site, physiological state of the subject, whether the subject is human or an animal, other medications administered, and whether treatment is prophylactic or therapeutic.

An exemplary dose range for antibodies can be from about 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Antibody can be administered in such doses daily, on alternative days, weekly, fortnightly, monthly, quarterly, or according to any other schedule determined by empirical analysis. An exemplary treatment entails administration in multiple doses over a prolonged period, for example, of at least six months. Additional exemplary treatment regimes entail administration once per every two weeks or once a month or once every 3 to 6 months.

Antibodies can be administered via a peripheral route. Routes of administration include topical, intravenous, oral, subcutaneous, intraarterial, intracranial, intrathecal, intraperitoneal, intranasal or intramuscular. Routes for administration of antibodies can be intravenous or subcutaneous. Intravenous administration can be, for example, by infusion over a period such as 30-90 min. This type of injection is most typically performed in the arm or leg muscles. In some methods, agents are injected directly into a particular tissue where deposits have accumulated, for example intracranial injection.

Pharmaceutical compositions for parenteral administration can be sterile and substantially isotonic (250-350 mOsm/kg water) and manufactured under GMP conditions. Pharmaceutical compositions can be provided in unit dose form (i.e., the dose for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with another agent effective in treatment or prophylaxis of the disease being treated. Such agents can include siRNA to inhibit expression of TTR or Vyndaqel, a stabilizer of TTR in tetramer formation.

After treatment, the subject's condition can be evaluated to determine the progress or efficacy of such treatment. Such methods preferably test for changes in TTR amyloid levels or levels of non-native forms of TTR. For example, TTR amyloid levels may be evaluated to determine improvement relative to the subject's TTR amyloid levels under comparable circumstances prior to treatment. The subject's TTR amyloid levels can also be compared with control populations under comparable circumstances. The control populations can be similarly afflicted, untreated subjects or normal untreated subjects (among other control subjects). Improvement relative to similarly afflicted, untreated subjects or levels approaching or reaching the levels in untreated normal subjects indicates a positive response to treatment.

TTR amyloid levels can be measured by a number of methods, including imaging techniques. Examples of suitable imaging techniques include PET scanning with radiolabeled TTR of fragments thereof, TTR antibodies or fragments thereof, Congo-red-based amyloid imaging agents, such as, e.g., PIB (US 2011/0008255), amyloid-imaging peptide p31 (Biodistribution of amyloid-imaging peptide, p31, correlates with amyloid quantitation based on Congo red tissue staining, Wall et al., Abstract No. 1573, 2011 ISNM Annual Meeting), and other PET labels. Levels of non-native forms of TTR can be measured, for example, by performing SDS-PAGE/Western blot or Meso Scale Discovery plate assays with the antibodies disclosed herein on plasma samples or biopsy samples from a subject and comparing to control samples, as described in the examples.

A. Diagnostics and Monitoring Methods

Also provided are methods of detecting an immune response against TTR in a patient suffering from or susceptible to diseases associated with TTR deposition or pathogenic forms of TTR (e.g., monomeric, misfolded, aggregated, or fibril forms of TTR). The methods can be used to monitor a course of therapeutic and prophylactic treatment with the agents provided herein. The antibody profile following passive immunization typically shows an immediate peak in antibody concentration followed by an exponential decay. Without a further dose, the decay approaches pre-treatment levels within a period of days to months depending on the half-life of the antibody administered. For example, the half-life of some human antibodies is of the order of 20 days.

In some methods, a baseline measurement of antibody to TTR in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting monomeric, misfolded, aggregated, or fibril forms of TTR in a subject, for example, by measuring TTR amyloid or pathogenic forms of TTR (e.g., monomeric, misfolded, aggregated, or fibril forms of TTR) in a sample from a subject or by in vivo imaging of TTR in a subject. Such methods are useful to diagnose or confirm diagnosis of diseases associated with such pathogenic forms of TTR (e.g., TTR amyloidosis), or susceptibility thereto. The methods can also be used on asymptomatic subjects. The presence of monomeric, misfolded, aggregated, or fibril forms of TTR indicates susceptibility to future symptomatic disease. The methods are also useful for monitoring disease progression and/or response to treatment in subjects who have been previously diagnosed with a TTR amyloidosis.

Biological samples obtained from a subject having, suspected of having, or at risk of having a TTR amyloidosis can be contacted with the antibodies disclosed herein to assess the presence of monomeric, misfolded, aggregated, or fibril forms of TTR. For example, levels of monomeric, misfolded, aggregated, or fibril forms of TTR in such subjects may be compared to those present in healthy subjects. Alternatively, levels of TTR amyloid or pathogenic forms of TTR (e.g., monomeric, misfolded, aggregated, or fibril forms of TTR) in such subjects receiving treatment for the disease may be compared to those of subjects who have not been treated for a TTR amyloidosis. Some such tests involve a biopsy of tissue obtained from such subjects. ELISA assays may also be useful methods, for example, for assessing levels of monomeric, misfolded, aggregated, or fibril forms of TTR in fluid samples. Some such ELISA assays involve anti-TTR antibodies that preferentially bind monomeric, misfolded, aggregated, or fibril forms of TTR relative to normal tetrameric forms of TTR.

The in vivo imaging methods can work by administering a reagent, such as antibody that binds to monomeric, misfolded, aggregated, or fibril forms of TTR in the subject, and then detecting the reagent after it has bound. Such antibodies typically bind to an epitope within residues 89-97 of TTR. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the subject, or via other routes deemed reasonable. The dose of reagent should be within the same ranges as for treatment methods. Typically, the reagent is labeled, although in some methods, the primary reagent with affinity for monomeric, misfolded, aggregated, or fibril forms of TTR is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. A decrease in values relative to base line generally signals a positive response to treatment.

IX. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

X. Other Applications

The antibodies can be used for detecting monomeric, misfolded, aggregated, or fibril forms of transthyretin (TTR), or fragments thereof, in the context of clinical diagnosis or treatment or in research. For example, the antibodies can be used to detect the presence of monomeric, misfolded, aggregated, or fibril forms of TTR in a biological sample as an indication that the biological sample comprises TTR amyloid deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of monomeric, misfolded, aggregated, or fibril forms of TTR) to the biological sample(s) is increased, decreased, or the same relative to antibody binding to the control sample(s). Increased binding of the antibody to the biological sample(s) relative to the control sample(s) indicates the presence of monomeric, misfolded, aggregated, or fibril forms of TTR in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of monomeric, misfolded, aggregated, or fibril forms of TTR in a biological sample to monitor and evaluate the efficacy of a therapeutic agent being used to treat a patient diagnosed with a TTR amyloidosis. A biological sample from a patient diagnosed with a TTR amyloidosis is evaluated to establish a baseline for the binding of the antibodies to the sample (i.e., a baseline for the presence of the monomeric, misfolded, aggregated, or fibril forms of TTR in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of monomeric, misfolded, aggregated, or fibril forms of TTR) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of monomeric, misfolded, aggregated, or fibril forms of TTR) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of monomeric, misfolded, aggregated, or fibril forms of TTR), it can be concluded that the therapeutic agent was effective in treating the TTR amyloidosis in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of TTR amyloidosis.

The antibodies can also be used as research reagents for laboratory research in detecting monomeric, misfolded, aggregated, or fibril forms of TTR, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify monomeric, misfolded, aggregated, or fibril forms of TTR, or binding partners of monomeric, misfolded, aggregated, or fibril forms of TTR, e.g., by affinity chromatography.

Antibody 9D5 has been deposited subject to the Budapest Treaty under accession number PTA-124078 on Apr. 4, 2017 at the American Type Culture Collection 10801 University Boulevard Manassas, Va. 20110 USA. All restrictions imposed by the depositor on the availability to the public of the deposited material will be irrevocably removed on the granting of a patent except as permitted under 37 CFR 1.808(b).

Antibody 14G8 has been deposited subject to the Budapest Treaty under accession number PTA-124079 on Apr. 4, 2017 at the American Type Culture Collection 10801 University Boulevard Manassas, Va. 20110 USA. All restrictions imposed by the depositor on the availability to the public of the deposited material will be irrevocably removed on the granting of a patent except as permitted under 37 CFR 1.808(b).

The antibodies can also be used for inhibiting or reducing aggregation of TTR, inhibiting or reducing TTR fibril formation, reducing or clearing TTR deposits or TTR aggregates, or stabilizing non-toxic conformations of TTR in a biological sample. The biological sample can comprise, for example, blood, serum, plasma, or tissue (e.g., tissue from the heart, peripheral nervous system, autonomic nervous system, kidneys, eyes, or gastrointestinal tract). In some instances, TTR aggregation, TTR fibril formation, or TTR deposits are inhibited or reduced by at least 10%, 20%, 25%, 30%, 40%, 50%, or 75%, (e.g., 10%-75% or 30%-70%). Assays for detecting fibril formation are described elsewhere herein. See also US 2014/0056904.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of mis-TTR Monoclonal Antibodies

Conformationally-specific monoclonal antibodies against monomeric, mis-folded, fibril, or aggregated forms of TTR (mis-TTR) were generated, screened, expressed, and purified as described in Materials and Methods (a-d). In order to generate mis-TTR monoclonal antibodies, the crystal structure of human tetrameric TTR was examined to find regions of the protein that are buried in the tetramer, but exposed upon dissociation of the tetramer into its monomeric subunits. The region identified was residues 89-97 (EHAEVVFTA) (SEQ ID NO: 113) located within the F strand of TTR and sequestered at the dimer interface of the tetrameric protein. A BLAST search of the protein database did not reveal any other human proteins possessing this sequence.

A peptide comprising this sequence (ggEHAEVVFTAggkg) (SEQ ID NO: 114), was synthesized. Capitalized letters represent residues 89-97 of TTR. Lower case letters represent additional linker residues added to increase the solubility of the antigenic peptide and to establish the 9 amino acid fragment as an internal sequence. This peptide was linked to a poly-lysine dendritic core, generating a multiple antigenic peptide immunogen (TTR-MAP) comprising a core of lysine residues with multiple branches linked to the TTR 89-97 peptide. The antibodies listed in Table 2 were generated against TTR-MAP.

In addition to this multiple antigenic peptide, two other immunogens containing the same TTR fragment were generated by covalently linking similar TTR 89-97 peptides (Ac-cggEHAEVVFTA-amide (SEQ ID NO: 115) and Ac-EHAEVVFTAcgg-amide (SEQ ID NO: 116)) via the N- and C-terminal cysteine residues to keyhole limpet hemocyanin (TTR89-97-N-KLH and TTR89-97-C-KLH).

Following antibody generation, screening, expression, and purification, detailed binding kinetic parameters (association rate ($k_a$), dissociation rate ($k_d$), and binding affinity constant ($K_D$)) were determined for lead mis-TTR antibodies by Surface Plasmon Resonance (SPR) for recombinant human TTR F87M/L110M, as shown in Table 2. Anti-mouse IgG (GE Healthcare) was immobilized on a sensor chip C5 (lacking dextran chains) via amine coupling following the instructions provided in the GE Healthcare anti-mouse kit, and mis-TTR mAbs were captured to a level to ensure a maximum binding of analyte of 30-50 RU. Various concentrations of analyte (recombinant human TTR F87M/L110M) were passed over the captured ligand at 30 μl/min in running buffer (HBS+0.05% P-20, 1 mg/mL BSA) in 3-fold dilutions. For each concentration, the reaction proceeded for a time frame allowing for the higher analyte concentrations to reach equilibrium during association, as well as at least 10% of signal to decay during dissociation. At least one concentration (not the highest or lowest) was run in duplicate. Concentration ranges of analyte were selected based on preliminary experimentation to span at least 10-fold above $K_D$ to 10-fold below $K_D$.

The results of SPR analysis of lead mis-TTR mAbs is shown in Table 2 below.

TABLE 2

SPR Analysis of Lead mis-TTR Antibodies Binding to Human TTR (F87M/L110M)

| mAb | $k_a$ (1/Ms) | $k_d$ (1/s) | $K_D$ (M) | $R_{max}$ |
|-----|--------------|-------------|-----------|-----------|
| 9D5 | 2.715E+4 | 4.930E−4 | 1.816E−8 | 31.55 |
| 14G8 | 2.880E+4 | 5.358E−4 | 1.861E−8 | 27.13 |
| 5A1 | 6.107E+4 | 4.693E−4 | 7.684E−9 | 30.98 |
| 6C1 | 4.607E+4 | 4.151E−4 | 9.010E−9 | 26.32 |

Example 2. Binding of mis-TTR Antibodies to TTR Antigen

Four lead mis-TTR mAbs (9D5, 14G8, 6C1, and 5A1) were assayed by ELISA at concentrations ranging from 0.31 to 2.5 μg/ml using both pH4.0-treated TTR (pH4-TTR) and native TTR as the coating antigen. TTR antigen preparation and ELISA protocols are described elsewhere in Materials and Methods (e-g).

Figure 3B:
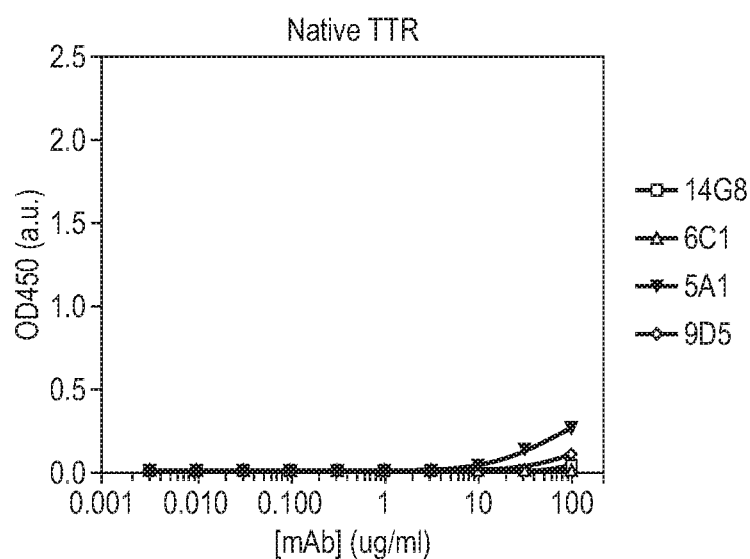

The resulting binding curves and tabulated $K_d$ and $B_{max}$ values are shown in FIG. 3 and Table 3 below. The results in FIG. 3 are presented in arbitrary units (a.u.) on the y-axis. All mAbs showed significant binding to pH4-TTR with $K_d$ values ranging from 16 nM (6C1) to 282 nM (9D5). $B_{max}$ values for binding to pH4-TTR ranged from a low of 0.65 a.u. (14G8) to a high of 2.02 (9D5). In contrast to the binding to pH4-TTR, none of the antibodies showed significant binding to native TTR, indicating that all TTR antibodies generated were specific for non-native forms of TTR.

TABLE 3

| ELISA Analysis of Lead mis-TTR Antibodies Binding to pH4-TTR | | |
|---|---|---|
| mAb | $K_d$ (nM) | $B_{max}$ (a.u.) |
| 9D5 | 282 | 2.02 |
| 14G8 | 108 | 0.65 |
| 6C1 | 16 | 1.07 |
| 5A1 | 23 | 1.61 |

Example 3. Analysis of mis-TTR Antibodies by SDS-PAGE and Native-PAGE

9D5 and 14G8 were analyzed by SDS-PAGE/Western to demonstrate specificity of binding toward monomeric/denatured forms of TTR versus native, non-denatured TTR. SDS-PAGE, Native-PAGE, and Western Blot protocols are described elsewhere in the Methods and Materials (h-j).

Non-denatured TTR or pH4-TTR was run on an SDS-PAGE gel alongside heat-denatured TTR and heat-denatured pH4-TTR. After electrophoresis, the gel was Western blotted onto nitrocellulose and stained with TTR mAbs 9D5 and 14G8. Both antibodies only recognized TTR when it was treated at pH4 or when TTR or pH4-TTR was first heat-denatured prior to SDS-PAGE. These 9D5 and 14G8 thus show a specificity for TTR conformers generated either by denaturation of TTR or by treatment of TTR at pH4.

6C1 and 5A1 along with total TTR mAbs (7G7, 8C3) and the commercially available Sigma polyclonal antibody were also analyzed by SDS-PAGE/Western. Each blot contained stained molecular weight markers, non-denatured TTR, and pH4-TTR.

The stained SDS-PAGE gel showed that the major species present in the non-denatured TTR sample was an ~38 kDa dimer. In contrast, the major component present in the pH4-TTR sample ran as an ~35 kDa dimer with a small amount of dimer of an ~15 kDa monomer. This dimer ran as a slightly smaller protein than the dimer present in the non-denatured TTR sample, indicating a conformational difference between these two TTR dimer species.

The Western blots of TTR and pH4-TTR using the four mis-TTR antibodies showed that these mAbs do not recognize non-denatured TTR, but do bind to both the denatured monomer and dimer present in the pH4-TTR sample. Thus, the four mis-TTR mAbs (9D5, 14G8, 6C1, and 5A1) show similar specificities for non-native conformations of TTR when analyzed by SDS-PAGE/Westerns.

In contrast to the four mis-TTR mAbs, the two TTR control mAbs, 7G7 and 8C3, generated through immunization of mice with intact TTR recognized all TTR species present in the TTR and pH4-TTR samples, including tetrameric TTR species. Thus unlike the mis-TTR mAbs, these control mAbs bind TTR but with no conformational specificity. The Sigma polyclonal antibody behaved similarly to the 7G7 and 8C3 control mAbs.

TTR and pH4-TTR were also run on a native gel to see if the four mis-TTR mAbs were capable of showing conformation specificity under non-denaturing gel conditions. On a stained native PAGE gel, TTR ran as an ~35 kDa native dimer with a small amount of tetramer. In contrast, pH4-TTR ran primarily as a high molecular-weight smear with a trace amount of the ~35 kDa dimer. The non-specific Sigma polyclonal antibody recognized all TTR species present in both the TTR and the pH4-TTR sample. In contrast, 9D5 only recognized the high molecular weight TTR species present in the pH4-TTR sample. As observed in the SDS-PAGE/Western study, 9D5 did not recognize any of the native TTR species.

All four mis-TTR mAbs were subsequently analyzed by native-PAGE/Western blot. As expected and similar to 9D5, the other mis-TTR mAbs, 14G8, 6C1, and 5A1, specifically bound to the high molecular weight non-native forms of TTR present in the pH4-TTR sample. None of these antibodies recognized the ~35 kDa native TTR dimer. These results indicate that the four mis-TTR mAbs behave similarly and recognize only non-native TTR species that are conformationally distinct from native TTR.

Example 4. Inhibition of TTR Fiber Formation by mis-TTR Antibodies

TTR-Y78F is a TTR variant containing a point mutation at position 78 in the protein sequence that destabilizes the TTR tetramer. With time and under mildly acidic conditions, this TTR variant dissociates into its monomeric subunits which can then go on to aggregate and form fibers capable of binding to thioflavin-T. The extent of fiber formation can thus be monitored by measuring thioflavin-T fluorescence at 480 nm. Introduction of a mis-TTR antibody specific for dissociated TTR monomers or aggregates would prevent the assembly of TTR fibers resulting in a decrease in thioflavin-T fluorescence relative to a no-antibody control reaction. Protocols for examining inhibition of TTR fiber formation are described elsewhere in the Materials and Methods (k).

Figure 4A:
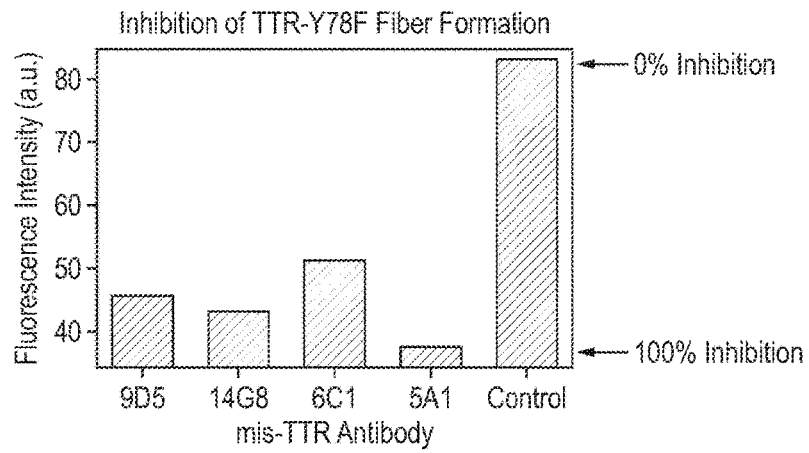
FIGS. 4A, 4B & 4C.

All four mis-TTR antibodies strongly inhibited the formation of thioflavin-T reactive TTR-Y78F fibers relative to the isotype control. The results are shown in FIG. 4A and are presented in arbitrary units (a.u.) on the y-axis. Mis-TTR antibody 5A1 almost completely inhibited fiber formation. These results are consistent with the notion that mis-TTR antibodies bind monomeric and/or aggregated forms of TTR, thereby preventing the formation of TTR fibers.

Table 4 summarizes the characterization data obtained for the set of 4 mis-TTR antibodies (9D5, 14G8, 6C1, and 5A1) that showed good conformational selectivity for non-native forms of TTR. These antibodies had affinities ($K_D$) for pH4-TTR ranging from 14.5 nM (6C1) to 257 nM (9D5) and $B_{max}$ values ranging from 0.65 a.u. (14G8) to 2.02 (9D5). None of these antibodies recognized native TTR, but did bind to pH4-TTR on an SDS-PAGE/Western and to the high molecular weight TTR aggregates on a native-PAGE/Western. These antibodies also inhibited the formation of TTR fibrils in the fibril formation assay using Thio-T as the read-out.

TABLE 4 mis-TTR-Y78F mAb Characterization Summary Table

| | Sandwich ELISA (pH4-TTR) | | Western Blot | | % Inh. Fibrils |
|---|---|---|---|---|---|
| | $K_D$ | $B_{max}$ | SDS-PAGE | | Native |  |
| Clone ID | (nM) | (OD$_{450}$ a.u.) | (TTR) | (pH4-TTR) | (HMW-TTR) | (Thio-T) |
| 9D5 | 257 | 2.02 | − | +++ | +++ | 83 |
| 14G8 | 98.7 | 0.65 | − | +++ | ++ | 65 |

TABLE 4-continued mis-TTR-Y78F mAb Characterization Summary Table

| Clone ID | Sandwich ELISA (pH4-TTR) | | Western Blot | | | % Inh. Fibrils |
|---|---|---|---|---|---|---|
| | $K_D$ (nM) | $B_{max}$ (OD$_{450}$ a.u.) | SDS-PAGE (TTR) | SDS-PAGE (pH4-TTR) | Native (HMW-TTR) | (Thio-T) |
| 6C1 | 14.6 | 1.07 | – | +++ | +++ | 72 |
| 5A1 | 21.3 | 1.61 | – | +++ | +++ | 100 |

Figure 4B:
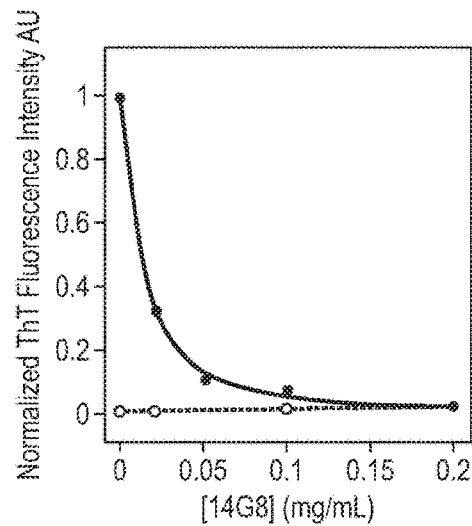
Figure 4C:
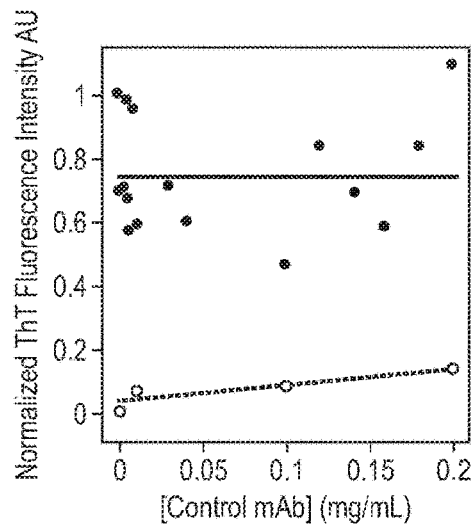

TTR-V122I is a TTR variant containing a single point mutation at position 122 that destabilizes the tetramer. Fibril formation was associated with an increase in ThT fluorescence Increasing 14G8 mAb concentrations caused a monotonic decrease in ThT fluorescence indicating a substoichiometric inhibition of TTR fibrillation (IC$_{50}$=0.028±0.009 mg/mL; n=3; FIG. 4B and Table 4a). The isotype control mAb did not cause inhibition of TTR fibrillation (FIG. 4C), thus demonstrating the specificity of 14G8 mediated inhibition.

Comparable substoichiometric IC$_{50}$ values determined for 5A1 and 6C1 (Table 4a) suggested analogous mechanisms of fibril inhibition for each of these mis-TTR mAbs. In contrast, 9D5 unexpectedly failed to inhibit TTR-V122I fibril formation, despite showing similar specificity and affinity for non-native TTR. It remains to be explored whether 9D5 is more sensitive to the assay conditions used.

TABLE 4a mis-TTR-V122I mAb Characterization Summary Table

| Antibody | IC$_{50}$ ± SD (mg/mL) |
|---|---|
| 9D5 | No inhibition |
| 14G8 | 0.028 ± 0.009 |
| 6C1 | 0.048 ± 0.059 |
| 5A1 | 0.015 ± 0.02 |
| EG 27/1 | No inhibition |

Example 5. Immunohistochemical (IHC) Characterization of ATTR Tissue Using mis-TTR mAbs The lead mis-TTR mAbs raised to the TTR 89-97 fragment of the transthyretin protein were immunohistochemically tested on fresh frozen and paraffin processed tissue from confirmed TTR cardiac amyloidosis patients. Protocols for obtaining and preparing cardiac tissue samples, immunohistochemistry (IHC), and image analysis, are provided elsewhere in the Materials and Methods (l-o). The antibodies used for IHC are described in Table 5.

TABLE 5

Antibodies Used for Immunohistochemical Characterization

| Antibody | Antibody Type | Vendor | Stain Cardiac Tissue | Concentration |
|---|---|---|---|---|
| 14G8 | mis-TTR | Prothena Biosciences | Yes | 0.5 µg/mL |
| 9D5 | mis-TTR | Prothena Biosciences | Yes | 0.5 µg/mL |
| 6C1 | mis-TTR | Prothena Biosciences | Yes | 0.5 µg/mL |
| 5A1 | mis-TTR | Prothena Biosciences | Yes | 0.5 µg/mL |
| 7G7 | TTR | Prothena Biosciences | Yes | 0.5 µg/mL |
| 6F10 | Isotype Control | Prothena Biosciences | No | 0.5 µg/mL |
| Prealbumin (A0002) | TTR | Dako North America | Yes | 1:2,000 & 1:20,000 |
| Kappa Light Chains (A0191) | LC-κ | Dako North America | No | 1:8,000 |
| Lambda Light Chains (A0193) | LC-λ | Dako North America | No | 1:8,000 |
| Amyloid A (M0759) | AA | Dako North America | No | 1:8,000 |

Cardiac tissue samples were obtained from patients with confirmed diagnoses of ATTR mutations. Demographics for cases examined immunohistochemically were as follows and are summarized in Table 6: FAC=familial amyloidotic cardiomyopathy; FAP=familial amyloidotic polyneuropathy; 1° AL=light-chain amyloidosis; ATTR=transthyretin-mediated amyloidosis; Unk=Unknown

TABLE 6

Immunohistochemical Staining of Cardiac Tissue Samples with mis-TTR Antibodies

| Case | Diagnosis | TTR Mutations | Format | Stained with TTR Antibodies? |
|---|---|---|---|---|
| Patient 1 | FAC | Ileu122 | Frozen | Yes |
| Patient 2 | FAP | Wild type | Frozen | Yes |
| Patient 3 | FAP | 84Ser | Frozen | Yes |
| Patient 4 | FAP | 84Ser | Frozen | Yes |
| Patient 5 | 1° AL | — | Frozen | No |
| Patient 6 | 1° AL | — | Frozen | No |
| Patient 7 | ATTR | 10Arg | Frozen | Yes |
| Patient 8 | ATTR | V122I | Frozen | Yes |
| Patient H1 | ATTR | Val122Ile | FFPE | Yes |
| Patient H2 | ATTR | Thr60Ala | FFPE | Yes |
| Patient H3 | ATTR | Thr49Ala | FFPE | Yes |
| Patient H4 | ATTR | Ile84Ser | FFPE | Yes |
| Patient H5 | Unk. | Senile Cardiac | FFPE | Yes |
| Patient H6 | ATTR | Ile84Ser | FFPE | Yes |

Mouse monoclonal antibodies (mis-TTR mAbs) raised to the 89-97 fragment of the transthyretin protein were immunohistochemically tested on fresh frozen and paraffin processed tissue from confirmed TTR cardiac amyloidosis patients. Each mis-TTR antibody showed strong immunoreactivity on ATTR cardiac tissue. Dark staining was observed in deposits throughout the myocardium and the vasculature. When immunoreactivity was compared to staining with Congo Red of Thioflavin-T, the majority of the immunoreactivity in the tissue showed high congruence with Congo red birefringence and Thioflavin T-positive staining. This confirms the beta pleated sheet nature of the TTR amyloid deposited in this tissue. 14G8, 9D5, 6C1, and 5A1 also detected pre-amyloid TTR present in areas of the myocardium that were TTR-immunopositive but Congo red or Thioflavin T-negative. Both the IgG-isotype control antibody and primary antibody omission sections were negative for staining across all tissues tested. Antibodies reactive toward other amyloidogenic proteins (lambda and kappa light chains or amyloid A) were non-reactive toward the ATTR cardiac tissue used in this analysis, indicating that deposits were specifically TTR in nature.

The staining patterns of mis-TTR antibodies were compared to that obtained with a well-characterized commercial TTR reference antibody (prealbumin, A0002; Dako; Carpinteria, Calif.). The DAKO reference antibody stained the diseased myocardium in the same areas as the mis-TTR antibodies, but produced a more diffuse staining pattern. The DAKO reference antibody did not stain the congophillic TTR amyloid deposits present on the vasculature as strongly as the mis-TTR antibodies.

The mis-TTR antibodies did not stain normal, non-disease tissue. Furthermore, as expected, staining with an isotype control antibody, 6F10, was also negative.

In order to determine if the reactivity of mis-TTR antibodies was specific for TTR deposits, cross reactivity of these antibodies toward cardiac tissue derived from patients diagnosed with primary AL amyloidosis was examined. As expected, no staining of AL amyloid tissue was observed, confirming that TTR antibodies react specifically toward ATTR diseased tissue.

Cardiac tissue from patients with confirmed diagnoses of senile systemic amyloidosis or from patients with confirmed FAC, or FAP caused by point mutations in the TTR gene also stained positively with 14G8, 9D5, 6C1, and 5A1. These results indicate that mis-TTR antibodies have the ability to recognize TTR deposits in cardiac tissue regardless of the ATTR genotype.

Other non-cardiac tissues known to express TTR were also examined for staining by mis-TTR antibodies and compared to the staining obtained using the DAKO reference antibody. As expected, the liver, pancreas and choroid plexus all stained positively for TTR using the Dako reference antibody. In contrast, 14G8 only stained the pancreatic alpha cells located in the islets of Langerhans and the choroid plexus, suggesting that some of the TTR localized to these organs are conformationally distinct from TTR expressed in the liver. The lack of mis-TTR mAb immunoreactivity in the liver suggests that the large amount of TTR expressed there is primarily tetrameric, native TTR and does not have the exposed mis-TTR epitope. Similar results were obtained when the same tissues were stained with 9D5, 6C1, and 5A1.

Example 6. Analysis of ATTR vs Normal Human Plasma by SDS-PAGE/Western Blot and by Meso Scale Discovery (MSD) Plate Assay Six plasma samples from patients confirmed for V30M ATTR (Sample #11, #12, #15, #18, #19, #20) and 6 samples from normal subjects (#21, #22, #23, #24, #25, #27) were obtained from M. Saraiva (Porto University, Portugal). Sample #C6 was a normal human serum sample obtained from a commercial source (BioreclamationIVT). Samples were analyzed by SDS-PAGE and Western blot, or by MesoScale Discovery (MSD) Plate Assay. Protocols for these assays are described elsewhere in the Materials and Methods (p-r). A standard curve was generated for the MSD Plate Assay using 6C1.

In the resulting Western blots using the 9D5 and the 5A1 mis-TTR mAbs, differences in banding patterns between normal and TTR-V30M diseased plasma samples could be detected. All plasma samples contained an ~14 kDa TTR band that co-migrated with the non-native TTR monomer present in the pH4-TTR reference sample. In general, plasma samples derived from TTR-V30M patients (#21, 22, 23, 24, 25, & 27) had more of this monomeric mis-TTR species. In addition, plasma samples derived from V30M patients also contained an ~30 kDa band that co-migrated with the non-native TTR dimer present in the pH4-TTR reference sample. With the exception of samples #12 and #18, plasma samples derived from normal individuals possessed less of this dimer species.

Figure 5A:
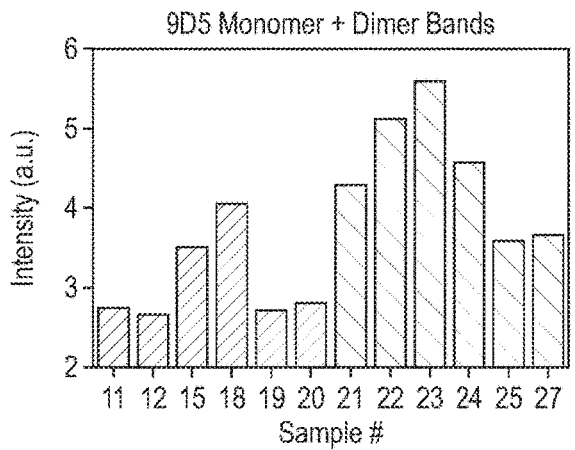
FIGS. 5A & 5B.
Figure 5B:
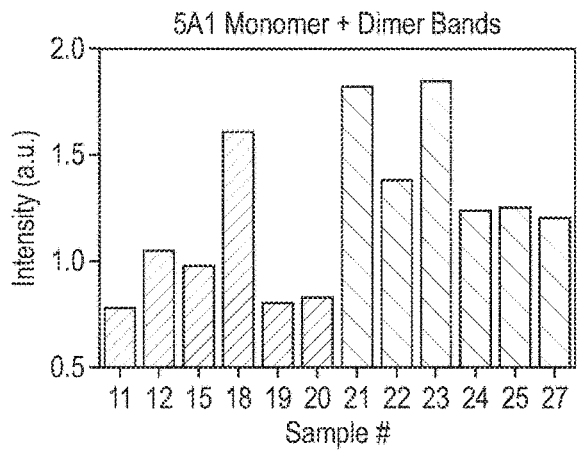

The above Western blots were scanned and the intensities of the combined 9D5- or 5A1-reactive TTR dimer and monomer bands were plotted for each sample. The results are shown in FIG. 5A (9D5) and 5B (5A1) and are presented in arbitrary units (a.u.) on the y-axis. With the exception of plasma samples #15 and #18, plasma samples derived from normal individuals (11, 12, 19, and 20) contained less 9D5- and 5A1-reactive dimer and monomer species than samples derived from V30M patients (21-25 and 27).

Figure 6:
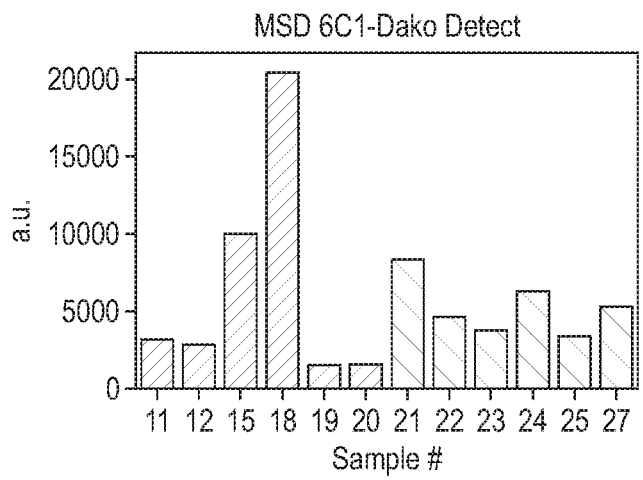
FIG. 6 depicts a MesoScale Discovery (MSD) plate assay of plasma samples from patients confirmed for V30M ATTR (Sample #11, #12, #15, #18, #19, #20) and samples from normal subjects (#21, #22, #23, #24, #25, #27) using the 6C1 antibody.

The 12 serum samples analyzed by 9D5 and 5A1 Western blot were also analyzed by MSD plate assay using 6C1 as the mis-TTR capture antibody and the Dako-SulfoTag antibody as the detection antibody. Results of these MSD assays are shown in FIG. 6 and are presented in arbitrary units (a.u.) on the y-axis. Samples 11, 12, 15, 18, 19, and 20 represent normal plasma. Samples 21-25 and 27 represent V30M diseased plasma.

With the exception of plasma samples #15 and #18, the amount of 6C1-reactive TTR present in plasma samples derived from normal individuals was lower than that observed in plasma from TTR-V30M diseased individuals. The levels of 6C1 reactivity measured by MSD assay correlated very well with the amount of 9D5 reactive dimer and monomer observed above by SDS-PAGE/Western.

In order to determine the concentration of the reactive TTR species present in plasma samples, the same samples were re-assayed using 6C1 as the capture antibody and 8C3-SulfoTag as the detection antibody. MSD signals were converted to ng/ml concentrations of reactive TTR species using the TTR F87M/L110M standard curve generated above. Based on this analysis, the average concentration of 6C1-reactive TTR present in the control samples was 271+/−185 ng/ml. In contrast, the average concentration of reactive TTR present in the V30M diseased plasma samples was higher, at 331+/−95 ng/ml. Taken together, these MSD results suggest that mis-TTR antibodies are capable of distinguishing between ATTR disease versus normal plasma. This warrants further development of mis-TTR antibodies for use in diagnostic assays of ATTR disease.

Example 7. Design of Humanized 9D5 Antibodies

The starting point or donor antibody for humanization was the mouse antibody 9D5. The heavy chain variable amino acid sequence of mature m9D5 is provided as SEQ ID NO: 1. The light chain variable amino acid sequence of mature m9D5 is provided as SEQ ID NO: 16. The heavy chain CDR1, CDR2, and CDR3 amino acid sequences are provided as SEQ ID NOS: 13-15, respectively (as defined by Kabat). A composite Chothia-Kabat CDR-H1 is provided as SEQ ID NO: 117. The light chain CDR1, CDR2, and CDR3 amino acid sequences are provided as SEQ ID NOS: 24-26, respectively (as defined by Kabat). Kabat numbering is used throughout in this Example.

The variable kappa (Vk) of m9D5 belongs to mouse Kabat subgroup 2, which corresponds to human Kabat subgroup 3. The variable heavy (Vh) of m9D5 belongs to mouse Kabat subgroup 3d, which corresponds to Kabat subgroup 3. See Kabat et al. Sequences of Proteins of Immunological Interest, Fifth Edition. NIH Publication No. 91-3242, 1991. The 16-residue CDR-L1 belongs to canonical class 4, the 7-residue CDR-L2 belongs to canonical class 1, and the 9-residue CDR-L3 belongs to canonical class 1 in Vk. See Martin & Thornton, J. Mol. Biol. 263:800-15, 1996. The 10-residue composite Chothia-Kabat CDR-H1 belongs to canonical class 1, and the 17-residue CDR-H2 belongs to canonical class 1. See Martin & Thornton, J Mol. Biol. 263:800-15, 1996. The CDR-H3 has no canonical classes.

The residues at the interface between the Vk and Vh domains are the ones commonly found, except that Leu is at position 47 in heavy chain, whereas Tyr typically is that this position. This position is a candidate for backmutation.

A search was made over the protein sequences in the PDB database (Deshpande et al., Nucleic Acids Res. 33: D233-7, 2005) to find structures which would provide a rough structural model of 9D5. The crystal structure of antibody fab (pdb code 1MJU) (Ruzheinikov et al., J. Mol. Biol. 332(2):423-435, 2003) was used for the Vk structure since it had good resolution (1.22 A) and overall sequence similarity to 9D5 Vk, retaining the same canonical structure for the loop as 9D5. A monomeric antibody with pdb code 1SEQ (Covaceuszach et al., Acta Crystallogr. D Biol. Crystallogr. 57 (PT 9), 1307-1309, 2001) was used for the Vh structure since it had good sequence similarity and resolution (2.0 A), and it has the same canonical structures for CDR-H1 and CDR-H2 as that of 9D5 VH. We modeled 9D5 Vh chain using the 1MQK structure as well, since it has a better resolution of 1.28 A (Ostermeier et al., Proteins 21(1):74-77, 1995). BioLuminate software (licensed from Schrodinger Inc.) was used to model a rough structure of 9D5.

A search of the non-redundant protein sequence database from NCBI allowed selection of suitable human frameworks into which to graft the murine CDRs. For Vh, human Ig heavy chain BAC02114 (GI: 21670209) (SEQ ID NO: 3) was chosen (Akahori et al., Construction and characterization of antibody libraries: isolation of therapeutic human antibodies and application to functional genomics, Direct Submission, Jul. 25, 2001). It shares the canonical forms of 9D5. It is a member of Kabat human heavy subgroup 1. 9D5 Vh has some unique framework residue and any human framework acceptor did not show very high homology. Therefore, we used a second Framework, AAX82494 (GI: 62421461) (SEQ ID NO: 4) (Lundquist et al., Infect. Immun. 74(6), 3222-3231, 2006) as well to make a hybrid acceptor framework. For Vk, a human kappa light chain with NCBI accession code ABC66952 (GI: 84798006) (Shriner et al., Vaccine 24(49-50):7159-7166, 2006) was chosen (SEQ ID NO: 18). It has the same canonical classes for CDR-L1 and L2 as that for the parental Vk. It is a member of Kabat human kappa subgroup 2.

Eight humanized heavy chain variable region variants and five humanized light chain variable region variants were constructed containing different permutations of substitutions (Hu9D5VHv1, 2, 2b, 3, 3b, 4, 4b, and 5 (SEQ ID NOS: 5-12, respectively) and Hu9D5VLv1-5 (SEQ ID NOS: 19-23, respectively)) (FIGS. 12A-E and FIGS. 13A-D). The exemplary humanized Vh and Vk designs, with backmutations and other mutations based on selected human frameworks, are shown in FIGS. 12A-E and FIGS. 13A-D, respectively. The gray-shaded areas in the first column in FIGS. 12A-E and FIGS. 13A-D indicate the CDRs as defined by Chothia, and the gray-shaded areas in the remaining columns in FIGS. 12A-E and FIGS. 13A-D indicate the CDRs as defined by Kabat. SEQ ID NOS: 5-12 and 19-23 contain backmutations and other mutations as shown in Table 7. The amino acids at positions H42, H47, H69, H82, H82(b), H108, L8, L9, L18, L19, L36, L39, L60, L70, and L74 in Hu9D5VHv1, 2, 2b, 3, 3b, 4, 4b, and 5 and Hu9D5VLv1-5 are listed in Tables 8 and 9.

TABLE 7

$V_H$, $V_L$ Backmutations and Other Mutations

| $V_H$ or $V_L$ Variant | $V_H$ or $V_L$ Exon Acceptor Sequence | Donor Framework Residues |
|---|---|---|
| Hu9D5VHv1 (SEQ ID NO: 5) | NCBI accession codes BAC02114 and AAX82494 (SEQ ID NOS: 3 and 4, respectively) | H47, H69, H82 |
| Hu9D5VHv2 (SEQ ID NO: 6) | NCBI accession codes BAC02114 and AAX82494 (SEQ ID NOS: 3 and 4, respectively) | H47, H69, H82, H82b |
| Hu9D5VHv2b (SEQ ID NO: 7) | NCBI accession codes BAC02114 and AAX82494 (SEQ ID NOS: 3 and 4, respectively) | H42, H47, H108 |
| Hu9D5VHv3 (SEQ ID NO: 8) | NCBI accession codes BAC02114 and AAX82494 (SEQ ID NOS: 3 and 4, respectively) | H69, H82, H82b |
| Hu9D5VHv3b (SEQ ID NO: 9) | NCBI accession codes BAC02114 and AAX82494 (SEQ ID NOS: 3 and 4, respectively) | H47, H108 |
| Hu9D5VHv4 (SEQ ID NO: 10) | NCBI accession codes BAC02114 and AAX82494 (SEQ ID NOS: 3 and 4, respectively) | H82, H82b |
| Hu9D5VHv4b (SEQ ID NO: 11) | NCBI accession codes BAC02114 and AAX82494 (SEQ ID NOS: 3 and 4, respectively) | H47, H108 |
| Hu9D5VHv5 (SEQ ID NO: 12) | NCBI accession codes BAC02114 and AAX82494 (SEQ ID NOS: 3 and 4, respectively) | H42, H47, H82b |

TABLE 7-continued

V_H, V_L Backmutations and Other Mutations

| V_H or V_L Variant | V_H or V_L Exon Acceptor Sequence | Donor Framework Residues |
|---|---|---|
| Hu9D5VLv1 (SEQ ID NO: 19) | NCBI accession code ABC66952 (SEQ ID NO: 18) | L36 |
| Hu9D5VLv2 (SEQ ID NO: 20) | NCBI accession code ABC66952 (SEQ ID NO: 18) | None |
| Hu9D5VLv3 (SEQ ID NO: 21) | NCBI accession code ABC66952 (SEQ ID NO: 18) | L60 |
| Hu9D5VLv4 (SEQ ID NO: 22) | NCBI accession code ABC66952 (SEQ ID NO: 18) | L8, L9, L19, L36, L39, L60, L70, L74 |
| Hu9D5VLv5 (SEQ ID NO: 23) | NCBI accession code ABC66952 (SEQ ID NO: 18) | L8, L9, L18, L19, L36, L39, L60, L70, L74 |

TABLE 8

Kabat Numbering of Framework Residues for Backmutations and Other Mutations in Vh Regions of Humanized 9D5 Antibodies

| Residue | BAC02114 Heavy Chain | AAX82494 Heavy Chain | Mouse 9D5 | Hu9D5 VHv1 | Hu9D5 VHv2 | Hu9D5 VHv2b | Hu9D5 VHv3 | Hu9D5 VHv3b | Hu9D5 VHv4 | Hu9D5 VHv4b | Hu9D5 VHv5 |
|---|---|---|---|---|---|---|---|---|---|---|---|
| H42 | G | D | E | G | G | E | G | G | G | G | E |
| H47 | W | W | L | L | L | L | W | L | W | L | L |
| H69 | I | I | F | F | F | I | F | I | I | I | I |
| H82 | M | M | M | S | S | M | S | M | S | M | M |
| H82b | S | S | S | S | L | S | L | S | L | S | L |
| H108 | T | T | T | T | T | L | T | L | T | L | T |

TABLE 9

Kabat Numbering of Framework Residues for Backmutations and Other Mutations in Vk Regions of Humanized 9D5 Antibodies

| Residue | ABC66952 Light Chain | Mouse 9D5 | Hu9D5 VLv1 | Hu9D5 VLv2 | Hu9D5 VLv3 | Hu9D5 VLv4 | Hu9D5 VLv5 |
|---|---|---|---|---|---|---|---|
| L8 | P | A | P | P | P | A | A |
| L9 | L | P | L | L | L | P | P |
| L18 | P | S | P | P | P | P | S |
| L19 | A | V | A | A | A | V | V |
| L36 | Y | F | F | Y | Y | F | F |
| L39 | K | R | K | K | K | R | R |
| L60 | D | D | D | D | S | S | S |
| L70 | D | A | D | D | D | A | A |
| L74 | K | R | K | K | K | R | R |

An alignment of the murine 9D5 Vh sequence (SEQ ID NO: 1) with the mouse model sequences (1SEQ_H and 1MQK_H; SEQ ID NOS: 2 and 62, respectively), the human acceptor sequences (BAC02114 and AAX82494; SEQ ID NOS: 3 and 4, respectively), and the Hu9D5VHv1, Hu9D5VHv2, Hu9D5VHv2b, Hu9D5VHv3, Hu9D5VHv3b, Hu9D5VHv4, Hu9D5VHv4b, and Hu9D5VHv5 sequences (SEQ ID NOS: 5-12, respectively), is shown in FIG. 1A. The CDRs as defined by Kabat are enclosed in boxes, except that the first enclosed box is a composite of the Chothia CDR-H1 and the Kabat CDR-H1, with the Kabat CDR-H1 underlined and bolded. Positions at which canonical, vernier, or interface residues differ between mouse and human acceptor sequences are candidates for substitution. Examples of vernier/CDR foundation residues include residues 2, 49, 69, 71, 75, 80, and 94 by Kabat numbering in FIGS. 12A-E. Examples of canonical/CDR interacting residues include residues 24, 48, and 73 by Kabat numbering in FIGS. 12A-E. Examples of interface/packing (VH+VL) residues include residues 37, 39, 44, 47, 91, 93, and 103 by Kabat numbering in FIGS. 12A-E.

An alignment of the murine 9D5 Vk sequence (SEQ ID NO: 16) with the mouse model sequence (1MJU_L; SEQ ID NO: 17), the human acceptor sequence (ABC66952; SEQ ID NO: 18), and the Hu9D5VLv1, Hu9D5VLv2, Hu9D5VLv3, Hu9D5VLv4, and Hu9D5VLv5 sequences (SEQ ID NOS: 19-23, respectively), is shown in FIG. 1B. The CDRs as defined by Kabat are enclosed in boxes, except that the first enclosed box is a composite of the Chothia CDR-H1 and the Kabat CDR-H1, with the Kabat CDR-H1 underlined and bolded. Positions at which canonical, vernier, or interface residues differ between mouse and human acceptor sequences are candidates for substitution. Examples of vernier/CDR foundation residues include residues 4, 35, 46, 49, 66, 68, and 69 by Kabat numbering in FIGS. 13A-D. Examples of canonical/CDR interacting residues include residues 2, 48, 64, and 71 by Kabat numbering in FIGS. 13A-D. Examples of interface/packing (VH+VL) residues include residues 36, 38, 44, 47, 87, and 98 by Kabat numbering in FIGS. 13A-D.

The rationales for selection of the positions indicated in Tables 7 and 9 in the light chain variable region as candidates for substitution are as follows.

P8A: The model shows a kink in the loop at this position, so a backmutation to A was tried to alleviate this.

L9P: The model shows a kink in the loop at this position, so a backmutation to P was tried to alleviate this.

P18S: P at this position is less frequent. Mutation to S was tried to alleviate loop distortion.

A19V: A and V at this position are equally frequent. Mutation to V was tried to alleviate loop distortion.

Y36F: This is an interface residue, and typically Y or F. Y has an extra hydroxyl group that could potentially affect LC+HC packing. Polarity of the Y36 could potentially interfere with placement of heavy chain CRD-H3 residue H95. A homology model shows that Y at this position will form a de-novo H-bond with F100(g) in H3 that may result in mobility restriction of H3. Both F and Y were used in separate versions.

K39R: R forms H-bonds with adjoining residues in this loop as compared to K. To rule out any effects on loop stability, mutation to R was tried.

D60S: The presence of D at this residue shows high exposure for proteolysis. In some versions it was replaced with S, a residue most frequent in human germ line at this position. This is predicted to enhance stability.

D70A: D has proteolysis potential, so mutation to A was tried.

K74R: R appears to stabilize the loop compared to K at this position, so backmutation to R was tried.

The rationales for selection of the positions indicated in Tables 7 and 8 in the heavy chain variable region as candidates for substitution are as follows.

G42E: E makes ionic interactions with R at position 44. To rule out any effect that these interactions might have, backmutation to E was tested in some versions.

W47L: This is an interface residue, typically W. In murine 9D5 heavy chain, it is L, whereas in the human accepter framework there is W at this position. Although L and W are both non-polar, the phenolic ring in W could potentially impact light chain:heavy chain packing. W and L were included in separate versions.

I69F: This is a vernier residue, part of the CDR-H2 foundation. According to the homology model, the aromatic ring of F in murine sequences makes a pie stack with the aromatic ring of CRD-H2 residue Y59. An I residue at this position disturbs that stacking. I and F were included in separate versions.

M82S: M at this position is very rare in human frameworks. More common are A or N. Changing the residue to the more common S might reduce immunogenicity that could be associated with the rare M at this position. Based upon model observations, there is a possibility that M interacts with Leu80, which is a vernier zone residue. M and S were included in separate versions.

S82(b)L: S is present at this position in both the murine and human framework sequences, but S at this position is less frequent. Judging from the position where this residue sits in the model, it possibly could make contact with the antigen. Residues in framework region 3 of the heavy chain are known to occasionally contribute towards binding. S and L were included in separate versions.

T108L: L is the most frequent residue in human frameworks at this position, so L was tried in some versions.

Because two human acceptor frameworks (BAC02114 and AAX82494.1 (SEQ ID NOS: 3 and 4)) were used for humanization of the 9D5 heavy chain variable region, there are certain framework positions that have different amino acids in the two acceptor frameworks. Humanized versions of the 9D5 heavy chain variable region can include either amino acid at these residues. Examples of residues in which these two acceptors differ include positions H19 (R or K), H40 (A or T), H44 (G or R), H49 (S or A), H77 (S or T), H82a (N or S), H83 (R or K), H84 (A or S), and H89 (V or M) by Kabat numbering. The rationales for choosing one amino acid or the other at these positions are as follows.

H19 (R or K): R and K are present in the two frameworks considered, so each residue was tried in separate versions.

H40 (A or T): A and T are present in the two frameworks considered, so each residue was tried in separate versions.

H44 (G or R): G and R are present in the two frameworks considered, so each residue was tried in separate versions.

H49 (S or A): This is a vernier residue that packs under CDR-H2. In the murine sequence, it is A. The slight size difference and hydrophilic nature of S could potentially perturb the CDR foundation. S and A were included in separate versions.

H77 (S or T): S and T are present in the two human acceptor frameworks considered, so each was tried in separate versions.

H82a (N or S): N at this position is much less frequent than S. Moreover, S appears to be contributing to antigen binding. Mutation to S was tried in some versions.

H83 (R or K): K in framework region 3 is close to the CDR binding surface area. Replacing it with R, which is builder than K, might obstruct placement of antigen. R is most frequent and K is third frequent in human frameworks at this position. R and K were included in separate versions.

H84 (A or S): S and A are present in the two frameworks considered, so each residue was tried in separate versions.

H89 (V or M): V and M are present in the two frameworks considered, so each was tried in separate versions.

The five humanized light chain variable region variants and five humanized heavy chain variable region variants are as follows:

Hu9D5VL version 1 (Y36F substitution in lowercase):

```
                                        (SEQ ID NO: 19)
DIVMTQSPLSLPVTPGEPASISCRSSKSLLHSNGNTYLYWfLQKPGQSPQL

LIYRVSNLASGVPDRFSGSGSGTDFTLKISRVEAEDVGVYYCMQHLEYPLT

FGQGTKLEIK

Hu9D5VL version 2 (no substitutions):
                                        (SEQ ID NO: 20)
DIVMTQSPLSLPVTPGEPASISCRSSKSLLHSNGNTYLYWLQKPGQSPQL

LIYRVSNLASGVPDRFSGSGSGTDFTLKISRVEAEDVGVYYCMQHLEYPLT

FGQGTKLEIK

Hu9D5VL version 3 (D60S substitution in lowercase):
                                        (SEQ ID NO: 21)
DIVMTQSPLSLPVTPGEPASISCRSSKSLLHSNGNTYLYWLQKPGQSPQL LIYRVSNLASGVPsRFSGSGSGTDFTLKISRVEAEDVGVYYCMQHLEYPLT

FGQGTKLEIK

Hu9D5VL version 4 (P8A, L9P, A19V, Y36F, K39R,
D60S, D70A, and K74R substitutions in lowercase):
                                        (SEQ ID NO: 22)
DIVMTQSapSLPVTPGEPvSISCRSSKSLLHSNGNTYLYWfLQrPGQSPQL LIYRVSNLASGVPsRFSGSGSGTaFTLrISRVEAEDVGVYYCMQHLEYPLT

FGQGTKLEIK

Hu9D5VL version 5 (P8A, L9P, P18S, A19V, Y36F,
K39R, D60S, D70A, and K74R substitutions in
lowercase):
                                        (SEQ ID NO: 23)
DIVMTQSapSLPVTPGEsvSISCRSSKSLLHSNGNTYLYWfLQrPGQSPQL LIYRVSNLASGVPsRFSGSGSGTaFTLrISRVEAEDVGVYYCMQHLEYPLT

FGQGTKLEIK
```

-continued

Hu9D5VH version 1 (W47L, I69F, and M82S substitutions in lowercase):

(SEQ ID NO: 5)
EVQLVESGGGLVQPGGSLRLSCAASGFTFSSYTMSWVRQAPGKGLElVAEI

SNSGDTTYYPDTVKGRFTfSRDNAKNSLYLQsNSLKAEDTAVYYCARHYYY

GGGYGGWFFDVWGQGTTVTVSS

Hu9D5VH version 2 (W47L, I69F, M82S, and S82(b)L substitutions in lowercase):

(SEQ ID NO: 6)
EVQLVESGGGLVQPGGSLRLSCAASGFTFSSYTMSWVRQAPGKGLElVAEI

SNSGDTTYYPDTVKGRFTfSRDNAKNSLYLQsNlLRAEDTAVYYCARHYYY

GGGYGGWFFDVWGQGTTVTVSS

Hu9D5VH version 2b (G42E, W47L, and T108L substitutions in lowercase):

(SEQ ID NO: 7)
EVQLVESGGGLVQPGGSLKLSCAASGFTFSSYTMSWVRQTPeKRLElVAEI

SNSGDTTYYPDTVKGRFTISRDNAKNTLYLQMSSLKSEDTAMYYCARHYYY

GGGYGGWFFDVWGQGTlVTVSS

Hu9D5VH version 3 (I69F, M82S, and S82(b)L substitutions in lowercase):

(SEQ ID NO: 8)
EVQLVESGGGLVQPGGSLRLSCAASGFTFSSYTMSWVRQAPGKGLEWVSEI

SNSGDTTYYPDTVKGRFTfSRDNAKNSLYLQsNlLRAEDTAVYYCARHYYY

GGGYGGWFFDVWGQGTTVTVSS

Hu9D5VH version 3b (W47L and T108L substitutions in lowercase):

(SEQ ID NO: 9)
EVQLVESGGGLVQPGGSLKLSCAASGFTFSSYTMSWVRQTPGKRLElVAEI

SNSGDTTYYPDTVKGRFTISRDNAKNTLYLQMSSLKSEDTAMYYCARHYYY

GGGYGGWFFDVWGQGTlVTVSS

Hu9D5VH version 4 (M82S and S82(b)L substitutions in lowercase):

(SEQ ID NO: 10)
EVQLVESGGGLVQPGGSLRLSCAASGFTFSSYTMSWVRQAPGKGLEWVSEI

SNSGDTTYYPDTVKGRFTISRDNAKNSLYLQsNlLRAEDTAVYYCARHYYY

GGGYGGWFFDVWGQGTTVTVSS

Hu9D5VH version 4b (W47L and T108L substitutions in lowercase):

(SEQ ID NO: 11)
EVQLVESGGGLVQPGGSLKLSCAASGFTFSSYTMSWVRQAPGKRLElVAEI

SNSGDTTYYPDTVKGRFTISRDNAKNTLYLQMSSLKSEDTAMYYCARHYYY

GGGYGGWFFDVWGQGTlVTVSS

Hu9D5VH version 5 (G42E, W47L, and S82(b)L substitutions in lowercase):

(SEQ ID NO: 12)
EVQLVESGGGLVQPGGSLRLSCAASGFTFSSYTMSWVRQTPeKRLElVAEI

SNSGDTTYYPDTVKGRFTISRDNAKNTLYLQMNlLRAEDTAVYYCARHYYY

GGGYGGWFFDVWGQGTTVTVSS

Protein quality analysis along with aggregation potential analyses showed no obvious clusters of aggregation-prone residues present in the 9D5 light chain or heavy chain framework regions or CDRs (Wang et al., mAbs 1(3):254-267, 2009).

Example 8. Binding Kinetic Analysis of Humanized 9D5 Antibodies

Binding kinetics of binding of all humanized 9D5 variants, murine 9D5, and chimeric 9D5 to recombinant human TTR F87M/L110M were characterized by Biacore, as shown in Table 10. Anti-human (GE Healthcare) was immobilized on sensor chip C5 (lacking dextran chains) via amine coupling following the instructions provided in the GE Healthcare anti-human kit, and mAbs were captured to a level to ensure a maximum binding of analyte of 30-50 RU. Various concentrations of analyte (recombinant human TTR F87M/L110M) were passed over the captured ligand at 50 ul/min in running buffer (HBS+0.05% P-20, 1 mg/mL BSA) in 3-fold dilutions. For each concentration, the reaction proceeded for a time frame allowing for the higher analyte concentrations to reach equilibrium during association, as well as at least 10% of signal to decay during dissociation. At least one concentration (not the highest or lowest) was run in duplicate. Concentration ranges of analyte were selected based on preliminary experimentation to span at least 10-fold above $K_D$ to 10-fold below $K_D$.

Table 10 summarizes the Biacore association rate ($k_a$), dissociation rate ($k_d$), and binding affinity constant ($K_D$) of the murine, chimeric, and humanized 9D5 variants for recombinant human TTR F87M/L110M.

TABLE 10

| Antigen Binding Affinity of 9D5 Antibodies to Human TTR (F87M/L110M) | | | | |
| --- | --- | --- | --- | --- |
| Antibody | $k_a$ (1/Ms) | $k_d$ (1/s) | $K_D$ (M) | Rmax |
| Murine 9D5 | 2.72E+04 | 4.93E−04 | 1.82E−08 | 31.55 |
| Chimeric 9D5 | 2.59E+05 | 3.50E−04 | 1.35E−09 | 47.05 |
| Hu9D5 H2L5 | 1.15E+05 | 7.85E−04 | 6.84E−09 | 57.6 |
| Hu9D5 H3L1 | 1.52E+04 | 6.57E−04 | 4.32E−09 | 54.93 |
| Hu9D5 H4L1 | 2.54E+05 | 5.33E−04 | 2.09E−09 | 43.91 |

These results indicate that the affinity of murine 9D5 for TTR-F87M/L110M ($K_D$=1.82E-08M) has been slightly improved in the chimeric 9D5 variant ($K_D$=1.35E-09M). Furthermore, the fully humanized 9D5 variants all have similar affinities in the low nM range. Hu9D5 H4L1 has the strongest affinity ($K_D$=2.09E-09) of the humanized 9D5 variants tested.

Example 9. Design of Humanized 14G8 Antibodies

The starting point or donor antibody for humanization was the mouse antibody 14G8. The heavy chain variable amino acid sequence of mature m14G8 is provided as SEQ ID NO: 61. The light chain variable amino acid sequence of mature m14G8 is provided as SEQ ID NO: 70. The heavy chain CDR1, CDR2, and CDR3 amino acid sequences are provided as SEQ ID NOS: 67-69, respectively (as defined by Kabat). A composite Chothia-Kabat CDR-H1 is provided as SEQ ID NO: 118. The light chain CDR1, CDR2, and CDR3 amino acid sequences are provided as SEQ ID NOS: 77-79, respectively (as defined by Kabat). A variant version of CDR1 is provided as SEQ ID NO: 80. Kabat numbering is used throughout in this Example.

The variable kappa (Vk) of m14G8 belongs to mouse Kabat subgroup 2, which corresponds to human Kabat subgroup 2. The variable heavy (Vh) of m14G8 belongs to mouse Kabat subgroup 3d, which corresponds to Kabat subgroup 1. See Kabat et al. Sequences of Proteins of Immunological Interest, Fifth Edition. NIH Publication No. 91-3242, 1991. The 16-residue CDR-L1 belongs to canonical class 3, the 7-residue CDR-L2 belongs to canonical class 1, and the 9-residue CDR-L3 belongs to canonical class 1 in Vk. See Martin & Thornton, J. Mol. Biol. 263:800-15, 1996. The 10-residue composite Chothia-Kabat CDR-H1 belongs to canonical class 1, and the 17-residue CDR-H2 belongs to canonical class 1. See Martin & Thornton, J Mol. Biol. 263:800-15, 1996. The CDR-H3 has no canonical classes, but the 15-residue loop probably has a kinked base according to the rules of Shirai et al., FEBS Lett. 455:188-97 (1999).

The residues at the interface between the Vk and Vh domains are the ones commonly found except L47, at which position the principle amino acid is usually W.

A search was made over the protein sequences in the PDB database (Deshpande et al., Nucleic Acids Res. 33: D233-7, 2005) to find structures which would provide a rough structural model of 14G8. The crystal structure of Fab with esterase activity (pdb 1MJU) was used as the model for the Vk structure. It was solved at a resolution of 1.22 A and contains the same canonical structures for CDR-H1 and CDR-H2, and also contains the same length CDR-H3 with a kinked based. An anti-cytochrome C oxidase antibody 7E2 Fv fragment (pdb code 1MQK_H) was used for the Vh structure. It has a resolution of 1.28 A and retains the same canonical structure for the loops as 14G8. BioLuminate software (licensed from Schrodinger Inc.) was used to model a rough structure of 14G8.

A search of the non-redundant protein sequence database from NCBI allowed selection of suitable human frameworks into which to graft the murine CDRs. For Vh, human Ig heavy chains with NCBI accession codes AAD30410.1 and AAX82494.1 were chosen. These share the canonical forms of 14G8 CDR-H1 and H2, and H3 of AAD30410.1 is 15 residues long with a predicted kinked base. For Vk, two human kappa light chains with NCBI accession codes ABA71374.1 and ABC66952.1 were chosen. They have the same canonical classes for LCDRs.

Three humanized heavy chain variable region variants and three humanized light chain variable region variants were constructed containing different permutations of substitutions (Hu14G8VHv1-3 (SEQ ID NOS: 64-66, respectively) and Hu14G8VLv1-3 (SEQ ID NOS: 74-76, respectively)) (FIGS. 14A-E and FIGS. 15A-D). The exemplary humanized Vh and Vk designs, with backmutations and other mutations based on selected human frameworks, are shown in FIGS. 14A-E and FIGS. 15A-D, respectively. The gray-shaded areas in the first column in FIGS. 14A-E and FIGS. 15A-D indicate the CDRs as defined by Chothia, and the gray-shaded areas in the remaining columns in FIGS. 14A-E and FIGS. 15A-D indicate the CDRs as defined by Kabat. SEQ ID NOS: 64-66 and 74-76 contain backmutations and other mutations as shown in Table 11. The amino acids at positions H1, H3, H47, H105, L8, L9, L19, L26, L36, L60, and L70 in Hu14G8VHv1-3 and Hu14G8VLv1-3 are listed in Tables 12 and 13.

TABLE 11

$V_H$, $V_L$ Backmutations and Other Mutations

| $V_H$ or $V_L$ Variant | $V_H$ or $V_L$ Exon Acceptor Sequence | Donor Framework Residues | Kabat CDR Residues |
| --- | --- | --- | --- |
| Hu14G8VHv1 (SEQ ID NO: 64) | NCBI accession codes AAD30410.1 and AAX82494.1 (SEQ ID NOS: 63 and 4, respectively) | H1, H3, H47, H105 | — |
| Hu14G8VHv2 (SEQ ID NO: 65) | NCBI accession codes AAD30410.1 and AAX82494.1 (SEQ ID NOS: 63 and 4, respectively) | H1, H47 | — |
| Hu14G8VHv3 (SEQ ID NO: 66) | NCBI accession codes AAD30410.1 and AAX82494.1 (SEQ ID NOS: 63 and 4, respectively) | H1, H47 | — |
| Hu14G8VLv1 (SEQ ID NO: 74) | NCBI accession codes ABA71374.1 and ABC66952.1 (SEQ ID NOS: 72 and 73, respectively) | L8, L9, L19, L36, L70 | — |
| Hu14G8VLv2 (SEQ ID NO: 75) | NCBI accession codes ABA71374.1 and ABC66952.1 (SEQ ID NOS: 72 and 73, respectively) | L36 | — |
| Hu14G8VLv3 (SEQ ID NO: 76) | NCBI accession codes ABA71374.1 and ABC66952.1 (SEQ ID NOS: 72 and 73, respectively) | L36, L60 | L26 |

TABLE 12

Kabat Numbering of Framework and Kabat CDR Residues for Backmutations and Other Mutations in Humanized 14G8 Antibody VH Regions

| Residue | AAD30410.1 Heavy Chain | AAX82494.1 Heavy Chain | Mouse 14G8 | Hu14G8 VHv1 | Hu14G8 VHv2 | Hu14G8 VHv3 |
| --- | --- | --- | --- | --- | --- | --- |
| H1 | Q | Q | E | E | E | E |
| H3 | Q | Q | K | K | Q | Q |
| H47 | W | W | L | L | L | L |
| H105 | Q | Q | T | T | Q | Q |

TABLE 13

Kabat Numbering of Framework and Kabat CDR Residues for Backmutations and Other Mutations in Humanized 14G8 Antibody VL Regions

| Residue | ABA71374.1 Light Chain | ABC66952.1 Light Chain | Mouse 14G8 | Hu14G8 VLv1 | Hu14G8 VLv2 | Hu14G8 VLv3 |
|---|---|---|---|---|---|---|
| L8  | P | P | A | A | P | P |
| L9  | L | L | P | P | L | L |
| L19 | A | A | V | V | A | A |
| L26 | S | N | N | N | N | S |
| L36 | Y | Y | F | F | F | F |
| L60 | D | D | D | D | D | S |
| L70 | D | D | A | A | D | D |

An alignment of the murine 14G8 Vh sequence (SEQ ID NO: 61) with the mouse model sequence (1MQK_H; SEQ ID NO: 62), the human acceptor sequences (AAD30410.1 and AAX82494.1; SEQ ID NOS: 63 and 4, respectively), and the Hu14G8VHv1, Hu14G8VHv2, and Hu14G8VHv3 sequences (SEQ ID NOS: 64-66, respectively), is shown in FIG. 2A. The CDRs as defined by Kabat are enclosed in boxes, except that the first enclosed box is a composite of the Chothia CDR-H1 and the Kabat CDR-H1, with the Kabat CDR-H1 underlined and bolded. Positions at which canonical, vernier, or interface residues differ between mouse and human acceptor sequences are candidates for substitution. Examples of vernier/CDR foundation residues include residues 2, 49, 69, 71, 75, 80, and 94 by Kabat numbering in FIGS. 14A-E. Examples of canonical/CDR interacting residues include residues 24, 48, and 73 by Kabat numbering in FIGS. 14A-E. Examples of interface/packing (VH+VL) residues include residues 37, 39, 44, 47, 91, 93, and 103 by Kabat numbering in FIGS. 14A-E.

An alignment of the murine 9D5 Vk 14G8 (SEQ ID NO: 70) with the mouse model sequence (1MJU_L; SEQ ID NO: 71), the human acceptor sequences (ABA71374.1 and ABC66952.1; SEQ ID NOS: 72 and 73, respectively), and the Hu14G8VLv1, Hu14G8VLv2, Hu14G8VLv3 sequences (SEQ ID NOS: 74-76, respectively), is shown in FIG. 2B. The CDRs as defined by Kabat are enclosed in boxes, except that the first enclosed box is a composite of the Chothia CDR-H1 and the Kabat CDR-H1, with the Kabat CDR-H1 underlined and bolded. Positions at which canonical, vernier, or interface residues differ between mouse and human acceptor sequences are candidates for substitution. Examples of vernier/CDR foundation residues include residues 4, 35, 46, 49, 66, 68, and 69 by Kabat numbering in FIGS. 15A-D. Examples of canonical/CDR interacting residues include residues 2, 48, 64, and 71 by Kabat numbering in FIGS. 15A-D. Examples of interface/packing (VH+VL) residues include residues 36, 38, 44, 47, 87, and 98 by Kabat numbering in FIGS. 15A-D.

The rationales for selection of the positions indicated in Tables 11 and 13 in the light chain variable region as candidates for substitution are as follows.

P8A: Proline is critical to structure conformation, and loss or gain of proline may affect the structure. Backmutations were designed to avoid "gain of proline." However, since A at this position is rare in human IgG frameworks, P was included in some versions.

L9P: Proline is critical to structure conformation, and loss or gain of proline may affect the structure. Backmutations were designed to avoid "loss of proline." However, since P at this position is rare in human IgG frameworks, L was included in some versions.

A19V: A and V have similar frequencies in human frameworks. Both residues were included in separate versions.

N26S: L26 represents an N-glycosylation site in light chain CDR1. Mutation to S reduces N-glycosylation and yields a more heterogeneous product.

Y36F: This is an interface residue. Substitution was made in some versions to keep the murine residue at this interface residue.

D60S: D and S are similar in frequency in human IgG frameworks. S is applied by most commercially available therapeutic antibodies, so D was replaced with S in some versions.

D70A: D is much more frequent than A in human IgG frameworks. However, D will form ionic bond with R24 in light chain CDR1, so both A and D were included in separate versions.

The rationales for selection of the positions indicated in Tables 11 and 12 in the heavy chain variable region as candidates for substitution are as follows.

Q1E: Glutamate (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

Q3K: Q is more frequent in human IgG frameworks. K is less frequent but not rare. Both residues were included in separate versions.

W47L: This is an interface residue. Substitution was made in some versions to keep the murine residue at this interface residue.

Q105T: T may form a hydrogen bond with K3, so T was included in some versions to maintain the conformational structure of VH.

Because two human acceptor frameworks (ABA71374.1 and ABC66952.1 (SEQ ID NOS: 72 and 73, respectively)) were used for humanization of the 14G8 light chain variable region, there are certain framework positions that have different amino acids in the two acceptor frameworks. Humanized versions of the 14G8 light chain variable region can include either amino acid at these residues. An example of a residue in which these two acceptors differ is position L18 (S or P) by Kabat numbering. The rationale for choosing one amino acid or the other at this position is as follows.

L18 (S or P): P at this position is less frequent. Mutation to S was tried to alleviate loop distortion.

Because two human acceptor frameworks (AAD30410.1 and AAX82494.1 (SEQ ID NOS: 63 and 4, respectively)) were also used as acceptor sequences for humanization of the 14G8 mature heavy chain variable region, there are certain framework positions that have different amino acids in the two acceptor frameworks. Humanized versions of the 14G8 heavy chain variable region can include either amino acid at these residues. Examples of residues in which these two acceptors differ include positions H82a (N or S), H83 (R or K), H84 (A or S), and H89 (V or M) by Kabat numbering. The rationales for choosing one amino acid or the other at these positions are as follows.

H82a (N or S): N and S have similar frequency on 82a. They are also human residues in two human VH templates. S and N were included in separate versions.

H83 (R or K): K in framework region 3 is close to the CDR binding surface area. Replacing it with R might obstruct placement of antigen. R is most frequent and K is third frequent in human frameworks at this position. R and K were included in separate versions.

H84 (A or S): S and A are present in the two frameworks considered, so each residue was tried in separate versions.

H89 (V or M): V and M are present in the two frameworks considered, so each was tried in separate versions.

The three humanized light chain variable region variants and three humanized heavy chain variable region variants are as follows:

Hu14G8VL version 1 (P8A, L9P, A19V, Y36F, D70A substitutions in lowercase):

```
                                            (SEQ ID NO: 74)
DIVMTQSapSLPVTPGESvSISCRSNKSLLHSNGNTYLYWfLQKPGQSPQ

LLIYRVSNLASGVPDRFSGSGSGTaFTLKISRVEAEDVGVYYCMQHLEYP

LTFGQGTKLEIKR
```

Hu14G8VL version 2 (L36F substitution in lowercase):
```
                                            (SEQ ID NO: 75)
DIVMTQSPLSLPVTPGEPASISCRSNKSLLHSNGNTYLYWfLQKPGQSPQ

LLIYRVSNLASGVPDRFSGSGSGTDFTLKISRVEAEDVGVYYCMQHLEYP

LTFGQGTKLEIKR
```

Hu14G8VL version 3 (N26S, L36F, and D60S substitutions in lowercase):
```
                                            (SEQ ID NO: 76)
DIVMTQSPLSLPVTPGEPASISCRSsKSLLHSNGNTYLYWfLQKPGQSPQ LLIYRVSNLASGVPsRFSGSGSGTDFTLKISRVEAEDVGVYYCMQHLEYP

LTFGQGTKLEIKR
```

Hu14G8VH version 1 (Q1E, Q3K, W47L, and Q105T substitutions in lowercase):
```
                                            (SEQ ID NO: 64)
eVkLVE5GGGLVQPGGSLKLSCAASGFTFSSYTMSWVRQTPEKRLElVAE

INNSGDTTYYPDTVKGRFTISRDNAKNTLYLQMSSLKSEDTAMYYCARHY

YYGGGYGGWFFDVWGtGTLVTVSS
```

Hu14G8VH version 2 (Q1E and W47L substitutions in lowercase):
```
                                            (SEQ ID NO: 65)
eVQLVESGGGLVQPGGSLKLSCAASGFTFSSYTMSWVRQTPEKRLElVAE

INNSGDTTYYPDTVKGRFTISRDNAKNTLYLQMSSLKSEDTAMYYCARHY

YYGGGYGGWFFDVWGQGTLVTVSS
```

Hu14G8VH version 3 (Q1E and W47L substitutions in lowercase):
```
                                            (SEQ ID NO: 66)
eVQLVESGGGLVQPGGSLKLSCAASGFTFSSYTMSWVRQTPEKRLElVAE

INNSGDTTYYPDTVKGRFTISRDNAKNTLYLQMNSLRAEDTAVYYCARHY

YYGGGYGGWFFDVWGQGTLVTVSS
```

Example 10. Binding Kinetic Analysis of Humanized 14G8 Antibodies

Binding kinetics of three humanized 14G8 variants and murine 14G8 to recombinant human TTR F87M/L110M were characterized by Biacore, as shown in Table 14. Anti-human (GE Healthcare) was immobilized on sensor chip C5 (lacking dextran chains) via amine coupling following the instructions provided in the GE Healthcare anti-human kit, and mAbs were captured to a level to ensure a maximum binding of analyte of 30-50 RU. Various concentrations of analyte (recombinant human TTR F87M/L110M) were passed over the captured ligand at 50 ul/min in running buffer (HBS+0.05% P-20, 1 mg/mL BSA) in 3-fold dilutions. For each concentration, the reaction proceeded for a time frame allowing for the higher analyte concentrations to reach equilibrium during association, as well as at least 10% of signal to decay during dissociation. At least one concentration (not the highest or lowest) was run in duplicate. Concentration ranges of analyte were selected based on preliminary experimentation to span at least 10-fold above $K_D$ to 10-fold below $K_D$.

Table 14 summarizes the association rate ($k_a$), dissociation rate ($k_d$), and binding affinity constant ($K_D$) of the mouse 14G8, chimeric-14G8, Hu14G8 H2L1, Hu14G8 H2L2, Hu14G8H2L3, and Hu14G8 H3L1 for recombinant human TTR F87M/L110M, As shown in Table 14, Hu14G8 antibodies and mouse 14G8 have similar TTR binding affinities.

TABLE 14

| Antigen Binding Affinity of 14G8 Antibodies to Human TTR (F87M/L110M) | | | | |
|---|---|---|---|---|
| Antibody | $k_a$ (1/Ms) | $k_d$ (1/s) | $K_D$ (M) | Rmax |
| Murine 14G8 | 2.88E+04 | 5.36E−04 | 1.86E−08 | 27.13 |
| Chimeric 14G8 | 2.51E+05 | 3.46E−04 | 1.38E−09 | 51.06 |
| Hu14G8 H2L1 | 3.07E+05 | 6.93E−04 | 2.26E−09 | 42.03 |
| Hu14G8 H2L2 | 3.26E+05 | 6.83E−04 | 2.10E−09 | 51.43 |
| Hu14G8 H2L3 | 2.52E+05 | 3.18E−04 | 1.24E−09 | 42.41 |
| Hu14G8 H3L1 | 3.86E+05 | 6.77E−04 | 1.76E−09 | 44.05 |

Murine 14G8, chimeric 14G8, and other humanized version of 14G8 with no changes in LCDR1 showed additional light chains when run on SDS-PAGE under reducing conditions. Sequence analysis revealed that there is an N-glycosylation site in LCDR1 at residue 26 by Kabat numbering. This N-glycosylation site may cause potential heterogenecity problems during manufacture. Mutation of the N at residue L26 in Hu14G8VLv2 yielded Hu14G8VLv3. Humanized antibodies having Hu14G8VLv3 show only one light chain when run on SDS-PAGE under reducing conditions, thereby eliminating the potential heterogenecity problem. The antigen binding affinity of Hu14G8 H2L3 is similar to that of the murine parent antibody and the chimeric antibody.

Example 11. Materials and Methods a. Antibody Generation Protocol

Mice were immunized weekly with the antigenic peptides TTR-MAP, TTR89-97-N-KLH or TTR89-97-C-KLH in RIBI adjuvant or monthly in TiterMax adjuvant. Three to four days prior to fusion, selected mice were given a final IV boost with immunogen in saline solution. Spleen were homogenized to prepare splenocytes and fused with SP2/0 myeloma cells using a standard electrofusion protocol.

Fused cells in selection media were plated in 96-well plates and screened after 7-10 days.

b. Antibody Screening Protocol

Hybridoma selection was based on the following ELISA screen: 96-well ELISA plates were coated with chicken anti-His, 1 μg/mL PBS and incubated for 1 hour. Plates were blocked with of 1% BSA/PBS solution, 200 uL/well for 15 minutes then 0.5 μg/mL pH4-TTR, 50 μL/well was added and incubated for 1 hour. pH4-TTR is TTR that has been subjected to low pH (50 mM sodium acetate, pH 4.0) in order to dissociate/aggregate TTR, exposing the TTR89-97 epitope. Plates were washed twice with TBS-T. Supernatant from fusion plates was added, 50 μL/well and incubated for 1 hour. Plates were washed twice with TBS-T. The detection antibody, goat anti-mouse (IgG1, 2a, 2b, 3 specific)-HRP diluted 1:5,000 in 0.5% BSA/PBS/TBS-T, 50 μL/well was added and incubated for 1 hour. Finally, plates were washed five times with TBS-T and TMB substrate, 100 μL/well was added. After 15 minutes, substrate development was stopped with 2N Sulfuric Acid, 50 μL/well. Plates were read at 450 nm. Wells with an O.D.>1.0 were selected and cells were transferred to a 24-well plate. After 3 days of growth, clones were counter screened with the above assay to confirm binding, and substituting native TTR for pH4-TTR as a negative counter screen, allowing for selection of clones producing TTR mAbs specific for non-native forms of TTR.

c. Antibody Expression Protocols

CMV driven light chain and heavy chain plasmids carrying humanized monoclonal antibody sequences were transfected into CHO-S1 cells (Life Technology). Dual selection was applied to make a selected pool. Conditioned media was assayed for titer, binding and analyzed by SDS-PAGE/Western blotting. Selected pools were used for clone generation using Clonepix system (Molecular Devices). Clones were ranked based on antibody titer. Selected clones were expanded and banked.

The highest producing clone was expanded in shake flasks and the culture was used to inoculate 10-25L Wave bag cultures. A mixture of FreeStyle-CHO, CD OptiCHO and FreeStyle F17 expression media supplemented with Glutamax (media and Glutamax from Life Technology) was used for shake flask as well as for Wave bag cultures. Batch culture was made using a Wave Bioreactor (GE Healthcare) at 37° C., 7% $CO_2$ under constant agitation. Samples were drawn periodically to monitor cell number, viability and antibody production. Supplementation with Cell Boost (Hy-Clone) was made if needed. The batch culture was harvested when cell viability starts to decline below 90% (5-7 days).

d. Antibody Purification Protocol

The cell culture was harvested after first allowing the cells in suspension to settle down to the bottom of the Wave bag via gravity at 4° C. Harvested media was clarified through a depth filter (Millistak Pod COHC, Millipore), concentrated 10-fold by tangential flow filtration (Pelicon 2PLC 30K, Millipore) and sterile filtered through a 0.2 μm filter (Opticap XL, Millipore). The concentrated conditioned media was then loaded onto a Protein G Sepharose Fast Flow column (GE Lifesciences) pre-equilibrated in 1×PBS, pH 7.4 using an FPLC (Akta Avant, GE Lifesciences). Unbound proteins were washed off the column with 5-10 column volumes of 1×PBS, pH 7.4 until the OD280 reached baseline. The bound antibody was eluted from the column with 2 column volumes of IgG Elution Buffer (Thermo Scientific). Elution fractions were collected and pH neutralized with 2M Tris, pH 9.0 (60 μL per 1 ml elution).

Antibody-containing fractions were pooled and dialyzed overnight at 4° C. against 1×PBS, pH 7.4. The dialyzed sample was then sterilized by ultrafiltration through a 0.2 μm PES filter and stored at 4° C. The final protein concentration was determined by bicinchoninic acid (BCA) using bovine gamma-globulin as the protein standard (Thermo Scientific).

e. Recombinant TTR Expression and Purification Protocols

*E. coli* (BL21-A1) cells were transformed with a pET21a (+) plasmid containing a TTR insert (Met-hTTR-(His)$_6$ or a TTR variant containing an F87M/L110M double mutation. Cells were grown in 2YT broth containing 100 μg/ml ampicillin. Expression of TTR was induced overnight at 20° C. in the presence of 1 mM IPTG and 005% arabinose.

The cells were collected by centrifugation at 4000×g for 10 min. and stored at −80° C. until used. 10-15 g cell pellets were thawed and lysed in 50 ml Buffer A (1×PBS containing 500 mM NaCl, 20 mM imidazole) by processing through an LV-1 high-shear processor (Microfluidics, Inc.). Lysed cells were centrifuged at 12,000×g for 15 min, filtered through a 0.2 μm PES filter prior to purification on a His-Trap HP column (GE Lifesciences). After loading, the column was washed with 10 c.v. of Buffer A and eluted with Buffer B (1×PBS with 500 mM NaCl, 500 mM imidazole). Peak fractions corresponding to TTR were collected, dialyzed against 1×PBS and stored at −80° C. until used.

f. TTR Antigen Preparation

Native TTR antigen was prepared by diluting a concentrated stock of recombinant TTR-6His to a final concentration of 2.5 μg/ml in 1×PBS. pH4-treated TTR was generated by incubating recombinant TTR at a concentration of 0.2 mg/ml in 50 mM sodium acetate, pH 3.95 for 72 hours at room temperature. Under these conditions, TTR dissociates into mixture of TTR monomers and aggregated forms that are structurally distinct from native TTR. The pH4-TTR was then diluted to a final concentration of 2.5 μg/ml in 1×PBS immediately before use in the assay. 96-well plates (Costar #3690) were coated at room temperature with 50 μl per well of 1.0 μg/ml chicken-anti-his polyclonal antibody (Abcam #Ab9107) in 1×PBS for 1 hr. The coating solution was discarded and the plate was blocked with a 250 μl per well volume of 1×BSA-containing block buffer diluted in 1×PBS (G-Biosciences #786-193) for 1 hr.

g. ELISA Protocol

Coated and blocked 96-well plates were treated with 50 μl per well of 2.5 μg/ml TTR antigen (either native TTR or pH4-TTR) for 1 hr. at room temperature. The plates were then washed two times with 250 μl per well of wash buffer (1× Tris Buffered Saline containing 0.05% Tween-20). Washed plates were then treated with 50 μl per well of the appropriate anti-TTR monoclonal antibody at concentrations ranging from of 0.31 to 2.5 μg/ml, for 1 hr.

The treated plates were washed 3 times with 250 μl per well wash buffer. After washing, the plates were treated for 1 hr. with 50 μl per well of detection antibody comprising a 1:5,000 dilution of peroxide-conjugated goat-anti-mouse (Jackson ImmunoResearch #115-035-164) in 1×PBS. The plate was then washed 3 times prior to the addition of 100 μl per well TMB substrate (Rockland). The HRP reaction was allowed to proceed at room temperature for 15 min. before quenching with a 50 μl per well volume of 1N $H_2SO_4$. Spectroscopic absorbance was measured at a wavelength of 450 nm.

h. SDS-PAGE

Electrophoresis on SDS-polyacrylamide gels was carried out as follows. 0.1-1 μg TTR or pH 4.0-TTR in 1×LDS sample buffer (Life Technologies) was loaded onto a 10% NuPAGE bis-tris gel and subjected to electrophoresis in MES buffer at a constant 90V for 105 minutes. After electrophoresis, the gel was either stained in Instant Blue (Expedeon) or transferred to nitrocellulose filters for Western blot analysis.

i. Native-PAGE

Electrophoresis on native Tris-glycine gels was carried out as follows. 0.1-1 µg TTR or pH 4.0-TTR in 1× Tris-glycine sample buffer (Life Technologies) was loaded onto a 10-20% Tris-glycine gel and subjected to electrophoresis in 1× Native Tris-glycine running buffer at a constant 120V for 105 minutes. After electrophoresis, the gel was either stained in Instant Blue (Expedeon) or transferred to nitrocellulose filters for Western blot analysis.

j. Western Blot

SDS- or Native-PAGE gels were blotted onto nitrocellulose filter paper (iBlot, P7 Program) and blocked with blocking buffer (Licor) for 30 minutes. The filters were then incubated in 0.5 µg/ml primary antibody in blocking buffer for 1 hour at room temperature (or over-night at 4° C.), followed by three, 10 minutes washes with 1×TBS. The filters were placed in IRDye 800CW-conjugated goat-anti-mouse secondary diluted 1:20,000 in block buffer. After incubating the filters in secondary antibody solution for 1 hour at room temperature, the filters were washed and imaged on an Odyssey CLx infrared imager (Licor).

k. TTR Fiber Formation Assay Protocol

A solution of 3.6 µM (0.2 mg/ml) TTR-Y78F in 50 mM sodium acetate, pH 4.8 was incubated at 37° C. for 72 hours in the presence of 1.4 µM (0.2 mg/ml) mis-TTR antibody or an isotype control. After incubation, a 5× molar excess of thioflavin-T was added to the mixture and allowed to bind for 30 minutes. Fluorometric measurements were measured at an emissions wavelength of 480 nm with an excitation wavelength set at 440 nm. The 0% inhibition was set as the fluorescence intensity in the presence of an isotype control antibody (83 a.u.) and the 100% inhibition point was set as the fluorescence in the absence of TTR-Y78F protein (38 a.u.).

A stock solution of TTR-V122I (approximately 5 mg/mL) was diluted into buffer with final concentrations of 0.2 mg/mL TTR, 30 mM sodium acetate, 5 mM sodium phosphate, 100 mM KCl, 1 mM EDTA, 0.02% sodium azide, and varying concentrations of monoclonal antibody at pH 7.2. This sample was dialyzed against the same buffer at pH 4.5 for 3 h at room temperature. Samples were then incubated at 37° C. for 72 hours. After incubation a 5× molar excess of thioflavin-T was added to was added to the mixture and allowed to bind for 30 minutes. Thioflavin-T fluorescence was monitored using a Photon Technology International C60 spectrofluorimeter. The photomultiplier gain was varied and excitation and emission slit widths set to 2-4 nm to maximize signal to noise. Fluorescence measurements were made using 430 nm and 480 nm as excitation and emission wavelengths, respectively.

l. Cardiac Tissue Samples

Fresh frozen and paraffin-processed blocks of cardiac tissue with confirmed diagnoses of ATTR mutations were obtained from Dr. Merrill Benson at Indiana University. Samples included eight fresh frozen samples and six FFPE samples and each sample was diagnosed with either ATTR or some other cardiac amyloidosis. The diagnosis of the tissue was further confirmed at Prothena via IHC staining with antibodies to kappa and lambda light chains and amyloid A prior to characterization with the TTR antibodies.

m. Immunohistochemistry

Immunohistochemistry was performed on lightly paraformaldehyde-fixed, 10 µm slide-mounted cryo sections and on 5 µm paraffin sections. The immunoperoxidase method was the principal detection system, which was performed on the Leica Bond Rx (Leica Biosystems, Buffalo Grove, Ill.) using the Bond Polymer Refine Detection Kit (DS980, Leica Biosystems). The primary antibodies were incubated for one hour (according to concentrations in Table 2) followed by incubation with anti-mouse and anti-rabbit polymeric HRP-linker antibody conjugates. The staining was visualized with a DAB chromogen, which produced a brown deposit. The slides were counterstained with hematoxylin, dehydrated in an ascending series of alcohols, cleared in xylenes, and coverslipped with CytoSeal 60 (Richard Allen Scientific; Kalamazoo, Mich.). Negative control consisted of performing the entire immunohistochemical procedure on adjacent sections with a non-immune IgG isotype control or an omission of the primary antibody.

n. Demonstration of Amyloid: Congo Red and Thioflavin T Staining

Congo red stain was performed to demonstrate TTR amyloid in the tissue using a kit from American MasterTech (Lodi, Calif.). The staining was performed according to the manufacturer's procedure. Slides were stained in the Congo Red solution for 1 hour followed by differentiation in 1% sodium hydroxide for approximately 15 seconds. The slides were then rinsed in running water, dehydrated through an alcohol series of increasing concentrations, and cleared through three changes of xylenes, and coverslipped with CytoSeal 60.

A modified Thioflavin T staining protocol (Schmidt et al 1995.) was employed to determine the presence of TTR amyloid in the tissue. Briefly, slides were counterstained with a Mayers hematoxylin, rinsed in running water and stained with a filtered solution of 0.015% Thioflavin T (T3516-25G; Sigma-Aldrich, St. Louis, Mo.) in 50% ethanol for ten minutes. The slides were then rinsed in running water and differentiated in 1% (v/v) acetic acid for 10 minutes and rinsed three times in water. The slides were allowed to air dry before being coverslipped with ProLong Gold (Life Technologies).

o. Image Analysis

Slides were imaged with either an Olympus BX61 microscope, Hamamatsu Nanozoomer 2.0HT digital slide scanner, or a Leica SPE spectral confocal system. Images were collected and stored as TIFF files.

p. Analysis of Human Plasma Samples by SDS-PAGE/Western

Six plasma samples from patients confirmed for V30M ATTR (Sample #11, #12, #15, #18, #19, #20) and 6 samples (#21, #22, #23, #24, #25, #27) from normal subjects were obtained from M. Saraiva (Porto University, Portugal). Sample #C6 was a normal human serum sample obtained from a commercial source (BioreclamationIVT). These plasma samples were separated by SDS-PAGE and Western blotted with 9D5 or 5A1 as follows. A 1.4 µl volume of plasma was diluted 1:8 into 1×LDS sample buffer in the absence of reducing agent (Life Technologies). Samples were subjected to SDS-PAGE separation and Western blotted with 0.5 µg/ml 9D5 or 5A1 as described previously.

q. Analysis of Human Plasma Samples by MesoScale Discovery (MSD) Plate Assay 96-well MSD plates were coated with monoclonal antibody 6C1 at a concentration of 4 µg/mL in PBS and incubated for 2 hours at room temperature with shaking, or overnight at 4° C. Plates were washed three times with 1×TBST before being blocked with of 3% MSD Blocker A solution, 150 µL per well for 1 hour shaking. A 30 µl per well volume of human plasma samples diluted 1:10 in a sample buffer comprised of 0.6% globulin-free bovine serum albumin, 1.5 mM monobasic sodium phosphate, 8 mM dibasic sodium phosphate, 145 mM sodium chloride, 0.05% Triton X-405, and 0.05% thimerosal was added to the blocked MSD plates for 1 hour. Plates were washed 3 times with 1×TBST. A 50 µl per well volume of 1 µg/ml sulfo-tagged detection antibody (either 8C3 total TTR antibody of the Dako polyclonal antibody) in sample buffer was added for 1 hr. at room temperature with shaking. Plates were washed three times with 1×TBST followed by the addition of 150 µl per well 1× Read Buffer T solution (Meso Scale Discovery). Plates were then read in the MSD Sector imager.

r. Generation of an MSD Standard Curve

In order to quantitate the amount of non-native, 6C1-reactive TTR protein present in human plasma samples, a MSD standard curve was generated using recombinant TTR-F87M/L110M as a 6C1-reactive TTR standard. This TTR variant contains two amino acid substitutions that prevent tetramer formation and keeps the protein in the monomer state (Jiang et al. (2001) Biochemistry 40, 11442-11452). As such, this TTR variant is recognized by all mis-TTR mAbs and is therefore well-suited for use as a reference standard in the MSD assay.

To generate the standard curve, 96-well MSD plates were coated with mis-TTR antibody 6C1 at a concentration of 4 µg/mL in PBS and incubated for 2 hours at room temperature with shaking, or overnight at 4° C. Plates were washed three times with 1×TBST before being blocked with of 3% MSD Blocker A solution, 150 µL per well for 1 hour shaking. The blocked plates were then treated for 1 hour with 50 µl per well of 25 µg/mL TTR-F87M/L110M serially diluted 1:5 with the last dilution being a buffer blank. Plates were washed 3 times with 1×TBST before the addition of a 50 µl per well volume of 1 µg/ml SulfoTag-detection antibody (8C3-SulfoTag or Dako pAb-SulfoTag) for 1 hour at room temperature with shaking. Both 8C3 mAb and the Dako antibody were coupled to the SulfoTag and could be used at the detection antibody since they bound to total TTR and were not conformation specific.

After treatment with the detection antibody, plates were washed three times with a 150 µl per well volume of 1×TBST, followed by the addition of 150 µl per well 1× Read Buffer T (MSD). Plates were read in the MSD Sector imager and a resulting TTR F87M/L110M calibration curve was generated.

s. Phagoctyosis Assay

A 1-mg/mL sample of TTR-F87M/L110M, native TTR or low-pH aggregated TTR-V30M was amine coupled with pHrodo dye for 15 min at 37° C. with a protein:dye ratio of 15:4 according to the manufacturer's specifications (Thermo Scientific). Excess pHrodo-label was removed by diafiltration in a spin concentrator with a 10K molecular weight cutoff (Pierce Thermo) and the pHrodo-TTR was resuspended in 1×PBS.

THP-1 human monocytes were cultured in cell culture media (RMPI, 10% low IgG serum, pen/strep). A 20-µg/mL aliquot of pHrodo-labeled TTR was separately pre-incubated with 40 µg/mL antibody at 37° C. in cell culture media for 30 min prior to the addition of 5E+04 THP-1 cells in a 1:1 volumetric ratio. After tissue culture incubation (3 h), cells were washed with cell culture media three times, incubated in media for 10 min, then washed twice with and resuspended in FACS buffer (1% FBS in PBS). Red pHrodo fluorescence intensity was detected using Texas Red channel filters. Epifluorescence microscopy was carried out in a similar fashion. After FACS analysis, the remaining cells were transferred to glass chamber slides and imaged by inverted microscopy. Mean fluorescence intensities were automatically calculated by averaging the relative fluorescence intensities of each individual cell.

Example 12. Antibody-Dependent Uptake of TTR by THP-1 Cells

Figure 7A:
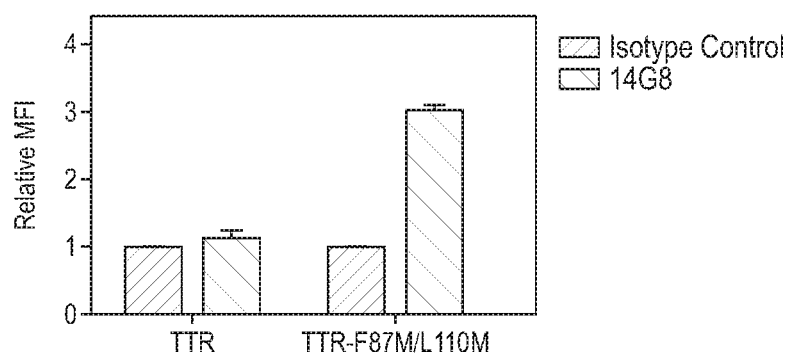
FIGS. 7A & 7B.

TTR-F87M/L110M was covalently labeled with the pH-sensitive fluorescent dye pHrodo. The pHrodo tag has minimal fluorescence under physiological pH, but fluorescence is enhanced upon engulfment into the low pH environments of endocytic vesicles and thus marks cellular uptake of tagged particles. THP-1 monocytes were added to pHrodo-tagged TTR (native or non-native, TTR-F87M/L110M) after treatment with either 14G8 or the isotype control antibody. Low levels of fluorescence were observed with either antibody incubated with native TTR, and after incubation of the control antibody with non-native TTR. Fluorescence was increased, however, after 14G8 incubation with non-native TTR (FIG. 7A), suggesting that non-native TTR is not efficiently phagocytized under basal conditions, however the addition of mis-TTR antibodies specifically elicits phagocytosis of non-native TTR.

Figure 7B:
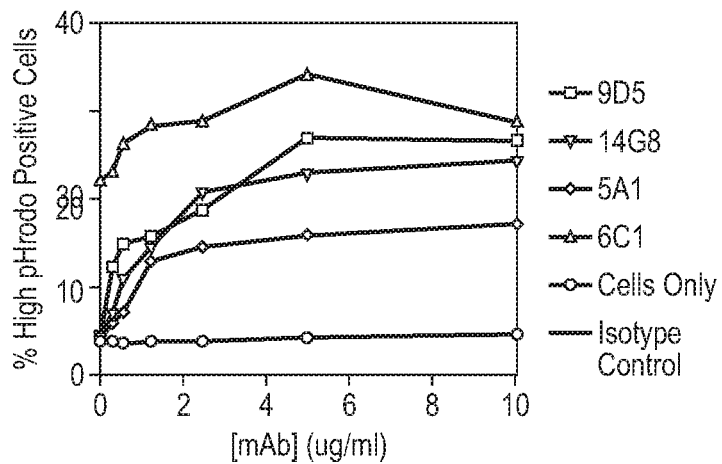

Dose-dependent phagocytosis of pHrodo-labeled, large aggregated fibrillar particles of TTR was also demonstrated for each of the mis-TTR mAbs (FIG. 7B). Maximum antibody-dependent uptake was variable for each mis-TTR mAb (6C1>9D5≈14G8>5A1), reaching a plateau at mAb concentrations between 5-10 µg/mL. Variable antibody potencies may reflect isotype differences and associated changes in effector function among the four mis-TTR mAbs. Controls, including untreated cells or those treated with an IgG1 isotype control, did not demonstrate detectable or enhanced fluorescence, respectively.

Example 13. Evaluation of mis-TTR Antibodies in Transgenic Mouse Model

In vivo studies are conducted in a humanized transgenic mouse model V30M hTTR (Inoue et al., (2008) Specific pathogen free conditions prevent transthyretin amyloidosis in mouse models. Transgenic Research 17:817-826) to assess the efficacy of anti-TTR antibodies in the binding and removal of aggregated hTTR.

Transgenic mice are bred using standard procedures and their circulating hTTR levels are assessed by ELISA. Mice with a serum level of 200-400 µg/ml of hTTR are used for subsequent efficacy studies. The first set of studies examine the natural deposition of hTTR in transgenic mice. Detection of hTTR deposits begins at 12 months of age and is repeated every 3-6 months thereafter. Once an acceptable level of aggregates is seen in transgenic mice, efficacy studies are initiated. Animals are divided into three treatment groups (n=10(group) and treated weekly for four weeks with an IP dose of vehicle, control antibody (isotype control, 10 mpk) or an anti-hTRR antibody (10 mpk). One week after the last treatment the mice are euthanized, tissues collected and processed, and then stained to assess the number and size of remaining TTR deposits. Quantitative methods and statistics are employed to determine the degree of clearance seen among groups.

In an alternative approach, hTTR aggregates are prepared in vitro and then injected into the kidney of transgenic mice to seed the deposition of new aggregates. Applicant has determined that the injection of these preparations can expedite the deposition of new aggregates in a predictable manner. Based on these findings, animals are sedated, the left kidney exposed and pre-aggregated hTTR material injected into the cortex of the kidney. After a suitable recovery period, mice are divided into three treatment groups (n=10/group) and treated weekly for four-eight weeks with an IP dose of vehicle, control antibody (isotype control, 10 mpk) or an anti-hTRR antibody (10 mpk). One week after the last treatment the mice are euthanized, the kidneys collected and processed, and then stained to assess the number and size of TTR deposits. Quantitative methods and statistics are employed to determine the degree of change seen among groups.

Example 14. Evaluation of mis-TTR Antibodies in a Matrigel Implant Model

Applicant has determined that pre-aggregated hTTR can be suspended in Matrigel (BD Bioscience, Cat #354263), allowed to solidify and then placed subcutaneously in mice. At four weeks post implantation, the Matrigel implant maintained its structure and the aggregated hTTR was still present within the implant. Moreover, the implant was well tolerated by the mice and anti-hTTR antibodies were able to penetrate and bind to the aggregates suspended in the Matrigel. Based on these findings, an antibody efficacy study is conducted. Animals are sedated and an implant containing pre-aggregated hTTR suspended in Matrigel placed subcutaneously in mice. After a suitable recovery period, mice are divided into three treatment groups (n=10/group) and treated weekly, for two-four weeks with an IP dose of vehicle, control antibody (isotype control, 10 mpk) or an anti-hTRR antibody (10 mpk). After the last treatment, the mice are euthanized, the skin containing the implant collected and processed, and then the amount of TTR deposits remaining assessed using histological and/or biochemical methods. Quantitative analysis and statistics are employed to determine the degree of clearance seen among groups.

Example 15. Electron and Atomic Force Microscopy

Figure 8A:
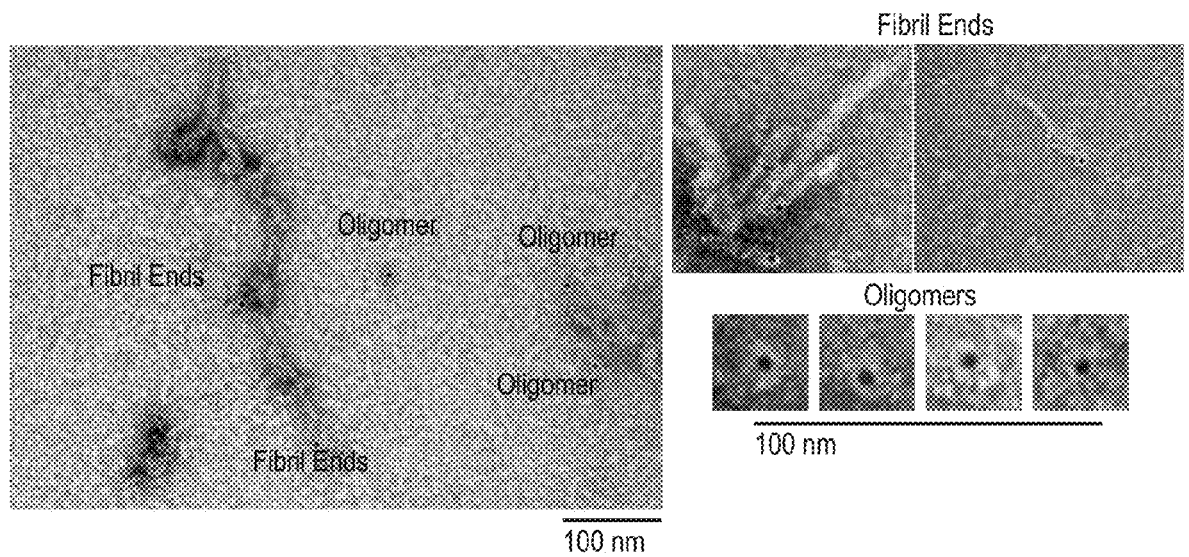
Figure 8B:
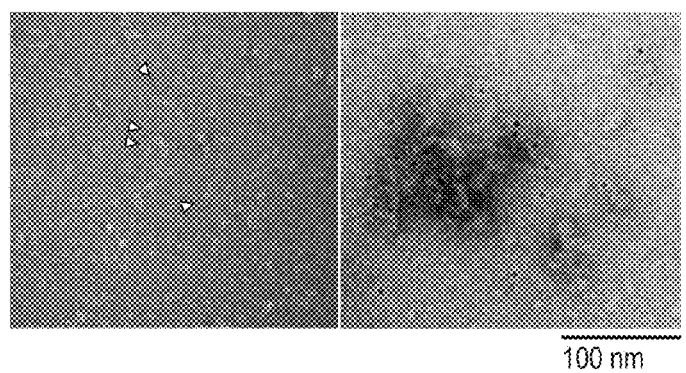
Figure 8C:
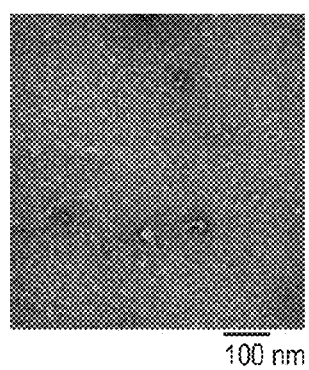
Figure 9B:
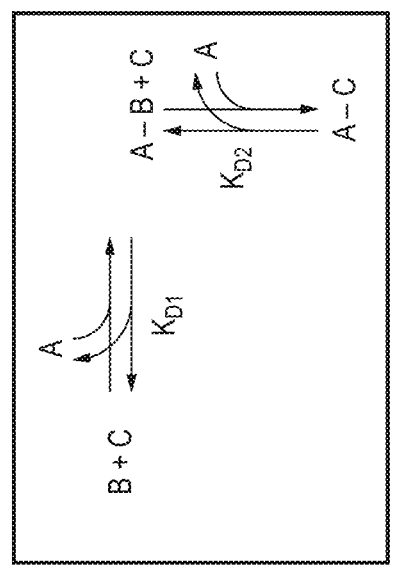
FIG. 9B: Interaction of 14G8 with mature TTR-V122I fibrils assessed using ITC fits to a 2-binding site model. ITC data and binding isotherms for 14G8 binding to aggregated TTR variants are presented in FIG. 8A. Binding was fit to a 2-binding site model with KD values shown (FIG. 8B).

Immunogold transmission electron microscopy (TEM) and atomic force microscopy (AFM) were used to generate images of the interaction between mis-TTR mAbs and both aggregated and fibrillar forms of the protein. Isothermal titration calorimetry (ITC) was carried out by titrating 14G8 into a solution of aggregated TTR using standard methods. Using TEM, immunogold labeling with 14G8 was observed in TTR-V122I oligomer aggregates and fibril ends (FIG. 8A), whereas immunogold labeling with an anti-TTR pAb shows binding along the lengths of TTR fibers and to oligomeric clusters (FIG. 8B). IgG1 isotype control mAb does not show immunogold labeling (FIG. 8C). TTR-V122I fibers, alone and in the presence of 14G8±6 nm colloidal gold-conjugated secondary antibody, were assessed using AFM. Gold labeling was observed at fiber ends (FIG. 8D). FIG. 9A shows isothermal titration calorimetry (ITC) data and binding isotherms for 14G8 binding to aggregated TTR variants. FIG. 9B shows binding fitted to a 2-binding site model with KD values shown. TEM, AFM, and ITC analysis provide evidence mis-TTR mAbs bind to TTR aggregates and fibrils primarily at 2 distinct sites: oligomers and fibril ends.

Example 16. Antibody Binding to TTR Amyloid in the Peripheral Nerves and Gastrointestinal Tract of a Patient with ATTR Amyloidosis from a TTR-V30M Mutation 14G8 and control antibodies were evaluated immunohistochemically to determine their reactivity for TTR amyloid deposits in nerve, and gastrointestinal tract samples obtained from patients with confirmed diagnoses of ATTR amyloidosis from a V30M mutation. FIGS. 10A-G show 14G8 immunolabeled TTR amyloid present between fibers of the nerve fascicle (FIG. 10A panels 1 and 2), which overlapped with staining by Congo red (FIG. 10B panels 1 and 2) and thioflavin T (FIG. 10C panels 1 and 2), and immunolabeling by a total-TTR antibody (FIG. 10D) in tissue derived from a patient with ATTR amyloidosis. No staining was seen with the use of 2 isotype control antibodies (FIGS. 10E-F); however, axonal degeneration (lack of Schwann cell nuclei) in the areas laden with TTR amyloid deposits were also observed (FIGS. 10E-F [red areas in 10E]). Peripheral nerves from a healthy control were not labeled using either 14G8 or a total-TTR antibody (FIG. 10G panels 1-3).

14G8 labelled TTR amyloid deposited throughout the gastrointestinal tract; Meissner's plexus and glands in the esophagus (FIG. 11A, B panels 1), the rich vasculature bed in the submucosa (FIG. 11C panel 1), and the muscularis propria (MP) and muscularis mucosa (MM) of the jejunum (FIG. 11D panel 1) were immunolabeled with 14G8. 14G8-positive TTR amyloid overlapped with Congo red fluorescent staining (FIGS. 11A-D panels 2). ATTR amyloidosis tissue stained with an isotype control mAb (FIGS. 119A-D panels 3). 14G8 immunoreactivity was absent in healthy control tissue (FIG. 11E panels 1-4).

These findings provide evidence that mis-TTR mAbs can be useful in preventing the deposition or enhancing the clearance, or both, of TTR amyloid in patients with ATTR amyloidosis regardless of the specific organ(s) involved while sparing the function of the normal tetrameric form of the protein.

---

What is claimed is:

1. An antibody that binds to human transthyretin comprising a mature heavy chain variable region comprising three heavy chain CDRs having sequences comprising SEQ ID NOs: 67-69 respectively, and a mature light chain variable region comprising three light chain CDRs having sequences comprising SEQ ID NOS. 77-79, respectively, except that positions H52 and L26 by Kabat numbering are independently each N or S.

2. The antibody of claim 1, wherein the antibody is a monoclonal antibody.

3. The antibody of claim 1, wherein the antibody is a chimeric, humanized, or veneered antibody.

4. The antibody of claim 1, wherein the antibody has a human IgG1 isotype.

5. The antibody of claim 1, wherein the antibody has a human IgG2 or IgG4 isotype.

6. The antibody of claim 1, wherein the antibody is a chimeric antibody.

7. The antibody of claim 1, wherein heavy chain CDR-H1 has the sequence of SEQ ID NO: 118.

8. The antibody of claim 1, which is a humanized antibody.

9. The humanized antibody of claim 8, wherein position H1 is occupied by E, position H47 is occupied by L, position L26 is occupied by S, position L36 is occupied by F and position L60 is occupied by S.

10. The humanized antibody of claim 8, wherein the mature heavy chain variable region has the amino acid sequence of any one of SEQ ID NOS: 64-66, and the mature light chain variable region has the amino acid sequence of any one of SEQ ID NOS: 74-76, wherein the R at position L107 is optional.

11. The humanized antibody of claim 8 comprising a humanized mature heavy chain variable region having an amino acid sequence at least 90% identical to any one of SEQ ID NOS: 64-66 and a humanized mature light chain variable region having an amino acid sequence at least 90% identical to any one of SEQ ID NOS: 74-76, except that position H82a is N or S, position H83 is R or K, position H84 is A or S, position H89 is V or M, and position L18 is S or P, wherein positions are defined by Kabat numbering.

12. The humanized antibody of claim 11, wherein at least one of the following positions is occupied by the amino acid as specified: position H1 is occupied by E, position H47 is occupied by L, and position L36 is occupied by F, wherein positions are defined by Kabat numbering.

13. The humanized antibody of claim 12, wherein positions H1 and H47 are occupied by E and L, respectively, wherein positions are defined by Kabat numbering.

14. The humanized antibody of claim 12, wherein position L36 is occupied by F, wherein the position is defined by Kabat numbering.

15. The humanized antibody of claim 11, wherein at least one of the following positions is occupied by the amino acid as specified: position H3 is occupied by K, position H105 is occupied by T, position L8 is occupied by A, position L9 is occupied by P, position L19 is occupied by V, position L26 is occupied by S, position L60 is occupied by S, and position L70 is occupied by A wherein positions are defined by Kabat numbering.

16. The humanized antibody of claim 15, wherein positions H3 and H105 are occupied by K and T, respectively, wherein positions are defined by Kabat numbering.

17. The humanized antibody of claim 15, wherein positions L8, L9, L19, and L70 are occupied by A, P, V, and A, respectively, wherein positions are defined by Kabat numbering.

18. The humanized antibody of claim 15, wherein positions L26 and L60 are each occupied by S, wherein positions are defined by Kabat numbering.

19. The humanized antibody of claim 11, comprising a mature heavy chain variable region having an amino acid sequence at least 95% identical to any one of SEQ ID NOS: 64-66 and a mature light chain variable region having an amino acid sequence at least 95% identical to any one of SEQ ID NOS: 74-76, except that position H82a is N or S, position H83 is R or K, position H84 is A or S, position H89 is V or M, and position L18 is S or P, wherein positions are defined by Kabat numbering.

20. The humanized antibody of claim 19, comprising a mature heavy chain variable region having an amino acid sequence at least 98% identical to any one of SEQ ID NOS: 64-66 and a mature light chain variable region having an amino acid sequence at least 98% identical to any one of SEQ ID NOS: 74-76, except that position H82a is N or S, position H83 is R or K, position H84 is A or S, position H89 is V or M, and position L18 is S or P, wherein positions are defined by Kabat numbering.

21. The humanized antibody of claim 20, wherein the mature heavy chain variable region has the amino acid sequence of any one of SEQ ID NOS: 64-66, and the mature light chain variable region has the amino acid sequence of any one of SEQ ID NOS: 74-76.

22. The humanized antibody of claim 21, wherein the mature heavy chain variable region has the amino acid sequence of SEQ ID NO: 65 and the mature light chain variable region has the amino acid sequence of SEQ ID NO: 76.

23. The antibody of claim 1, wherein the antibody is an intact antibody.

24. The antibody of claim 1, wherein the antibody is a binding fragment.

25. The antibody of claim 24, wherein the binding fragment is a single-chain antibody, Fab, or Fab'2 fragment.

26. The humanized antibody of any one of claim 1, 11 or 22, wherein the mature light chain variable region is fused to a light chain constant region and the mature heavy chain variable region is fused to a heavy chain constant region.

27. The humanized antibody of claim 26, wherein the heavy chain constant region is a mutant form of a natural human heavy chain constant region which has reduced binding to an Fc receptor relative to the natural human heavy chain constant region.

28. The humanized antibody of claim 26, wherein the heavy chain constant region is of an IgG1 isotype.

29. The humanized antibody of claim 26, wherein the mature heavy chain variable region is fused to a heavy chain constant region having the sequence of SEQ ID NO: 103 with or without the C-terminal lysine and/ or the mature light chain variable region is fused to a light chain constant region having the sequence of SEQ ID NO: 104 or 105.

30. A pharmaceutical composition comprising the antibody of claim 1 and a pharmaceutically acceptable carrier.

31. A nucleic acid encoding the heavy chain and light chain of the antibody in claim 1.

32. The nucleic acid of claim 31 having the sequence comprising any one of SEQ ID NOS: 87, 89 and 91-96.

33. The nucleic acid of claim 32, wherein the sequence comprises SEQ ID NOS. 92 and 96 encoding the heavy and light chains respectively.

34. The nucleic acid of claim 33, wherein the sequence further comprises SEQ ID NOS. 106 linked to SEQ ID NO: 92 and SEQ ID NO: 108 linked to SEQ ID NO: 96.

35. A recombinant expression vector comprising the nucleic acid of claim 31.

36. A host cell transformed with the recombinant expression vector of claim 35.

37. A method of humanizing an antibody, the method comprising:
    (a) selecting one or more acceptor antibodies;
    (b) identifying the amino acid residues of a mouse antibody to be retained;
    (c) synthesizing a nucleic acid encoding a humanized heavy chain comprising CDRs of the mouse antibody heavy chain and a nucleic acid encoding a humanized light chain comprising CDRs of the mouse antibody light chain; and
    (d) expressing the nucleic acids in a host cell to produce a humanized antibody; wherein the mouse antibody comprises the heavy chain variable region of SEQ ID NO: 61 and the light chain variable region of SEQ ID NO: 70.

38. A method of producing a humanized, chimeric, or veneered antibody, the method comprising:
    (a) culturing cells transformed with nucleic acids encoding the heavy and light chains of the antibody, so that the cells secrete the antibody; and
    (b) purifying the antibody from cell culture media; wherein the antibody is a humanized, chimeric, or veneered form of the antibody of claim 1.

39. A method of producing a cell line producing a humanized, chimeric, or veneered antibody, the method comprising:
    (a) introducing a vector encoding heavy and light chains of an antibody and a selectable marker into cells;
    (b) propagating the cells under conditions to select for cells having increased copy number of the vector;
    (c) isolating single cells from the selected cells; and
    (d) banking cells cloned from a single cell selected based on yield of antibody; wherein the antibody is a humanized, chimeric, or veneered form of the antibody of claim 1.

40. The method of claim 39, further comprising propagating the cells under selective conditions and screening for cell lines naturally expressing and secreting at least 100 mg/L/$10^6$ cells/24h.

41. A method of inhibiting or reducing aggregation of transthyretin in a subject having a transthyretin-mediated amyloidosis an effective regime of the antibody of claim 1, comprising administering to the subject an effective thereby inhibiting or reducing aggregation of transthyretin in the subject.

42. The method of claim 41, wherein the transthyretin-mediated amyloidosis is associated with amyloid accumulation in the heart, peripheral nervous system, autonomic nervous system, kidneys, eyes, or gastrointestinal tract of the subject.

43. The method of claim 41, wherein the antibody comprises a mature heavy chain variable region having the amino acid sequence of SEQ ID NO: 65 and a mature light variable region having the amino acid sequence of SEQ ID NO: 76.

44. The method of claim 43, wherein the mature heavy chain variable region is fused to a human IgG1 heavy chain constant region, and the mature light chain variable region is fused to a human kappa light chain constant region.

45. The method of claim 43, wherein the antibody comprises a mature heavy chain having the amino acid sequence of SEQ ID NO: 82 with or without the C-terminal lysine and mature light chain having the amino acid sequence of SEQ ID NO: 86.

46. A method of inhibiting or reducing transthyretin fibril formation in a subject having a transthyretin-mediated amyloidosis, comprising administering to the subject an effective regime of the antibody of claim 1, thereby inhibiting or reducing transthyretin accumulation in the subject.

47. The method of claim 46, wherein the antibody comprises a mature heavy chain variable region having the amino acid sequence of SEQ ID NO: 65 and a mature light variable region having the amino acid sequence of SEQ ID NO: 76.

48. The method of claim 47, wherein the mature heavy chain variable region is fused to a human IgG1 heavy chain constant region, and the mature light chain variable region is fused to a human kappa light chain constant region.

49. The method of claim 47, wherein the antibody comprises a mature heavy chain having the amino acid sequence of SEQ ID NO: 82 with or without the C-terminal lysine and mature light chain having the amino acid sequence of SEQ ID NO: 86.

50. A method of reducing transthyretin deposits in a subject having a transthyretin-mediated amyloidosis, comprising administering to the subject an effective regime of the antibody of claim 1, thereby reducing transthyretin deposits in the subject.

51. The method of claim 50, wherein the antibody comprises a mature heavy chain variable region having the amino acid sequence of SEQ ID NO: 65 and a mature light variable region having the amino acid sequence of SEQ ID NO: 76.

52. The method of claim 51, wherein the mature heavy chain variable region is fused to a human IgG1 heavy chain constant region, and the mature light chain variable region is fused to a human kappa light chain constant region.

53. The method of claim 51, wherein the antibody comprises a mature heavy chain having the amino acid sequence of SEQ ID NO: 82 with or without the C-terminal lysine and mature light chain having the amino acid sequence of SEQ ID NO: 86.

54. A method of clearing aggregated transthyretin in a subject having a transthyretin-mediated amyloidosis, comprising administering to the subject an effective regime of the antibody of claim 1, thereby clearing aggregated transthyretin from the subject relative to a subject having a transthyretin mediated amyloidosis who has not received the antibody.

55. The method of claim 54, wherein the antibody comprises a mature heavy chain variable region having the amino acid sequence of SEQ ID NO: 65 and a mature light variable region having the amino acid sequence of SEQ ID NO: 76.

56. The method of claim 55, wherein the mature heavy chain variable region is fused to a human IgG1 heavy chain constant region, and the mature light chain variable region is fused to a human kappa light chain constant region.

57. The method of claim 55, wherein the antibody comprises a mature heavy chain having the amino acid sequence of SEQ ID NO: 82 with or without the C-terminal lysine and mature light chain having the amino acid sequence of SEQ ID NO: 86.

58. A method of stabilizing a non-toxic conformation of transthyretin in a subject having a transthyretin-mediated amyloidosis, comprising administering to the subject an effective regime of the antibody of claim 1, thereby stabilizing a non-toxic conformation of transthyretin in the subject.

59. The method of claim 58, wherein the antibody comprises a mature heavy chain variable region having the amino acid sequence of SEQ ID NO: 65 and a mature light variable region having the amino acid sequence of SEQ ID NO: 76.

60. The method of claim 59, wherein the mature heavy chain variable region is fused to a human IgG1 heavy chain constant region, and the mature light chain variable region is fused to a human kappa light chain constant region.

61. The method of claim 59, wherein the antibody comprises a mature heavy chain having the amino acid sequence of SEQ ID NO: 82 with or without the C-terminal lysine and mature light chain having the amino acid sequence of SEQ ID NO: 86.

62. A method of treating a transthyretin-mediated amyloidosis in a subject, comprising administering to the subject an effective regime of the antibody of claim 1.

63. The method of claim 62, wherein the antibody comprises a mature heavy chain variable region having the amino acid sequence of SEQ ID NO: 65 and a mature light variable region having the amino acid sequence of SEQ ID NO: 76.

64. The method of claim 63, wherein the mature heavy chain variable region is fused to a human IgG1 heavy chain constant region, and the mature light chain variable region is fused to a human kappa light chain constant region.

65. The method of claim 63, wherein the antibody comprises a mature heavy chain having the amino acid sequence of SEQ ID NO: 82 with or without the C-terminal lysine and mature light chain having the amino acid sequence of SEQ ID NO: 86.

66. A method of treating a subject having cardiomyopathy or hypertrophy, familial amyloid polyneuropathy, central nervous system selective amyloidosis (CNSA), senile systemic amyloidosis, senile cardiac amyloidosis, spinal stenosis, osteoarthritis, rheumatoid arthritis, juvenile idiopathic arthritis, age related macular degeneration, and a ligament or tendon disorder, the method comprising administering to the subject an effective regime of the antibody of claim 1.

67. The method of claim 66, wherein the antibody comprises a mature heavy chain variable region having the amino acid sequence of SEQ ID NO: 65 and a mature light variable region having the amino acid sequence of SEQ ID NO: 76.

68. The method of claim 67, wherein the mature heavy chain variable region is fused to a human IgG1 heavy chain constant region, and the mature light chain variable region is fused to a human kappa light chain constant region.

69. The method of claim 68, wherein the antibody comprises a mature heavy chain having the amino acid sequence of SEQ ID NO: 82 with or without the C-terminal lysine and mature light chain having the amino acid sequence of SEQ ID NO: 86.

70. A method of diagnosing a transthyretin-mediated amyloidosis in a subject, comprising contacting a biological sample from the subject with an effective amount of the antibody of claim 1.

71. The method of claim 70, further comprising detecting the binding of antibody to transthyretin, wherein the presence of bound antibody indicates the subject has a transthyretin-mediated amyloidosis.

72. The method of claim 70, further comprising comparing binding of the antibody to the biological sample with binding of the antibody to a control sample, whereby increased binding of the antibody to the biological sample relative to the control sample indicates the subject has a transthyretin-mediated amyloidosis.

73. The method of claim 72, wherein the biological sample and the control sample comprise cells of the same tissue origin.

74. The method of claim 70, wherein the biological sample and/or the control sample is blood, serum, plasma, or solid tissue.

75. The method of claim 74, wherein the solid tissue is from the heart, peripheral nervous system, autonomic nervous system, kidneys, eyes, or gastrointestinal tract.

76. A method of detecting the presence or absence of transthyretin deposits in a subject, comprising contacting a biological sample from the subject suspected of comprising the amyloid accumulation with an effective amount of the antibody of claim 1.

77. A method of determining a level of transthyretin deposits in a subject, comprising administering the antibody of claim 1 and detecting the presence of bound antibody in the subject.

78. The method of claim 77, wherein the presence of bound antibody is determined by positron emission tomography (PET).

\* \* \* \* \*

UNITED STATES PATENT AND TRADEMARK OFFICE
CERTIFICATE OF CORRECTION

PATENT NO. : 10,464,999 B2
APPLICATION NO. : 15/201423
DATED : November 05, 2019
INVENTOR(S) : Yue Liu et al.

Page 1 of 1

It is certified that error appears in the above-identified patent and that said Letters Patent is hereby corrected as shown below:

In the Claims

Claim 27, Column 180, Line 66:
Delete "an Fc receptor"
And insert --a Fcγ receptor--

Signed and Sealed this
Thirty-first Day of December, 2019

Andrei Iancu
*Director of the United States Patent and Trademark Office*

SEQUENCE LISTING

```
<160> NUMBER OF SEQ ID NOS: 118

<210> SEQ ID NO 1
<211> LENGTH: 124
<212> TYPE: PRT
<213> ORGANISM: Artificial Sequence
<220> FEATURE:
<223> OTHER INFORMATION: m9D5VH

<400> SEQUENCE: 1

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30
```

```
Thr Met Ser Trp Val Arg Gln Thr Pro Glu Lys Arg Leu Glu Leu Val
            35                  40                  45

Ala Glu Ile Ser Asn Ser Gly Asp Thr Thr Tyr Tyr Pro Asp Thr Val
 50                  55                  60

Lys Gly Arg Phe Thr Phe Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg His Tyr Tyr Gly Gly Tyr Gly Gly Trp Phe Phe Asp
                100                 105                 110

Val Trp Gly Thr Gly Thr Thr Val Thr Val Ser Ser
            115                 120

<210> SEQ ID NO 2
<211> LENGTH: 123
<212> TYPE: PRT
<213> ORGANISM: Artificial Sequence
<220> FEATURE:
<223> OTHER INFORMATION: 1SEQ_H

<400> SEQUENCE: 2

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Thr Tyr
                20                  25                  30

Thr Met Ser Trp Ala Arg Gln Thr Pro Glu Lys Lys Leu Glu Trp Val
            35                  40                  45

Ala Tyr Ile Ser Lys Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Leu Tyr Tyr Cys
                85                  90                  95

Ala Arg Gly Ala Met Phe Gly Asn Asp Phe Lys Tyr Pro Met Asp Arg
                100                 105                 110

Trp Gly Gln Gly Thr Ser Val Thr Val Ser Ser
            115                 120

<210> SEQ ID NO 3
<211> LENGTH: 124
<212> TYPE: PRT
<213> ORGANISM: Artificial Sequence
<220> FEATURE:
<223> OTHER INFORMATION: BAC02114

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Thr Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95
```

```
Ala Arg Gly Gly Gln Gly Ser Arg Tyr Tyr Tyr Tyr Gly Met Asp
            100                 105                 110

Val Trp Gly Gln Gly Thr Thr Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: AAX82494

<400> SEQUENCE: 4

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser
        115                 120

<210> SEQ ID NO 5
<211> LENGTH: 124
<212> TYPE: PRT
<213> ORGANISM: Artificial Sequence
<220> FEATURE:
<223> OTHER INFORMATION: Hu9D5VHv1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Ser Leu Lys Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Thr Val Thr Val Ser Ser
        115                 120

<210> SEQ ID NO 6
<211> LENGTH: 124
<212> TYPE: PRT
```

<213> ORGANISM: Artificial Sequence
<220> FEATURE:
<223> OTHER INFORMATION: Hu9D5VHv2

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Thr Val Thr Val Ser Ser
        115                 120
```

<210> SEQ ID NO 7
<211> LENGTH: 124
<212> TYPE: PRT
<213> ORGANISM: Artificial Sequence
<220> FEATURE:
<223> OTHER INFORMATION: Hu9D5VHv2b

<400> SEQUENCE: 7

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
        115                 120
```

<210> SEQ ID NO 8
<211> LENGTH: 124
<212> TYPE: PRT
<213> ORGANISM: Artificial Sequence
<220> FEATURE:
<223> OTHER INFORMATION: Hu9D5VHv3

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

Thr Met Ser Trp Val Arg Gln Ala Pro Gly Lys Gly Leu Glu Trp Val
            35                  40                  45

Ser Glu Ile Ser Asn Ser Gly Asp Thr Thr Tyr Tyr Pro Asp Thr Val
        50                  55                  60

Lys Gly Arg Phe Thr Phe Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Val Thr Val Ser Ser
            115                 120

<210> SEQ ID NO 9
<211> LENGTH: 124
<212> TYPE: PRT
<213> ORGANISM: Artificial Sequence
<220> FEATURE:
<223> OTHER INFORMATION: Hu9D5VHv3b

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Gly Lys Arg Leu Glu Leu Val
            35                  40                  45

Ala Glu Ile Ser Asn Ser Gly Asp Thr Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser
            115                 120

<210> SEQ ID NO 10
<211> LENGTH: 124
<212> TYPE: PRT
<213> ORGANISM: Artificial Sequence
<220> FEATURE:
<223> OTHER INFORMATION: Hu9D5VHv4

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
            35                  40                  45

Ser Glu Ile Ser Asn Ser Gly Asp Thr Thr Tyr Tyr Pro Asp Thr Val
        50                  55                  60

Lys Gly Arg Phe Thr Ile Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys 85                  90                  95
Ala Arg His Tyr Tyr Tyr Gly Gly Gly Tyr Gly Gly Trp Phe Phe Asp
                100                 105                 110

Val Trp Gly Gln Gly Thr Thr Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: Hu9D5VHv4b

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Ala Pro Gly Lys Arg Leu Glu Leu Val
            35                  40                  45

Ala Glu Ile Ser Asn Ser Gly Asp Thr Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
                100                 105                 110

Val Trp Gly Gln Gly Thr Leu Val Thr Val Ser Ser
        115                 120

<210> SEQ ID NO 12
<211> LENGTH: 124
<212> TYPE: PRT
<213> ORGANISM: Artificial Sequence
<220> FEATURE:
<223> OTHER INFORMATION: Hu9D5VHv5

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Leu Val
            35                  40                  45

Ala Glu Ile Ser Asn Ser Gly Asp Thr Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Asn Leu Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
                100                 105                 110

Val Trp Gly Gln Gly Thr Thr Val Thr Val Ser Ser
        115                 120

<210> SEQ ID NO 13
<211> LENGTH: 5

```
<212> TYPE: PRT
<213> ORGANISM: Artificial Sequence
<220> FEATURE:
<223> OTHER INFORMATION: 9D5 CDRH1 - Kabat

<400> SEQUENCE: 13

Ser Tyr Thr Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: 9D5 CDRH2 - Kabat

<400> SEQUENCE: 14

Glu Ile Ser Asn Ser Gly Asp Thr Thr Tyr Tyr Pro Asp Thr Val Lys
1               5                   10                  15

Gly

<210> SEQ ID NO 15
<211> LENGTH: 15
<212> TYPE: PRT
<213> ORGANISM: Artificial Sequence
<220> FEATURE:
<223> OTHER INFORMATION: 9D5 CDRH3 - Kabat

<400> SEQUENCE: 15

His Tyr Tyr Tyr Gly Gly Gly Tyr Gly Gly Trp Phe Phe Asp Val
1               5                   10                  15

<210> SEQ ID NO 16
<211> LENGTH: 112
<212> TYPE: PRT
<213> ORGANISM: Artificial Sequence
<220> FEATURE:
<223> OTHER INFORMATION: m9D5VL

<400> SEQUENCE: 16

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: 1MJU_L

<400> SEQUENCE: 17
```

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Phe Thr Phe Gly Ala Gly Thr Lys Leu Glu Leu Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: ABC66952

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Asn Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Ser Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Tyr Thr Phe Gly Gln Gly Thr Lys Leu Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Hu9D5VLv1

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

-continued

```
Leu Glu Tyr Pro Leu Thr Phe Gly Gln Gly Thr Lys Leu Glu Ile Lys
                100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Hu9D5VLv2

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
                100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Hu9D5VLv3

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
                100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Hu9D5VLv4

<400> SEQUENCE: 22

Asp Ile Val Met Thr Gln Ser Ala Pro Ser Leu Pro Val Thr Pro Gly
1               5                   10                  15
```

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Hu9D5VLv5

<400> SEQUENCE: 23

Asp Ile Val Met Thr Gln Ser Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 24
<211> LENGTH: 16
<212> TYPE: PRT
<213> ORGANISM: Artificial Sequence
<220> FEATURE:
<223> OTHER INFORMATION: 9D5 CDRL1 - Kabat

<400> SEQUENCE: 24

Arg Ser Ser Lys Ser Leu Leu His Ser Asn Gly Asn Thr Tyr Leu Tyr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: 9D5 CDRL2 - Kabat

<400> SEQUENCE: 25

Arg Val Ser Asn Leu Ala Ser
1               5

<210> SEQ ID NO 26
<211> LENGTH: 9
<212> TYPE: PRT

<213> ORGANISM: Artificial Sequence
<220> FEATURE:
<223> OTHER INFORMATION: 9D5 CDRL3 - Kabat

<400> SEQUENCE: 26

Met Gln His Leu Glu Tyr Pro Leu Thr
1               5

<210> SEQ ID NO 27
<211> LENGTH: 454
<212> TYPE: PRT
<213> ORGANISM: Artificial Sequence
<220> FEATURE:
<223> OTHER INFORMATION: Hu9D5 H1 heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Ser Leu Lys Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

```
Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 28
<211> LENGTH: 454
<212> TYPE: PRT
<213> ORGANISM: Artificial Sequence
<220> FEATURE:
<223> OTHER INFORMATION: Hu9D5 H2 heavy chain

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
50                  55                  60

Lys Gly Arg Phe Thr Phe Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220
```

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 29
<211> LENGTH: 454
<212> TYPE: PRT
<213> ORGANISM: Artificial Sequence
<220> FEATURE:
<223> OTHER INFORMATION: Hu9D5 H2b heavy chain

<400> SEQUENCE: 29

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Tyr Tyr Tyr Gly Gly Tyr Gly Gly Trp Phe Phe Asp
        100                 105                 110

Val Trp Gly Gln Gly Thr Leu Val Thr Val Ser Ser Ala Ser Thr Lys
    115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 30
<211> LENGTH: 454
<212> TYPE: PRT
<213> ORGANISM: Artificial Sequence
<220> FEATURE:
<223> OTHER INFORMATION: Hu9D5 H3 heavy chain

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Thr Met Ser Trp Val Arg Gln Ala Pro Gly Lys Gly Leu Glu Trp Val
        35                  40                  45

Ser Glu Ile Ser Asn Ser Gly Asp Thr Thr Tyr Tyr Pro Asp Thr Val
 50                  55                  60

Lys Gly Arg Phe Thr Phe Ser Arg Asp Asn Ala Lys Asn Ser Leu Tyr
 65                  70                  75                  80

Leu Gln Ser Asn Leu Leu Arg Ala Glu Asp Thr Ala Val Tyr Tyr Cys
                85                  90                  95

Ala Arg His Tyr Tyr Gly Gly Tyr Gly Gly Trp Phe Phe Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
```

<210> SEQ ID NO 31
<211> LENGTH: 454
<212> TYPE: PRT
<213> ORGANISM: Artificial Sequence
<220> FEATURE:
<223> OTHER INFORMATION: Hu9D5 H3b heavy chain

<400> SEQUENCE: 31

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Gly Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
```

```
                355                 360                 365
Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
450

<210> SEQ ID NO 32
<211> LENGTH: 454
<212> TYPE: PRT
<213> ORGANISM: Artificial Sequence
<220> FEATURE:
<223> OTHER INFORMATION: Hu9D5 H4 heavy chain

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
                35                  40                  45

Ser Glu Ile Ser Asn Ser Gly Asp Thr Thr Tyr Tyr Pro Asp Thr Val
50                  55                  60

Lys Gly Arg Phe Thr Ile Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Tyr Gly Gly Trp Phe Phe Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
```

```
                260                 265                 270
Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 33
<211> LENGTH: 454
<212> TYPE: PRT
<213> ORGANISM: Artificial Sequence
<220> FEATURE:
<223> OTHER INFORMATION: Hu9D5 H4b heavy chain

<400> SEQUENCE: 33

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Ala Pro Gly Lys Arg Leu Glu Leu Val
            35                  40                  45

Ala Glu Ile Ser Asn Ser Gly Asp Thr Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
                165                 170                 175
Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 34
<211> LENGTH: 454
<212> TYPE: PRT
<213> ORGANISM: Artificial Sequence
<220> FEATURE:
<223> OTHER INFORMATION: Hu9D5 H5 heavy chain

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
```

```
            65                  70                  75                  80
Leu Gln Met Asn Leu Leu Arg Ala Glu Asp Thr Ala Val Tyr Tyr Cys
                85                  90                  95

Ala Arg His Tyr Tyr Gly Gly Tyr Gly Gly Trp Phe Phe Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 35
<211> LENGTH: 219
<212> TYPE: PRT
<213> ORGANISM: Artificial Sequence
```

<220> FEATURE:
<223> OTHER INFORMATION: Hu9D5 L1 light chain

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 36
<211> LENGTH: 219
<212> TYPE: PRT
<213> ORGANISM: Artificial Sequence
<220> FEATURE:
<223> OTHER INFORMATION: Hu9D5 L2 light chain

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu

```
                115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 37
<211> LENGTH: 219
<212> TYPE: PRT
<213> ORGANISM: Artificial Sequence
<220> FEATURE:
<223> OTHER INFORMATION: Hu9D5 L3 light chain

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Asn Thr Tyr Leu Tyr Trp Tyr Leu Gln Lys Pro Gly Gln Ser
            35                  40                  45

Pro Gln Leu Leu Ile Tyr Arg Val Ser Asn Leu Ala Ser Gly Val Pro
        50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 38
<211> LENGTH: 219
<212> TYPE: PRT
<213> ORGANISM: Artificial Sequence
<220> FEATURE:
<223> OTHER INFORMATION: Hu9D5 L4 light chain
```

<400> SEQUENCE: 38

Asp Ile Val Met Thr Gln Ser Ala Pro Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 39
<211> LENGTH: 219
<212> TYPE: PRT
<213> ORGANISM: Artificial Sequence
<220> FEATURE:
<223> OTHER INFORMATION: Hu9D5 L5 light chain

<400> SEQUENCE: 39

Asp Ile Val Met Thr Gln Ser Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 40
<211> LENGTH: 429
<212> TYPE: DNA
<213> ORGANISM: Artificial Sequence
<220> FEATURE:
<223> OTHER INFORMATION: m9D5VH with signal peptide

<400> SEQUENCE: 40
atggactttg ggctcagctt gattttcctt gtccttgttt taaaaggtgt cctgtgtgaa      60
gtgaagctgg tggagtctgg gggaggttta gtgcagcctg agggtccct gaaactctcc     120 tgtgcagcct ctggattcac tttcagtagc ataccatgt cttgggttcg ccagactcca     180
gaaaagaggc tggagttggt cgcagaaatt agtaatagtg gtgataccac ctactatcca     240
gacactgtaa agggccgatt caccttctcc agagacaatg ccaagaacac cctgtacctg     300
caaatgagca gtctgaagtc tgaggacacg gccatgtatt actgtgcaag acattattac     360
tatggtggtg gctacggggg gtggttcttc gatgtctggg gcacagggac cacggtcacc     420
gtctcctcg                                                             429

<210> SEQ ID NO 41
<211> LENGTH: 143
<212> TYPE: PRT
<213> ORGANISM: Artificial Sequence
<220> FEATURE:
<223> OTHER INFORMATION: m9D5VH with signal peptide

<400> SEQUENCE: 41

Met Asp Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Leu Val Ala Glu Ile Ser Asn Ser Gly Asp Thr Thr Tyr Tyr Pro
65                  70                  75                  80

Asp Thr Val Lys Gly Arg Phe Thr Phe Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Tyr Tyr Tyr Gly Gly Gly Tyr Gly Gly Trp
        115                 120                 125

Phe Phe Asp Val Trp Gly Thr Gly Thr Thr Val Thr Val Ser Ser
```

<210> SEQ ID NO 42
<211> LENGTH: 396
<212> TYPE: DNA
<213> ORGANISM: Artificial Sequence
<220> FEATURE:
<223> OTHER INFORMATION: m9D5VL with signal peptide

<400> SEQUENCE: 42

```
atgaggtgcc tagctgagtt cctggggctg cttgtgctct ggatccctgg agccattggg      60
gatattgtga tgactcaggc tgcaccctct gtacctgtca ctcctggaga gtcagtatcc     120
atctcctgca ggtctagtaa gagtctcctg catagtaatg caacactta cttgtattgg     180
ttcctgcaga ggccaggcca gtctcctcaa ctcctgatat atcgggtgtc caaccttgcc     240
tcaggagtcc cagacaggtt cagtggcagt gggtcaggaa ctgctttcac actgagaatc     300
agtagagtgg aggctgagga tgtgggtgtt tattactgta tgcaacattt agaatatccg     360
ctcacgttcg gtgctgggac caagctggag ctgaaa                              396
```

<210> SEQ ID NO 43
<211> LENGTH: 132
<212> TYPE: PRT
<213> ORGANISM: Artificial Sequence
<220> FEATURE:
<223> OTHER INFORMATION: m9D5VL with signal peptide

<400> SEQUENCE: 43

```
Met Arg Cys Leu Ala Glu Phe Leu Gly Leu Leu Val Leu Trp Ile Pro
1               5                   10                  15
Gly Ala Ile Gly Asp Ile Val Met Thr Gln Ala Ala Pro Ser Val Pro
            20                  25                  30
Val Thr Pro Gly Glu Ser Val Ser Ile Ser Cys Arg Ser Ser Lys Ser
        35                  40                  45
Leu Leu His Ser Asn Gly Asn Thr Tyr Leu Tyr Trp Phe Leu Gln Arg
    50                  55                  60
Pro Gly Gln Ser Pro Gln Leu Leu Ile Tyr Arg Val Ser Asn Leu Ala
65                  70                  75                  80
Ser Gly Val Pro Asp Arg Phe Ser Gly Ser Gly Ser Gly Thr Ala Phe
                85                  90                  95
Thr Leu Arg Ile Ser Arg Val Glu Ala Glu Asp Val Gly Val Tyr Tyr
            100                 105                 110
Cys Met Gln His Leu Glu Tyr Pro Leu Thr Phe Gly Ala Gly Thr Lys
        115                 120                 125
Leu Glu Leu Lys
    130
```

<210> SEQ ID NO 44
<211> LENGTH: 372
<212> TYPE: DNA
<213> ORGANISM: Artificial Sequence
<220> FEATURE:
<223> OTHER INFORMATION: Hu9D5VHv1

<400> SEQUENCE: 44

```
gaggtgcagc tggtggagtc cggcggcggc ctggtgcagc ccggcggctc cctgcgcctg      60
tcctgcgccg cctccggctt caccttctcc tcctacacca tgtcctgggt cgcccaggcc     120
cccggcaagg gcctggagct ggtggccgag atctccaact ccggcgacac cacctactac     180
```

| | |
|---|---|
| cccgacaccg tgaagggccg cttcaccttc tcccgcgaca acgccaagaa ctccctgtac | 240 |
| ctgcagtcca actccctgaa ggccgaggac accgccgtgt actactgcgc ccgccactac | 300 |
| tactacggcg gcggctacgg cggctggttc ttcgacgtgt ggggccaggg caccaccgtg | 360 |
| accgtgtcct ca | 372 |

<210> SEQ ID NO 45
<211> LENGTH: 372
<212> TYPE: DNA
<213> ORGANISM: Artificial Sequence
<220> FEATURE:
<223> OTHER INFORMATION: Hu9D5VHv2

<400> SEQUENCE: 45

| | |
|---|---|
| gaggtgcagc tggtggagtc cggcggcggc ctggtgcagc ccggcggctc cctgcgcctg | 60 |
| tcctgcgccg cctccggctt caccttctcc tcctacacca tgtcctgggt cgcccaggcc | 120 |
| cccggcaagg gcctggagct ggtggccgag atctccaact ccggcgacac cacctactac | 180 |
| cccgacaccg tgaagggccg cttcaccttc tcccgcgaca acgccaagaa ctccctgtac | 240 |
| ctgcagtcca acctgctgcg cgccgaggac accgccgtgt actactgcgc ccgccactac | 300 |
| tactacggcg gcggctacgg cggctggttc ttcgacgtgt ggggccaggg caccaccgtg | 360 |
| accgtgtcct ca | 372 |

<210> SEQ ID NO 46
<211> LENGTH: 372
<212> TYPE: DNA
<213> ORGANISM: Artificial Sequence
<220> FEATURE:
<223> OTHER INFORMATION: Hu9D5VHv2b

<400> SEQUENCE: 46

| | |
|---|---|
| gaggtgcaac tggtggagtc tggcggcggc ttggtgcaac ctggcggctc cctgaagctg | 60 |
| tcctgtgccg cctccggctt caccttcagc agctatacca tgtcttgggt cgccaaacc | 120 |
| cccgagaaga ggctggagtt ggtggctgag attagtaata gcggcgatac cacctactat | 180 |
| cccgataccg tgaagggccg cttcaccatt tccagagata tgctaagaa tccctgtat | 240 |
| ctgcaaatga gtagcctgaa gtctgaggat accgctatgt attattgtgc tagacattat | 300 |
| tattatggcg gcggctatgg cggctggttc ttcgatgtgt ggggccaagg caccctggtc | 360 |
| accgtgtcct ca | 372 |

<210> SEQ ID NO 47
<211> LENGTH: 372
<212> TYPE: DNA
<213> ORGANISM: Artificial Sequence
<220> FEATURE:
<223> OTHER INFORMATION: Hu9D5VHv3

<400> SEQUENCE: 47

| | |
|---|---|
| gaggtgcagc tggtggagtc cggcggcggc ctggtgcagc ccggcggctc cctgcgcctg | 60 |
| tcctgcgccg cctccggctt caccttctcc tcctacacca tgtcctgggt cgcccaggcc | 120 |
| cccggcaagg gcctggagtg ggtgtccgag atctccaact ccggcgacac cacctactac | 180 |
| cccgacaccg tgaagggccg cttcaccttc tcccgcgaca acgccaagaa ctccctgtac | 240 |
| ctgcagtcca acctgctgcg cgccgaggac accgccgtgt actactgcgc ccgccactac | 300 |
| tactacggcg gcggctacgg cggctggttc ttcgacgtgt ggggccaggg caccaccgtg | 360 |
| accgtgtcct ca | 372 |

<210> SEQ ID NO 48
<211> LENGTH: 372
<212> TYPE: DNA
<213> ORGANISM: Artificial Sequence
<220> FEATURE:
<223> OTHER INFORMATION: Hu9D5VHv3b

<400> SEQUENCE: 48

```
gaggtgcaac tggtggagtc tggcggcggc ttggtgcaac ctggcggctc cctgaagctg      60
tcctgtgccg cctccggctt caccttcagc agctatacca tgtcttgggt gcgccaaacc     120
cccgggaaga ggctggagtt ggtggctgag attagtaata gcggcgatac cacctactat     180
cccgataccg tgaagggccg cttcaccatt tccagagata atgctaagaa taccctgtat     240
ctgcaaatga gtagcctgaa gtctgaggat accgctatgt attattgtgc tagacattat     300
tattatggcg gcggctatgg cggctggttc ttcgatgtgt ggggccaagg caccctggtc     360
accgtgtcct ca                                                         372
```

<210> SEQ ID NO 49
<211> LENGTH: 372
<212> TYPE: DNA
<213> ORGANISM: Artificial Sequence
<220> FEATURE:
<223> OTHER INFORMATION: Hu9D5VHv4

<400> SEQUENCE: 49

```
gaggtgcagc tggtggagtc cggcggcggc ctggtgcagc ccggcggctc cctgcgcctg      60
tcctgcgccg cctccggctt caccttctcc tcctacacca tgtcctgggt gcgccaggcc     120
cccggcaagg gcctggagtg ggtgtccgag atctccaact ccggcgacac cacctactac     180
cccgacaccg tgaagggccg cttcaccatc tcccgcgaca acgccaagaa ctccctgtac     240
ctgcagtcca acctgctgcg cgccgaggac accgccgtgt actactgcgc cgccactac     300
tactacggcg gcggctacgg cggctggttc ttcgacgtgt ggggccaggg caccaccgtg     360
accgtgtcct ca                                                         372
```

<210> SEQ ID NO 50
<211> LENGTH: 372
<212> TYPE: DNA
<213> ORGANISM: Artificial Sequence
<220> FEATURE:
<223> OTHER INFORMATION: Hu9D5VHv4b

<400> SEQUENCE: 50

```
gaggtgcaac tggtggagtc tggcggcggc ttggtgcaac ctggcggctc cctgaagctg      60
tcctgtgccg cctccggctt caccttcagc agctatacca tgtcttgggt gcgccaagcc     120
cccgggaaga ggctggagtt ggtggctgag attagtaata gcggcgatac cacctactat     180
cccgataccg tgaagggccg cttcaccatt tccagagata atgctaagaa taccctgtat     240
ctgcaaatga gtagcctgaa gtctgaggat accgctatgt attattgtgc tagacattat     300
tattatggcg gcggctatgg cggctggttc ttcgatgtgt ggggccaagg caccctggtc     360
accgtgtcct ca                                                         372
```

<210> SEQ ID NO 51
<211> LENGTH: 372
<212> TYPE: DNA
<213> ORGANISM: Artificial Sequence
<220> FEATURE:

<223> OTHER INFORMATION: Hu9D5VHv5

<400> SEQUENCE: 51

| | |
|---|---|
| gaggtgcagc tggtggagtc cggcggcggc ctggtgcagc cggcggctc cctgcgcctg | 60 |
| tcctgcgccg cctccggctt caccttctcc tcctacacca tgtcctgggt gcgccagacc | 120 |
| cccgagaagc gcctggagct ggtggccgag atctccaact ccggcgacac cacctactac | 180 |
| cccgacaccg tgaagggccg cttcaccatc tcccgcgaca cgccaagaa caccctgtac | 240 |
| ctgcagatga acctgctgcg cgccgaggac accgccgtgt actactgcgc cgccactac | 300 |
| tactacggcg gcggctacgg cggctggttc ttcgacgtgt ggggccaagg caccaccgtg | 360 |
| accgtgtcct ca | 372 |

<210> SEQ ID NO 52
<211> LENGTH: 336
<212> TYPE: DNA
<213> ORGANISM: Artificial Sequence
<220> FEATURE:
<223> OTHER INFORMATION: Hu9D5VLv1

<400> SEQUENCE: 52

| | |
|---|---|
| gacatcgtga tgacccagtc cccctgtcc ctgcccgtga ccccggcga gcccgcctcc | 60 |
| atctcctgcc gctcctccaa gtccctgctg cactccaacg gcaacaccta cctgtactgg | 120 |
| ttcctgcaga agcccggcca gtccccccag ctgctgatct accgcgtgtc caacctggcc | 180 |
| tccggcgtgc ccgaccgctt ctccggctcc ggctccggca ccgacttcac cctgaagatc | 240 |
| tcccgcgtgg aggccgagga cgtgggcgtg tactactgca tgcagcacct ggagtacccc | 300 |
| ctgaccttcg gccagggcac caagctggag atcaaa | 336 |

<210> SEQ ID NO 53
<211> LENGTH: 336
<212> TYPE: DNA
<213> ORGANISM: Artificial Sequence
<220> FEATURE:
<223> OTHER INFORMATION: Hu9D5VLv2

<400> SEQUENCE: 53

| | |
|---|---|
| gacatcgtga tgacccagtc cccctgtcc ctgcccgtga ccccggcga gcccgcctcc | 60 |
| atctcctgcc gctcctccaa gtccctgctg cactccaacg gcaacaccta cctgtactgg | 120 |
| tacctgcaga agcccggcca gtccccccag ctgctgatct accgcgtgtc caacctggcc | 180 |
| tccggcgtgc ccgaccgctt ctccggctcc ggctccggca ccgacttcac cctgaagatc | 240 |
| tcccgcgtgg aggccgagga cgtgggcgtg tactactgca tgcagcacct ggagtacccc | 300 |
| ctgaccttcg gccagggcac caagctggag atcaaa | 336 |

<210> SEQ ID NO 54
<211> LENGTH: 336
<212> TYPE: DNA
<213> ORGANISM: Artificial Sequence
<220> FEATURE:
<223> OTHER INFORMATION: Hu9D5VLv3

<400> SEQUENCE: 54

| | |
|---|---|
| gacatcgtga tgacccagtc cccctgtcc ctgcccgtga ccccggcga gcccgcctcc | 60 |
| atctcctgcc gctcctccaa gtccctgctg cactccaacg gcaacaccta cctgtactgg | 120 |
| tacctgcaga agcccggcca gtccccccag ctgctgatct accgcgtgtc caacctggcc | 180 |
| tccggcgtgc cctcccgctt ctccggctcc ggctccggca ccgacttcac cctgaagatc | 240 |

```
tcccgcgtgg aggccgagga cgtgggcgtg tactactgca tgcagcacct ggagtacccc    300
ctgaccttcg gccagggcac caagctggag atcaaa                              336
```

<210> SEQ ID NO 55
<211> LENGTH: 336
<212> TYPE: DNA
<213> ORGANISM: Artificial Sequence
<220> FEATURE:
<223> OTHER INFORMATION: Hu9D5VLv4

<400> SEQUENCE: 55

```
gacatcgtga tgacccagtc cgccccctcc ctgcccgtga cccccggcga gcccgtgtcc    60
atctcctgcc gctcctccaa gtccctgctg cactccaacg gcaacaccta cctgtactgg   120
ttcctgcagc gccccggcca gtcccccag ctgctgatct accgcgtgtc caacctggcc   180
tccggcgtgc cctcccgctt ctccggctcc ggctccggca ccgccttcac cctgcgcatc   240
tcccgcgtgg aggccgagga cgtgggcgtg tactactgca tgcagcacct ggagtacccc   300
ctgaccttcg gccaaggcac caagctggag atcaaa                              336
```

<210> SEQ ID NO 56
<211> LENGTH: 336
<212> TYPE: DNA
<213> ORGANISM: Artificial Sequence
<220> FEATURE:
<223> OTHER INFORMATION: Hu9D5VLv5

<400> SEQUENCE: 56

```
gacatcgtga tgacccagtc cgccccctcc ctgcccgtga cccccggcga gtccgtgtcc    60
atctcctgcc gctcctccaa gtccctgctg cactccaacg gcaacaccta cctgtactgg   120
ttcctgcagc gccccggcca gtcccccag ctgctgatct accgcgtgtc caacctggcc   180
tccggcgtgc cctcccgctt ctccggctcc ggctccggca ccgccttcac cctgcgcatc   240
tcccgcgtgg aggccgagga cgtgggcgtg tactactgca tgcagcacct ggagtacccc   300
ctgaccttcg gccaaggcac caagctggag atcaaa                              336
```

<210> SEQ ID NO 57
<211> LENGTH: 19
<212> TYPE: PRT
<213> ORGANISM: Artificial Sequence
<220> FEATURE:
<223> OTHER INFORMATION: 9D5VH Signal Peptide

<400> SEQUENCE: 57

```
Met Asp Phe Gly Leu Ser Leu Ile Phe Leu Val Leu Val Leu Lys Gly
1               5                   10                  15

Val Leu Cys
```

<210> SEQ ID NO 58
<211> LENGTH: 57
<212> TYPE: DNA
<213> ORGANISM: Artificial Sequence
<220> FEATURE:
<223> OTHER INFORMATION: 9D5VH Signal Peptide

<400> SEQUENCE: 58

```
atggactttg ggctcagctt gattttcctt gtccttgttt taaaaggtgt cctgtgt       57
```

<210> SEQ ID NO 59
<211> LENGTH: 20

<212> TYPE: PRT
<213> ORGANISM: Artificial Sequence
<220> FEATURE:
<223> OTHER INFORMATION: 9D5VL Signal Peptide

<400> SEQUENCE: 59

Met Arg Cys Leu Ala Glu Phe Leu Gly Leu Leu Val Leu Trp Ile Pro
1               5                   10                  15

Gly Ala Ile Gly
            20

<210> SEQ ID NO 60
<211> LENGTH: 60
<212> TYPE: DNA
<213> ORGANISM: Artificial Sequence
<220> FEATURE:
<223> OTHER INFORMATION: 9D5VL Signal Peptide

<400> SEQUENCE: 60
atgaggtgcc tagctgagtt cctggggctg cttgtgctct ggatccctgg agccattggg    60

<210> SEQ ID NO 61
<211> LENGTH: 124
<212> TYPE: PRT
<213> ORGANISM: Artificial Sequence
<220> FEATURE:
<223> OTHER INFORMATION: m14G8VH

<400> SEQUENCE: 61

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Thr Gly Thr Thr Val Thr Val Ser Ser
        115                 120

<210> SEQ ID NO 62
<211> LENGTH: 118
<212> TYPE: PRT
<213> ORGANISM: Artificial Sequence
<220> FEATURE:
<223> OTHER INFORMATION: 1MQK_H

<400> SEQUENCE: 62

Glu Val Lys Leu Gln Glu Ser Gly Gly Asp Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Ser Ile Asn Asn Gly Gly Gly Arg Thr Tyr Tyr Pro Asp Thr Val

```
                   50                  55                  60
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                     85                  90                  95

Val Arg His Glu Tyr Tyr Tyr Ala Met Asp Tyr Trp Gly Gln Gly Thr
                100                 105                 110

Thr Val Thr Val Ser Ser
            115

<210> SEQ ID NO 63
<211> LENGTH: 124
<212> TYPE: PRT
<213> ORGANISM: Artificial Sequence
<220> FEATURE:
<223> OTHER INFORMATION: AAD30410

<400> SEQUENCE: 63

Gln Val Gln Leu Val Gln Ser Gly Gly Gly Leu Val Gln Pro Gly Gly
 1               5                  10                  15

Ser Arg Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Ala Ile Ser Thr Asp Gly Ser Phe Ile Tyr Tyr Ala Asp Thr Val
        50                  55                  60

Lys Gly Arg Phe Thr Ile Ser Gly Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Ile Asp Ala Thr Ala Gln Val Gly Arg Phe Asp
                100                 105                 110

Pro Trp Gly Gln Gly Thr Leu Val Thr Val Ser Ser
            115                 120

<210> SEQ ID NO 64
<211> LENGTH: 124
<212> TYPE: PRT
<213> ORGANISM: Artificial Sequence
<220> FEATURE:
<223> OTHER INFORMATION: Hu14G8VHv1

<400> SEQUENCE: 64

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Leu Val
            35                  40                  45

Ala Glu Ile Asn Asn Ser Gly Asp Thr Thr Tyr Tyr Pro Asp Thr Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Tyr Tyr Tyr Gly Gly Gly Tyr Gly Gly Trp Phe Phe Asp
                100                 105                 110
```

Val Trp Gly Thr Gly Thr Leu Val Thr Val Ser Ser
            115                 120

<210> SEQ ID NO 65
<211> LENGTH: 124
<212> TYPE: PRT
<213> ORGANISM: Artificial Sequence
<220> FEATURE:
<223> OTHER INFORMATION: Hu14G8VHv2

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
            115                 120

<210> SEQ ID NO 66
<211> LENGTH: 124
<212> TYPE: PRT
<213> ORGANISM: Artificial Sequence
<220> FEATURE:
<223> OTHER INFORMATION: Hu14G8VHv3

<400> SEQUENCE: 66

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
            115                 120

<210> SEQ ID NO 67
<211> LENGTH: 5
<212> TYPE: PRT
<213> ORGANISM: Artificial Sequence
<220> FEATURE:
<223> OTHER INFORMATION: 14G8 CDRH1 - Kabat

```
<400> SEQUENCE: 67

Ser Tyr Thr Met Ser
1               5

<210> SEQ ID NO 68
<211> LENGTH: 17
<212> TYPE: PRT
<213> ORGANISM: Artificial Sequence
<220> FEATURE:
<223> OTHER INFORMATION: 14G8 CDRH2 - Kabat

<400> SEQUENCE: 68

Glu Ile Asn Asn Ser Gly Asp Thr Thr Tyr Tyr Pro Asp Thr Val Lys
1               5                   10                  15

Gly

<210> SEQ ID NO 69
<211> LENGTH: 15
<212> TYPE: PRT
<213> ORGANISM: Artificial Sequence
<220> FEATURE:
<223> OTHER INFORMATION: 14G8 CDRH3 - Kabat

<400> SEQUENCE: 69

His Tyr Tyr Tyr Gly Gly Gly Tyr Gly Gly Trp Phe Phe Asp Val
1               5                   10                  15

<210> SEQ ID NO 70
<211> LENGTH: 113
<212> TYPE: PRT
<213> ORGANISM: Artificial Sequence
<220> FEATURE:
<223> OTHER INFORMATION: m14G8VL

<400> SEQUENCE: 70

Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

Arg

<210> SEQ ID NO 71
<211> LENGTH: 113
<212> TYPE: PRT
<213> ORGANISM: Artificial Sequence
<220> FEATURE:
<223> OTHER INFORMATION: MJU_L

<400> SEQUENCE: 71

Asp Ile Val Met Thr Gln Ala Ala Pro Ser Val Pro Val Thr Pro Gly
1               5                   10                  15
```

-continued

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Phe Thr Phe Gly Ala Gly Thr Lys Leu Glu Leu Lys
            100                 105                 110

Arg

<210> SEQ ID NO 72
<211> LENGTH: 113
<212> TYPE: PRT
<213> ORGANISM: Artificial Sequence
<220> FEATURE:
<223> OTHER INFORMATION: ABA71374

<400> SEQUENCE: 72

Asp Ile Val Met Thr Gln Thr Pro Leu Ser Leu Pro Val Thr Pro Gly
1               5                   10                  15

Glu Ser Ala Ser Ile Ser Cys Arg Ser Ser Gln Ser Leu Arg His Tyr
            20                  25                  30

Ser Gly Tyr Thr Tyr Ile Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Val Cys Ser Phe Gly Gln Gly Thr Lys Leu Glu Ile Lys
            100                 105                 110

Arg

<210> SEQ ID NO 73
<211> LENGTH: 113
<212> TYPE: PRT
<213> ORGANISM: Artificial Sequence
<220> FEATURE:
<223> OTHER INFORMATION: ABC66952

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Asn Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Ser Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala

```
                        85                  90                  95

Leu Gln Ser Pro Tyr Thr Phe Gly Gln Gly Thr Lys Leu Glu Ile Lys
                100                 105                 110

Arg

<210> SEQ ID NO 74
<211> LENGTH: 113
<212> TYPE: PRT
<213> ORGANISM: Artificial Sequence
<220> FEATURE:
<223> OTHER INFORMATION: Hu14G8VLv1

<400> SEQUENCE: 74

Asp Ile Val Met Thr Gln Ser Ala Pro Ser Leu Pro Val Thr Pro Gly
1               5                   10                  15

Glu Ser Val Ser Ile Ser Cys Arg Ser Asn Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
                100                 105                 110

Arg

<210> SEQ ID NO 75
<211> LENGTH: 113
<212> TYPE: PRT
<213> ORGANISM: Artificial Sequence
<220> FEATURE:
<223> OTHER INFORMATION: Hu14G8VLv2

<400> SEQUENCE: 75

Asp Ile Val Met Thr Gln Ser Pro Leu Ser Leu Pro Val Thr Pro Gly
1               5                   10                  15

Glu Pro Ala Ser Ile Ser Cys Arg Ser Asn Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
                100                 105                 110

Arg

<210> SEQ ID NO 76
<211> LENGTH: 113
<212> TYPE: PRT
<213> ORGANISM: Artificial Sequence
<220> FEATURE:
```

<223> OTHER INFORMATION: Hu14G8VLv3

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg

<210> SEQ ID NO 77
<211> LENGTH: 16
<212> TYPE: PRT
<213> ORGANISM: Artificial Sequence
<220> FEATURE:
<223> OTHER INFORMATION: 14G8 CDRL1 (mouse, HuVLv1, HuVLv2) - Kabat

<400> SEQUENCE: 77

Arg Ser Asn Lys Ser Leu Leu His Ser Asn Gly Asn Thr Tyr Leu Tyr
1               5                   10                  15

<210> SEQ ID NO 78
<211> LENGTH: 7
<212> TYPE: PRT
<213> ORGANISM: Artificial Sequence
<220> FEATURE:
<223> OTHER INFORMATION: 14G8 CDRL2 - Kabat

<400> SEQUENCE: 78

Arg Val Ser Asn Leu Ala Ser
1               5

<210> SEQ ID NO 79
<211> LENGTH: 9
<212> TYPE: PRT
<213> ORGANISM: Artificial Sequence
<220> FEATURE:
<223> OTHER INFORMATION: 14G8 CDRL3 - Kabat

<400> SEQUENCE: 79

Met Gln His Leu Glu Tyr Pro Leu Thr
1               5

<210> SEQ ID NO 80
<211> LENGTH: 16
<212> TYPE: PRT
<213> ORGANISM: Artificial Sequence
<220> FEATURE:
<223> OTHER INFORMATION: 14G8 CDRL1 (HuVLv3) - Kabat

<400> SEQUENCE: 80

Arg Ser Ser Lys Ser Leu Leu His Ser Asn Gly Asn Thr Tyr Leu Tyr
1               5                   10                  15

<210> SEQ ID NO 81
<211> LENGTH: 454
<212> TYPE: PRT
<213> ORGANISM: Artificial Sequence
<220> FEATURE:
<223> OTHER INFORMATION: Hu14G8 H1 heavy chain

<400> SEQUENCE: 81

```
Glu Val Lys Leu Val Glu Ser Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Gly Gly Gly Tyr Gly Gly Trp Phe Phe Asp
            100                 105                 110

Val Trp Gly Thr Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365
```

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 82
<211> LENGTH: 454
<212> TYPE: PRT
<213> ORGANISM: Artificial Sequence
<220> FEATURE:
<223> OTHER INFORMATION: Hu14G8 H2 heavy chain

<400> SEQUENCE: 82

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
            35                  40                  45

Ala Glu Ile Asn Asn Ser Gly Asp Thr Thr Tyr Tyr Pro Asp Thr Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

```
Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 83
<211> LENGTH: 454
<212> TYPE: PRT
<213> ORGANISM: Artificial Sequence
<220> FEATURE:
<223> OTHER INFORMATION: Hu14G8 H3 heavy chain

<400> SEQUENCE: 83

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
    115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

```
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Arg Val Glu Pro
        210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 84
<211> LENGTH: 219
<212> TYPE: PRT
<213> ORGANISM: Artificial Sequence
<220> FEATURE:
<223> OTHER INFORMATION: Hu14G8 L1 light chain

<400> SEQUENCE: 84

Asp Ile Val Met Thr Gln Ser Ala Pro Ser Leu Pro Val Thr Pro Gly
1               5                   10                  15
Glu Ser Val Ser Ile Ser Cys Arg Ser Asn Lys Ser Leu Leu His Ser
            20                  25                  30
Asn Gly Asn Thr Tyr Leu Tyr Trp Phe Leu Gln Lys Pro Gly Gln Ser
        35                  40                  45
Pro Gln Leu Leu Ile Tyr Arg Val Ser Asn Leu Ala Ser Gly Val Pro
    50                  55                  60
Asp Arg Phe Ser Gly Ser Gly Ser Gly Thr Ala Phe Thr Leu Lys Ile
65                  70                  75                  80
```

Ser Arg Val Glu Ala Glu Asp Val Gly Val Tyr Tyr Cys Met Gln His
            85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 85
<211> LENGTH: 219
<212> TYPE: PRT
<213> ORGANISM: Artificial Sequence
<220> FEATURE:
<223> OTHER INFORMATION: Hu14G8 L2 light chain

<400> SEQUENCE: 85

Asp Ile Val Met Thr Gln Ser Pro Leu Ser Leu Pro Val Thr Pro Gly
1               5                   10                  15

Glu Pro Ala Ser Ile Ser Cys Arg Ser Asn Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
            85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 86
<211> LENGTH: 219
<212> TYPE: PRT
<213> ORGANISM: Artificial Sequence
<220> FEATURE:
<223> OTHER INFORMATION: Hu14G8 L3 light chain

<400> SEQUENCE: 86

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 87
<211> LENGTH: 429
<212> TYPE: DNA
<213> ORGANISM: Artificial Sequence
<220> FEATURE:
<223> OTHER INFORMATION: m14G8VH with signal peptide

<400> SEQUENCE: 87

| | |
|---|---|
| atgaatttcg ggctcagctt gattttcctt gtccttgttt taaaaggtgt cctgtgtgaa | 60 |
| gtgaagctgg tggagtctgg gggaggttta gtgcagcctg agggtccct gaaactctcc | 120 |
| tgtgcagcct ccggattcac tttcagtagc tataccatgt cttgggttcg ccagactcca | 180 |
| gaaaagaggc tggagttggt cgcagaaatt aataatagtg gtgataccac ctactatcca | 240 |
| gacactgtaa agggccgatt caccatctcc agagacaatg ccaagaacac cctgtacctg | 300 |
| caaatgagca gtctgaagtc tgaggacacg gccatgtatt actgtgcaag acattattac | 360 |
| tatggtggtg ctacggggg gtggttcttc gatgtctggg gcacagggac cacggtcacc | 420 |
| gtctcctca | 429 |

```
<210> SEQ ID NO 88
<211> LENGTH: 143
<212> TYPE: PRT
<213> ORGANISM: Artificial Sequence
<220> FEATURE:
<223> OTHER INFORMATION: m14G8VH with signal peptide

<400> SEQUENCE: 88

Met Asn Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Leu Val Ala Glu Ile Asn Asn Ser Gly Asp Thr Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Tyr Tyr Tyr Gly Gly Tyr Gly Gly Trp
        115                 120                 125

Phe Phe Asp Val Trp Gly Thr Gly Thr Thr Val Thr Val Ser Ser
    130                 135                 140

<210> SEQ ID NO 89
<211> LENGTH: 399
<212> TYPE: DNA
<213> ORGANISM: Artificial Sequence
<220> FEATURE:
<223> OTHER INFORMATION: m14G8VL with signal peptide

<400> SEQUENCE: 89
atgaggtgcc tagctgagtt cctggggctg cttgtgctct ggatccctgg agccattggg    60
gatattgtga tgactcaggc tgcaccctct gtacctgtca ctcctggaga gtcagtatcc   120
atctcctgca ggtctaataa gagtctcctg catagtaatg caacactta cttgtattgg    180 ttcctgcaga ggccaggcca gtctcctcaa ctcctgatat atcgggtgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacattt agaatatccg   360
ctcacgttcg gtgctgggac caagctggag ctgaaacgt                           399

<210> SEQ ID NO 90
<211> LENGTH: 133
<212> TYPE: PRT
<213> ORGANISM: Artificial Sequence
<220> FEATURE:
<223> OTHER INFORMATION: m14G8VL with signal peptide

<400> SEQUENCE: 90

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Asn Lys Ser
        35                  40                  45
```

```
Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Val Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Ile Ser Arg Val Glu Ala Glu Asp Val Gly Val Tyr Tyr
                100                 105                 110

Cys Met Gln His Leu Glu Tyr Pro Leu Thr Phe Gly Ala Gly Thr Lys
            115                 120                 125

Leu Glu Leu Lys Arg
    130

<210> SEQ ID NO 91
<211> LENGTH: 372
<212> TYPE: DNA
<213> ORGANISM: Artificial Sequence
<220> FEATURE:
<223> OTHER INFORMATION: Hu14G8VHv1

<400> SEQUENCE: 91
gaggtgaagc tggtggagtc tggcggcggc ttggtgcaac ctggcggctc cctgaagctg      60
tcctgtgccg cctccggctt caccttcagc agctatacca tgtcttgggt gcgccaaacc     120
cccgagaaga ggctggagtt ggtggctgag attaataata gcggcgatac cacctactat     180
cccgataccg tgaagggccg cttcaccatt tccagagata atgctaagaa taccctgtat     240
ctgcaaatga gtagcctgaa gtctgaggat accgctatgt attattgtgc tagacattat     300
tattatggcg gcggctatgg cggctggttc ttcgatgtgt ggggcaccgg caccctggtc     360
accgtgtcct ca                                                         372

<210> SEQ ID NO 92
<211> LENGTH: 372
<212> TYPE: DNA
<213> ORGANISM: Artificial Sequence
<220> FEATURE:
<223> OTHER INFORMATION: Hu14G8VHv2

<400> SEQUENCE: 92
gaggtgcaac tggtggagtc tggcggcggc ttggtgcaac ctggcggctc cctgaagctg      60
tcctgtgccg cctccggctt caccttcagc agctatacca tgtcttgggt gcgccaaacc     120
cccgagaaga ggctggagtt ggtggctgag attaataata gcggcgatac cacctactat     180
cccgataccg tgaagggccg cttcaccatt tccagagata atgctaagaa taccctgtat     240
ctgcaaatga gtagcctgaa gtctgaggat accgctatgt attattgtgc tagacattat     300
tattatggcg gcggctatgg cggctggttc ttcgatgtgt ggggccaagg caccctggtc     360
accgtgtcct ca                                                         372

<210> SEQ ID NO 93
<211> LENGTH: 372
<212> TYPE: DNA
<213> ORGANISM: Artificial Sequence
<220> FEATURE:
<223> OTHER INFORMATION: Hu14G8VHv3

<400> SEQUENCE: 93
gaggtgcaac tggtggagtc tggcggcggc ttggtgcaac ctggcggctc cctgaagctg      60
tcctgtgccg cctccggctt caccttcagc agctatacca tgtcttgggt gcgccaaacc     120
```

```
cccgagaaga ggctggagtt ggtggctgag attaataata gcggcgatac cacctactat    180
cccgataccg tgaagggccg cttcaccatt tccagagata atgctaagaa taccctgtat    240
ctgcaaatga atagcctgag ggctgaggat accgctgtgt attattgtgc tagacattat    300
tattatggcg gcggctatgg cggctggttc ttcgatgtgt ggggccaagg caccctggtc    360
accgtgtcct ca                                                        372

<210> SEQ ID NO 94
<211> LENGTH: 339
<212> TYPE: DNA
<213> ORGANISM: Artificial Sequence
<220> FEATURE:
<223> OTHER INFORMATION: Hu14G8VLv1

<400> SEQUENCE: 94
gatatcgtga tgacccagtc tgccccctcc ctgcctgtga cccctggcga gtccgtgtcc     60
atctcctgcc ggtccaacaa gagcctgctg cacagcaacg gcaacaccta cctgtactgg    120
ttcctgcaaa agcccggcca atcccctcaa ctgctgatct accgggtgtc caacctggcc    180
tccggcgtgc ccgataggtt ctccggaagc ggctccggca ccgccttcac cctgaagatt    240
agtagagtcg aggccgagga tgtgggcgtg tactactgta tgcaacactt ggagtacccc    300
ctgacgttcg gccaaggcac caagctggag atcaagcgt                            339

<210> SEQ ID NO 95
<211> LENGTH: 339
<212> TYPE: DNA
<213> ORGANISM: Artificial Sequence
<220> FEATURE:
<223> OTHER INFORMATION: Hu14G8VLv2

<400> SEQUENCE: 95
gatatcgtga tgacccagtc tcccctgtcc ctgcctgtga cccctggcga gcccgcctcc     60
atctcctgcc ggtccaacaa gagcctgctg cacagcaacg gcaacaccta cctgtactgg    120
ttcctgcaaa agcccggcca atcccctcaa ctgctgatct accgggtgtc caacctggcc    180
tccggcgtgc ccgataggtt ctccggaagc ggctccggca ccgatttcac cctgaagatt    240
agtagagtcg aggccgagga tgtgggcgtg tactactgta tgcaacactt ggagtacccc    300
ctgacgttcg gccaaggcac caagctggag atcaagcgt                            339

<210> SEQ ID NO 96
<211> LENGTH: 339
<212> TYPE: DNA
<213> ORGANISM: Artificial Sequence
<220> FEATURE:
<223> OTHER INFORMATION: Hu14G8VLv3

<400> SEQUENCE: 96
gatatcgtga tgacccagtc tcccctgtcc ctgcctgtga cccctggcga gcccgcctcc     60
atctcctgcc ggtccagcaa gagcctgctg cacagcaacg gcaacaccta cctgtactgg    120
ttcctgcaaa agcccggcca atcccctcaa ctgctgatct accgggtgtc caacctggcc    180
tccggcgtgc ccagtaggtt ctccggaagc ggctccggca ccgatttcac cctgaagatt    240
agtagagtcg aggccgagga tgtgggcgtg tactactgta tgcaacactt ggagtacccc    300
ctgacgttcg gccaaggcac caagctggag atcaagcgt                            339

<210> SEQ ID NO 97
```

```
<211> LENGTH: 19
<212> TYPE: PRT
<213> ORGANISM: Artificial Sequence
<220> FEATURE:
<223> OTHER INFORMATION: 14G8VH Signal Peptide

<400> SEQUENCE: 97

Met Asn Phe Gly Leu Ser Leu Ile Phe Leu Val Leu Val Leu Lys Gly
1               5                   10                  15

Val Leu Cys

<210> SEQ ID NO 98
<211> LENGTH: 57
<212> TYPE: DNA
<213> ORGANISM: Artificial Sequence
<220> FEATURE:
<223> OTHER INFORMATION: 14G8VH Signal Peptide

<400> SEQUENCE: 98
atgaatttcg gcctgagctt gattttcctg gtgctggtgt tgaagggcgt gctgtgt       57

<210> SEQ ID NO 99
<211> LENGTH: 20
<212> TYPE: PRT
<213> ORGANISM: Artificial Sequence
<220> FEATURE:
<223> OTHER INFORMATION: 14G8VL Signal Peptide

<400> SEQUENCE: 99

Met Arg Cys Leu Ala Glu Phe Leu Gly Leu Leu Val Leu Trp Ile Pro
1               5                   10                  15

Gly Ala Ile Gly
            20

<210> SEQ ID NO 100
<211> LENGTH: 60
<212> TYPE: DNA
<213> ORGANISM: Artificial Sequence
<220> FEATURE:
<223> OTHER INFORMATION: 14G8VL Signal Peptide

<400> SEQUENCE: 100
atgaggtgcc tggccgagtt cctgggcctg ctggtgctgt ggatccctgg cgccatcggc    60

<210> SEQ ID NO 101
<211> LENGTH: 330
<212> TYPE: PRT
<213> ORGANISM: Artificial Sequence
<220> FEATURE:
<223> OTHER INFORMATION: Human IgG1 heavy chain constant region

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                         85                  90                  95
Arg Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 102
<211> LENGTH: 330
<212> TYPE: PRT
<213> ORGANISM: Artificial Sequence
<220> FEATURE:
<223> OTHER INFORMATION: Human IgG1 heavy chain constant region of IgG1
      G1m3 allotype

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                    100                 105                 110
```

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 103
<211> LENGTH: 330
<212> TYPE: PRT
<213> ORGANISM: Artificial Sequence
<220> FEATURE:
<223> OTHER INFORMATION: Human IgG1 heavy chain constant region of IgG1
      G1m3 allotype

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 107
<212> TYPE: PRT
<213> ORGANISM: Artificial Sequence
<220> FEATURE:
<223> OTHER INFORMATION: Human kappa light chain constant region

<400> SEQUENCE: 104

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 105
<211> LENGTH: 106
<212> TYPE: PRT
<213> ORGANISM: Artificial Sequence
<220> FEATURE:
<223> OTHER INFORMATION: Human kappa light chain constant region

<400> SEQUENCE: 105

Thr Val Ala Ala Pro Ser Val Phe Ile Phe Pro Pro Ser Asp Glu Gln
```

```
1               5                   10                  15
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

```
<210> SEQ ID NO 106
<211> LENGTH: 990
<212> TYPE: DNA
<213> ORGANISM: Artificial Sequence
<220> FEATURE:
<223> OTHER INFORMATION: Human IgG1 heavy chain constant region of IgG1
      G1m3 allotype

<400> SEQUENCE: 106
gcctccacca agggtccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctggggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa                                    990
```

```
<210> SEQ ID NO 107
<211> LENGTH: 321
<212> TYPE: DNA
<213> ORGANISM: Artificial Sequence
<220> FEATURE:
<223> OTHER INFORMATION: Human kappa light chain constant region

<400> SEQUENCE: 107
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
```

```
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 108
<211> LENGTH: 318
<212> TYPE: DNA
<213> ORGANISM: Artificial Sequence
<220> FEATURE:
<223> OTHER INFORMATION: Human kappa light chain constant region

<400> SEQUENCE: 108
actgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc    180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgt                                                 318

<210> SEQ ID NO 109
<211> LENGTH: 147
<212> TYPE: PRT
<213> ORGANISM: Homo sapiens

<400> SEQUENCE: 109
```

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

```
<210> SEQ ID NO 110
<211> LENGTH: 127
<212> TYPE: PRT
<213> ORGANISM: Homo sapiens

<400> SEQUENCE: 110
```

Gly Pro Thr Gly Thr Gly Glu Ser Lys Cys Pro Leu Met Val Lys Val
1               5                   10                  15

-continued

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Gln Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 111
<211> LENGTH: 127
<212> TYPE: PRT
<213> ORGANISM: Homo sapiens

<400> SEQUENCE: 111

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Gln Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 112
<211> LENGTH: 138
<212> TYPE: PRT
<213> ORGANISM: Homo sapiens

<400> SEQUENCE: 112

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

```
Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Ser Tyr Ser
        115                 120                 125

Thr Thr Ala Val Val Thr Asn Pro Lys Glu
    130                 135

<210> SEQ ID NO 113
<211> LENGTH: 9
<212> TYPE: PRT
<213> ORGANISM: Artificial Sequence
<220> FEATURE:
<223> OTHER INFORMATION: Transthyretin residues 89-97

<400> SEQUENCE: 113

Glu His Ala Glu Val Val Phe Thr Ala
1               5

<210> SEQ ID NO 114
<211> LENGTH: 15
<212> TYPE: PRT
<213> ORGANISM: Artificial Sequence
<220> FEATURE:
<223> OTHER INFORMATION: Potential transthyretin immunogen

<400> SEQUENCE: 114

Gly Gly Glu His Ala Glu Val Val Phe Thr Ala Gly Gly Lys Gly
1               5                   10                  15

<210> SEQ ID NO 115
<211> LENGTH: 12
<212> TYPE: PRT
<213> ORGANISM: Artificial Sequence
<220> FEATURE:
<223> OTHER INFORMATION: Potential transthyretin immunogen

<400> SEQUENCE: 115

Cys Gly Gly Glu His Ala Glu Val Val Phe Thr Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Potential transthyretin immunogen

<400> SEQUENCE: 116

Glu His Ala Glu Val Val Phe Thr Ala Cys Gly Gly
1               5                   10

<210> SEQ ID NO 117
<211> LENGTH: 10
<212> TYPE: PRT
<213> ORGANISM: Artificial Sequence
<220> FEATURE:
<223> OTHER INFORMATION: 9D5 CDRH1 - Composite Chothia-Kabat

<400> SEQUENCE: 117

Gly Phe Thr Phe Ser Ser Tyr Thr Met Ser
1               5                   10

<210> SEQ ID NO 118
<211> LENGTH: 10
<212> TYPE: PRT
<213> ORGANISM: Artificial Sequence
```

```
<220> FEATURE:
<223> OTHER INFORMATION: 14G8 CDRH1 - Composite Chothia-Kabat

<400> SEQUENCE: 118

Gly Phe Thr Phe Ser Ser Tyr Thr Met Ser
1               5                   10
```